United States Patent
Lamrani et al.

(10) Patent No.: US 12,064,237 B2
(45) Date of Patent: *Aug. 20, 2024

(54) DETERMINATION SYSTEM, COMPUTING DEVICE, DETERMINATION METHOD, AND PROGRAM

(71) Applicant: Menicon Co., Ltd., Nagoya (JP)

(72) Inventors: Mouad Lamrani, Geneva (CH); Stephen D. Newman, Singapore (SG); Sami Antero Lakka, Lempaala (FI)

(73) Assignee: Menicon Co., Ltd., Nagoya (JP)

( * ) Notice: Subject to any disclaimer, the term of this patent is extended or adjusted under 35 U.S.C. 154(b) by 919 days.

This patent is subject to a terminal disclaimer.

(21) Appl. No.: 16/980,196

(22) PCT Filed: Mar. 12, 2019

(86) PCT No.: PCT/JP2019/010062
§ 371 (c)(1),
(2) Date: Sep. 11, 2020

(87) PCT Pub. No.: WO2019/176952
PCT Pub. Date: Sep. 19, 2019

(65) Prior Publication Data
US 2021/0007670 A1    Jan. 14, 2021

Related U.S. Application Data

(60) Provisional application No. 62/642,176, filed on Mar. 13, 2018, provisional application No. 62/642,897, (Continued)

(51) Int. Cl.
*A61B 5/145*    (2006.01)
*A45C 11/00*    (2006.01)
(Continued)

(52) U.S. Cl.
CPC ........ *A61B 5/14532* (2013.01); *A45C 11/005* (2013.01); *A45C 15/00* (2013.01);
(Continued)

(58) Field of Classification Search
CPC ....... A61B 5/14532; A61B 3/101; A61B 3/16; A61B 5/0004; A61B 5/14507;
(Continued)

(56) References Cited

U.S. PATENT DOCUMENTS

| 3,545,260 A | 12/1970 | Lichtenstein et al. |
| 3,585,849 A | 6/1971 | Grolman |

(Continued)

FOREIGN PATENT DOCUMENTS

| CN | 104662416 A | 5/2015 |
| EP | 1650567 A1 | 4/2006 |

(Continued)

OTHER PUBLICATIONS

Office Action mailed May 9, 2023 in U.S. Appl. No. 16/979,480.
(Continued)

*Primary Examiner* — Jonathan T Kuo
(74) *Attorney, Agent, or Firm* — Dorsey & Whitney LLP

(57) ABSTRACT

Determination system including: a computing device (i) obtaining information related to an eye of a target person from a plurality of data sources and (ii) making a determination of a predetermined matter related to the target person based on at least part of the information. The plurality of data sources include two or more of a sensor included in a contact lens of the target person, a sensor included in a storage container of the contact lens, a measurement device which carries out measurement related to the eye of the target person, tear fluid of the target person, a storage solution of the contact lens and, a diagnostic process of the target person.

14 Claims, 39 Drawing Sheets

Related U.S. Application Data filed on Mar. 14, 2018, provisional application No. 62/642,860, filed on Mar. 14, 2018, provisional application No. 62/642,875, filed on Mar. 14, 2018, provisional application No. 62/642,926, filed on Mar. 14, 2018, provisional application No. 62/642,913, filed on Mar. 14, 2018.

(51) Int. Cl.

| | | |
|---|---|---|
| A45C 15/00 | (2006.01) | |
| A61B 3/10 | (2006.01) | |
| A61B 3/16 | (2006.01) | |
| A61B 5/00 | (2006.01) | |
| A61B 10/00 | (2006.01) | |
| G01N 33/543 | (2006.01) | |
| G06N 20/00 | (2019.01) | |
| G16H 10/40 | (2018.01) | |
| G16H 50/30 | (2018.01) | |

(52) U.S. Cl.
CPC ............ *A61B 3/101* (2013.01); *A61B 3/16* (2013.01); *A61B 5/0004* (2013.01); *A61B 5/14507* (2013.01); *A61B 5/14546* (2013.01); *A61B 5/411* (2013.01); *A61B 5/412* (2013.01); *A61B 5/4824* (2013.01); *A61B 5/6821* (2013.01); *A61B 5/6847* (2013.01); *A61B 5/7275* (2013.01); *A61B 10/0045* (2013.01); *G01N 33/54366* (2013.01); *G06N 20/00* (2019.01); *G16H 10/40* (2018.01); *G16H 50/30* (2018.01); *A61B 2010/0067* (2013.01)

(58) Field of Classification Search
CPC ..... A61B 5/14546; A61B 5/411; A61B 5/412; A61B 5/4824; A61B 5/6821; A61B 5/6847; A61B 5/7275; A61B 10/0045; A61B 2010/0067; A61B 5/1459; A45C 11/005; A45C 15/00; G01N 33/54366; G06N 20/00; G16H 10/40; G16H 50/30; G16H 50/20; G16H 20/30; G16H 40/63; G02C 11/10; G02C 7/04
See application file for complete search history.

(56) References Cited

U.S. PATENT DOCUMENTS

| | | | |
|---|---|---|---|
| 3,724,263 A | 4/1973 | Rose et al. | |
| 4,305,399 A | 12/1981 | Beale | |
| 4,628,938 A | 12/1986 | Lee | |
| 4,771,792 A | 9/1988 | Seale | |
| 4,860,755 A | 8/1989 | Erath | |
| 4,922,913 A | 5/1990 | Waters et al. | |
| 4,944,303 A | 7/1990 | Katsuragi | |
| 4,947,849 A | 8/1990 | Takahashi et al. | |
| 4,951,671 A | 8/1990 | Coan | |
| 5,005,577 A | 4/1991 | Frenkel | |
| 5,076,274 A | 12/1991 | Matsumoto | |
| 5,109,852 A | 5/1992 | Kaye et al. | |
| 5,148,807 A | 9/1992 | Hsu | |
| 5,165,409 A | 11/1992 | Coan | |
| 5,179,953 A | 1/1993 | Kursar | |
| 5,183,044 A | 2/1993 | Nishio et al. | |
| 5,217,015 A | 6/1993 | Kaye et al. | |
| 5,251,627 A | 10/1993 | Morris | |
| 5,295,495 A | 3/1994 | Maddess | |
| 5,375,595 A | 12/1994 | Sinha et al. | |
| 6,060,256 A | 5/2000 | Everhart et al. | |
| 6,681,127 B2 | 1/2004 | March | |
| 7,429,465 B2 | 9/2008 | Mueller et al. | |
| 8,446,341 B2 | 5/2013 | Amirparviz et al. | |
| 8,870,370 B1 | 10/2014 | Otis et al. | |
| 8,914,089 B2 | 12/2014 | Abreu | |
| 9,730,638 B2 | 8/2017 | Haffner et al. | |
| 10,399,291 B2 | 9/2019 | Hahn et al. | |
| 10,606,100 B2 | 3/2020 | Schmeder et al. | |
| 2001/0034500 A1 | 10/2001 | March | |
| 2004/0176977 A1 | 9/2004 | Broderick et al. | |
| 2004/0181172 A1 | 9/2004 | Carney et al. | |
| 2005/0065753 A1 | 3/2005 | Bigus et al. | |
| 2005/0160009 A1 | 7/2005 | Tanaka et al. | |
| 2006/0224057 A1 | 10/2006 | Burd et al. | |
| 2007/0224275 A1 | 9/2007 | Reid et al. | |
| 2010/0131434 A1 | 5/2010 | Magent et al. | |
| 2010/0203103 A1 | 8/2010 | Dana et al. | |
| 2011/0029322 A1 | 2/2011 | Hindo et al. | |
| 2011/0084834 A1* | 4/2011 | Sabeta ................. | G06K 19/077 340/540 |
| 2011/0117661 A1 | 5/2011 | Daunert et al. | |
| 2012/0138818 A1 | 6/2012 | Pugh et al. | |
| 2012/0245444 A1 | 9/2012 | Otis et al. | |
| 2013/0184554 A1 | 7/2013 | Elsheikh et al. | |
| 2014/0085083 A1 | 3/2014 | Sabeta | |
| 2014/0087452 A1 | 3/2014 | Liu et al. | |
| 2014/0088372 A1 | 3/2014 | Saeedi et al. | |
| 2014/0088381 A1 | 3/2014 | Etzkorn et al. | |
| 2014/0088881 A1 | 3/2014 | Saeedi et al. | |
| 2014/0192312 A1* | 7/2014 | Pletcher ................. | G02C 7/049 351/158 |
| 2014/0194706 A1 | 7/2014 | Liu et al. | |
| 2015/0061837 A1 | 3/2015 | Honoré et al. | |
| 2015/0193588 A1 | 7/2015 | Nemoto et al. | |
| 2017/0020391 A1* | 1/2017 | Flitsch ................. | G16H 40/67 |
| 2017/0042480 A1 | 2/2017 | Gandhi et al. | |
| 2017/0049395 A1* | 2/2017 | Cao ................. | A61B 5/6821 |
| 2017/0085083 A1 | 3/2017 | Berkcan et al. | |
| 2017/0173262 A1 | 6/2017 | Veltz | |
| 2018/0046773 A1 | 2/2018 | Tang et al. | |
| 2018/0189452 A1 | 7/2018 | Serhani et al. | |
| 2018/0267331 A1 | 9/2018 | Abbasi et al. | |
| 2021/0007643 A1* | 1/2021 | Lamrani ................. | G16H 20/30 |

FOREIGN PATENT DOCUMENTS

| | | |
|---|---|---|
| EP | 2280052 A1 | 2/2011 |
| EP | 3287167 A1 | 2/2018 |
| JP | H09105751 A | 4/1997 |
| JP | 2004513389 A | 4/2004 |
| JP | 2004212813 A | 7/2004 |
| JP | 6174232 B1 | 7/2017 |
| WO | 2014209657 A1 | 12/2014 |
| WO | 2015036432 A1 | 3/2015 |
| WO | 2015050174 A1 | 4/2015 |
| WO | 2015157855 A1 | 10/2015 |

OTHER PUBLICATIONS

Office Action mailed Feb. 17, 2023 in Chinese Patent App. No. 201980018752.1 (with English translation).
Office Action mailed Feb. 3, 2023 in Chinese Patent App. No. 201980018492.8 (with English translation).
Office Action mailed Sep. 14, 2021 in Japanese Patent App. No. 2020-570348.
International Search Report and Written Opinion for International Application No. PCT/IB2019/000237, dated Jul. 30, 2019.
International Search Report and Written Opinion for International Application No. PCT/IB2019/000239, dated Jul. 9, 2019.
International Search Report and Written Opinion for International Application No. PCT/IB2019/000240, dated Jul. 30, 2019.
Office Action mailed May 17, 2022 in Japanese Patent App. No. 2020-546426.
Notice of Allowance dated Oct. 25, 2022 for Japanese Application No. 2020-546426.
Extended European Search Report for European Application No. 19767355.1 dated Dec. 7, 2021.
International Search Report and Written Opinion for International Patent Application No. PCT/IB2019/00250, dated Jul. 23, 2019.
International Search Report and Written Opinion for PCT/JP2019/010062, dated Jun. 18, 2019.

(56) References Cited

OTHER PUBLICATIONS

Kim, J., et al., Wearable Smart Sensor Systems Integrated on Soft Contact Lenses for Wireless Ocular Diagnostics, Nature Communications, Published Apr. 27, 2017, Article No. 14997, pp. 1-8.
Extended European Search Report dated Nov. 8, 2021 for European Application No. 19767186.0.
Office Action dated Nov. 2, 2021 for Japanese Application No. 2020-546426.
Final Office Action dated Nov. 28, 2023 for U.S. Appl. No. 16/979,480.
Non-Final Office Action for U.S. Appl. No. 16/979,480 dated Mar. 26, 2024.

* cited by examiner

FIG. 6

| Tear Chemistry | Indication | Possible Cause |
|---|---|---|
| Normal lactoferrin and normal IgE | Normal lacrimal function and no allergic component | Evaporative dry eye |
| Normal lactoferrin and high IgE | Normal lacrimal function and ocular allergy present | Ocular allergy and possible evaporative dry eye |
| Low lactoferrin and normal IgE | Suppressed lacrimal function and no ocular allergy present | Aqueous deficient dry eye |
| Low lactoferrin | Suppressed lacrimal function and contact lens desensitization | Hypoxia, bacterial conjunctivitis and/or contact lens dehydration |
| High lactoferrin | Elevated tear proteins | Excess contact lens deposits |
| High IgE | Ocular allergy present | Giant papillary conjunctivitis or inflammation |

FIG. 18

| Tear Chemistry | Eye Condition | Contact Lens Recommendation |
|---|---|---|
| Normal first biomarker and normal second biomarker | Healthy | Any type of contact lens |
| Normal first biomarker and high second biomarker | Allergic condition | Daily disposable contact lens |
| Low first biomarker and normal second biomarker | Dry eyes | Silicone hydrogel contact lens |
| Low first biomarker | Infection | Rigid gas permeable contact lens |
| High first biomarker | Corneal Strain | Recheck contact lens prescription |
| High second biomarker | Inflammation | Rigid gas permeable contact lens |

FIG. 47
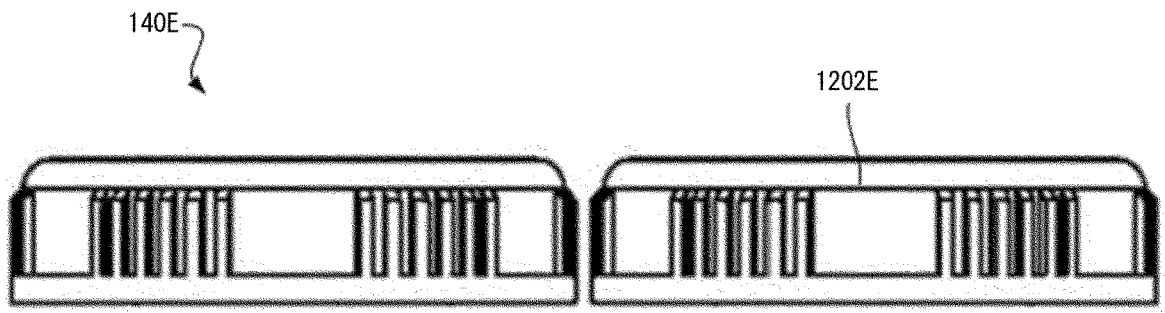
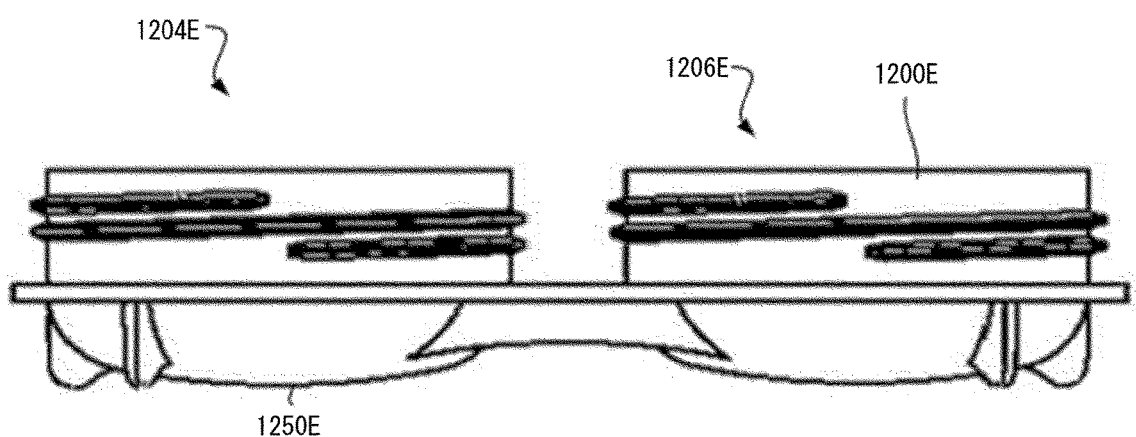
FIG. 48
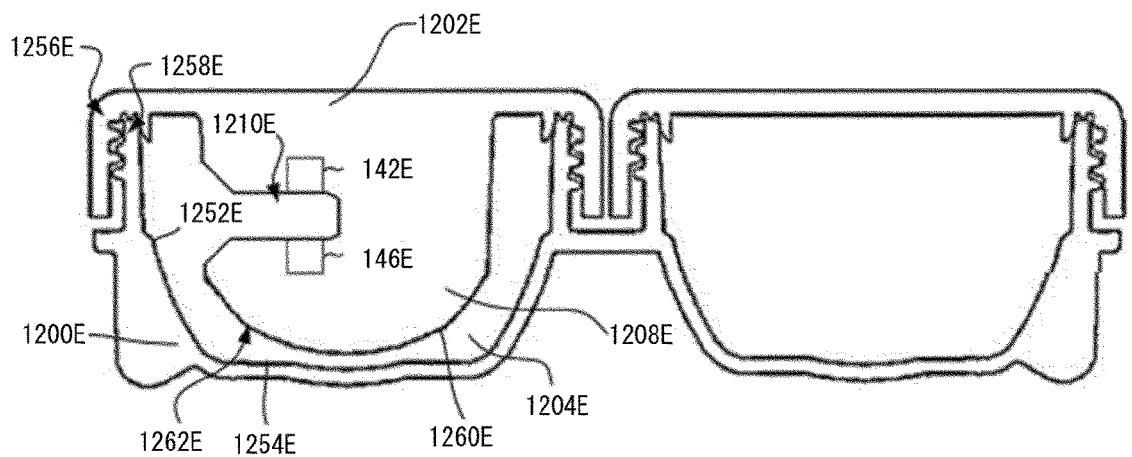

DETERMINATION SYSTEM, COMPUTING DEVICE, DETERMINATION METHOD, AND PROGRAM

BACKGROUND ART

When a user is wearing a contact lens, proteins, lipids, antibodies, and other types of biological materials from the user's tear fluid may be bonded to, adsorbed or deposited on the user's contact lens. In some cases, the bonding of proteins is a result of the protein denaturing, but in other situations the protein has not denatured before adsorbing to the contact lens. Protein deposits that are visible to the naked eye are most often a result of denaturation. These proteins can build up on the surface of the contact lenses forming protein deposits that impact the transparency of the lens and the integrity of the lens surface. In some cases, the protein deposits trigger an immune reaction and the body produces antibodies in response. These antibodies can cause inflammation, irritation, redness and itching in the eye.

Traditional approaches assessing patient health via tear fluid discuss specifically and structurally modifying a contact lens to collect information about the composition of the user's tears. U.S. Patent Publication No. 2014/0088381 issued to James Etzkorn, et al. teaches an apparatus, systems and methods that employ contact lenses to facilitate testing for an analyte present within tear fluid. According to Etzkorn, a contact lens can include a substrate that forms at least part of a body of the contact lens, and one or more cavities disposed within the substrate is configured to collect and store tear fluid over time when the contact lens is worn over an eye. Etzkorn also discloses a contact lens that includes a substrate that forms at least part of a body of the contact lens and one or more receptors disposed on or within the substrate, the one or more receptors being configured to bind to a known ligand.

In another reference, U.S. Patent Publication No. 2004/0181172 issued to Fiona Patricia Carney, et al., a contact lens is disclosed which can be used to collect one or more analytes of interest in a tear fluid, and in turn, determine the physiological state or health of an individual. Further, this reference teaches that a contact lens for collecting an analyte may be modified to have surface charges present in a density sufficient to impart to the contact lens an increased adsorption of the analyte of interest, a coating including a receptor which specifically binds the analyte of interest, molecular imprints for the analyte of interest, and a core material that is prepared from a composition containing a receptor which binds specifically the analyte of interest.

Further, U.S. Pat. No. 7,429,465 issued to Achim Muller, et al. teaches a process for analyzing an analyte in a hydrogel contact lens following its wear on the eye. The method includes physically or chemically inducing a volume reduction of the hydrogel contact lens and thereby squeezing the analyte out of the polymer material making up the contact lens and feeding the analyte obtained according to step (a) into an analyzer.

U.S. Pat. No. 6,060,256 issued to Dennis S. Everhart, et al. teaches an inexpensive and sensitive device and method for detecting and quantifying analytes present in a medium. The device includes a metalized film upon which is printed a specific, predetermined pattern of analyte-specific receptors. Upon attachment of a target analyte to select areas of the plastic film upon which the receptor is printed, diffraction of transmitted and/or reflected light occurs via the physical dimensions and defined, precise placement of the analyte. A diffraction image is produced which can be seen with the eye or, optionally, with a sensing device.

U.S. Patent Publication No. 2001/0034500 issued to Wayne Front March, et al. teaches an ophthalmic lens including a receptor moiety that can be used to determine the amount of an analyte in an ocular fluid. The receptor moiety can bind either a specific analyte or a detectably labeled competitor moiety. The amount of detectably labeled competitor moiety which is displaced from the receptor moiety by the analyte is measured and provides a means of determining analyte concentration in an ocular fluid, such as tears, aqueous humor, or interstitial fluid. The concentration of the analyte in the ocular fluid, in turn, indicates the concentration of the analyte in a fluid or tissue sample of the body, such as blood or intracellular fluid. Each of these references is incorporated by reference for all that they contain.

CITATION LIST

Patent Literature

PTL 1: U.S. Patent No. 2014/0088381

SUMMARY OF INVENTION

Technical Problem

According to the techniques disclosed in the above documents, a data source of the information used for testing for an analyte is limited to tear fluid, leachat, and aqueous humor, and therefore only a limited range of tests can be conducted.

Solution to Problem

In one embodiment of the present invention, a determination system comprises a computing device adapted to (i) obtain information relating to an eye of a target person from a plurality of data sources, and (ii) make a determination of a predetermined matter related to the target person based on at least part of the information, wherein the plurality of data sources including two or more of: a sensor included in a contact lens of the target person, a sensor included in a storage container of the contact lens, a measurement device which carries out measurement related to the eye of the target person, tear fluid of the target person, a storage solution of the contact lens, and a diagnostic process of the target person.

In other words, the invention relates in one aspect to a determination system, such as a lens recommendation system or a health ascertaining system, comprising a plurality of data sources, and a computing device adapted to obtaining information relating to an eye of a target person from the plurality of data sources, and making a determination of a predetermined matter related to the target person based on at least part of said information, wherein the plurality of data sources include two or more of a sensor included in a contact lens of the target person, a sensor included in a storage container of the contact lens, and/or a sensor included in a measurement device with use of which measurement has been carried out related to the eye of the target person, the tear fluid of the target person, and/or a storage solution of the contact lens of the target person, and/or a diagnostic process of the target person.

In a preferred embodiment of the determination system according to the present invention, the information from the plurality of data sources used for the determination comprises information relating to a biomarker derived from at least one of the contact lens, the tear fluid, and the storage solution.

In another preferred embodiment of the determination system according to the present invention, a contact lens including a sensor is comprised as at least one of the plurality of data sources, wherein the computing device makes the determination of the predetermined matter based on a/the biomarker detected by the sensor included in the contact lens.

In yet another preferred embodiment of the determination system according to the present invention, a storage container including the sensor is comprised as one of the plurality of data sources, wherein the computing device makes the determination of the predetermined matter based on the biomarker detected by the sensor included in the storage container.

Preferably in the preceding embodiment, the computing device makes the determination of the predetermined matter based on the biomarker detected by the sensor included in the storage container which contains the contact lens worn by the target person, and the biomarker detected in time series by the sensor included in the contact lens while the contact lens was worn by the target person.

In one preferred embodiment of the determination system according to the present invention, the computing device makes the determination of the predetermined matter based on the information obtained from the plurality of data sources, and information obtained by a mobile device of the target person.

In another preferred embodiment of the determination system according to the present invention, the information used for the determination of the predetermined matter comprises one or more characteristics obtained from a single data source of the plurality of data sources, preferably wherein the one or more characteristics are selected from the group comprising the concentration and/or type of at least one biomarker, location of the biomarker on a contact lens, chemometric data relating to at least one biomarker, more preferably ratio kinetics, peak, plateau, time constant and/or decay.

In a preferred embodiment of the determination system according to the present invention, the predetermined matter is a health condition of the target person, preferably wherein the health condition includes a blood sugar level, an intraocular pressure, an eye condition, an eye comfort level, a corneal strain level, a dry eye level, an allergic condition and/or an infection.

In another preferred embodiment of the determination system according to the present invention, the predetermined matter is an ophthalmic health condition of the target person, preferably wherein the ophthalmic health condition includes an intraocular pressure, an eye condition, an eye comfort level, a corneal strain level, a dry eye level, an allergic condition and/or an infection.

In yet another preferred embodiment of the determination system according to the present invention, the predetermined matter is what type of contact lens is recommendable to the target person.

In one preferred embodiment of the determination system according to the present invention, a/the information obtained from one or more of the plurality of data sources relates to one or more from the group comprising a protein and/or an antibody and/or an electrolyte level and/or a sodium level and/or a chloride level and/or a potassium level and/or a calcium level and/or an iron level and/or lysozyme level and/or a lactoferrin level and/or a lipocalin level and/or an albumin level and/or a cytokine level and/or an enzyme level and/or a lipid level and/or a proteases level and/or an immunoglobulin E level and/or an immunoglobulin G level and/or an immunoglobulin A level and/or an immunoglobulin M level.

In another aspect, the present invention relates to a computing device comprising a processor and a memory, wherein the processor obtains information related to an eye of a target person from a plurality of data sources, and makes a determination of a predetermined matter related to the target person based on at least part of the information, wherein the plurality of data sources include two or more of a sensor included in a contact lens of the target person, a sensor included in a storage container of the contact lens, and/or a sensor included in a measurement device with use of which measurement has been carried out related to the eye of the target person, the tear fluid of the target person, and/or a storage solution of the contact lens of the target person.

In a further aspect, the present invention relates to a determination method conducted by a computing device comprising the steps of obtaining information related to an eye of a target person from a plurality of data sources; and making a determination of a predetermined matter related to the target person based on at least part of the information, wherein the plurality of data sources include two or more of a sensor included in a contact lens of the target person, a sensor included in a storage container of the contact lens, and/or a sensor included in a measurement device with use of which measurement has been carried out related to the eye of the target person, the tear fluid of the target person, and/or a storage solution of the contact lens of the target person.

In a preferred embodiment of the preceding aspect of the present invention, the information obtained for making the determination of the predetermined matter comprises one or more characteristics obtained from a single data source of the plurality of data sources.

In one aspect, the present invention relates to a computer program comprising instructions which, when the program is executed by a computer, causes a computer to execute the steps of the determination method of the preceding aspect.

Advantageous Effects of Invention

According to one embodiment of the present invention, it is possible to make various determinations based on the plurality of data sources.

BRIEF DESCRIPTION OF DRAWINGS

The accompanying drawings illustrate various embodiments of the present apparatus and are a part of the specification. The illustrated embodiments are merely examples of the present apparatus and do not limit the scope thereof.

FIG. 6 illustrates a block diagram of an example of a database, in accordance with the present disclosure.

FIG. 18 depicts an example of a database.

FIG. 47 illustrates an example of a contact lens storage container.

FIG. 48 illustrates an example of a contact lens storage container.

Throughout the drawings, identical reference numbers designate similar, but not necessarily identical, elements.

DESCRIPTION OF EMBODIMENTS

Embodiment 1

Figure 1:
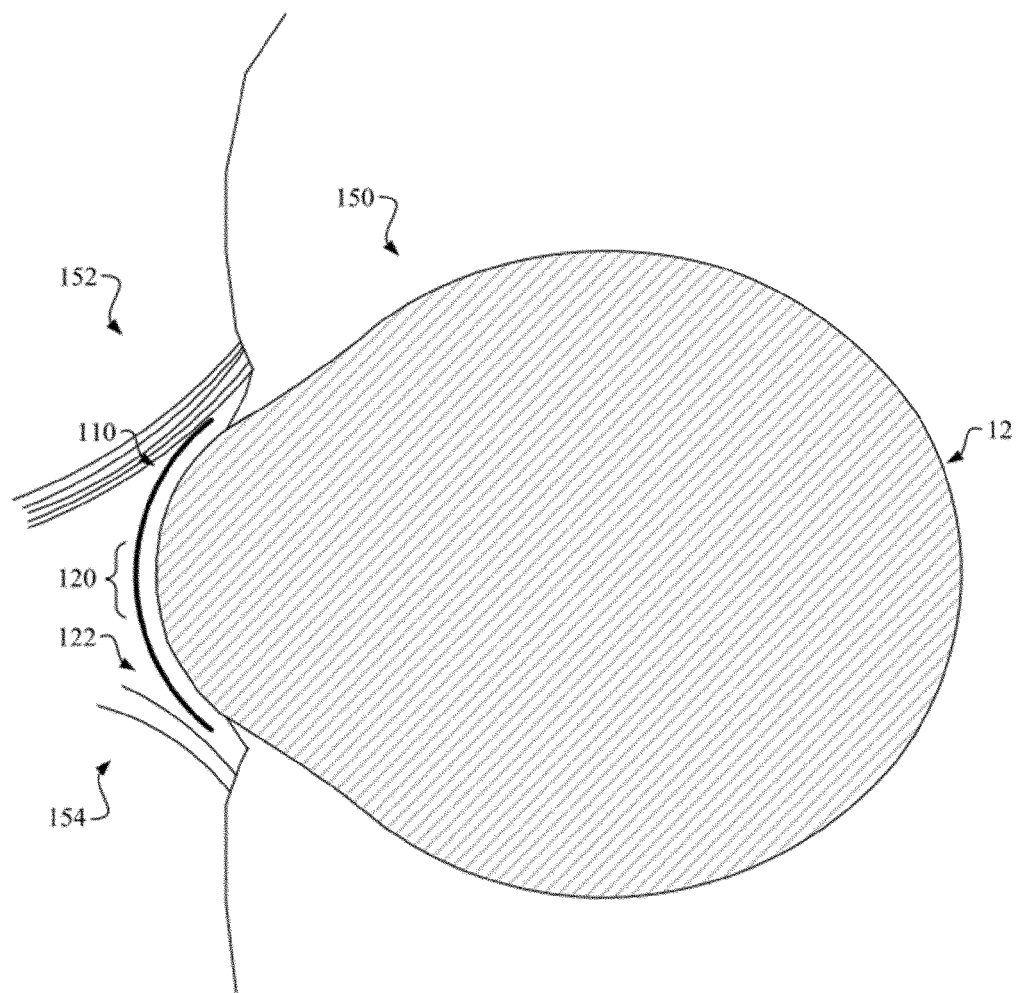
FIG. 1 illustrates an exemplary cross-sectional view of a contact lens positioned on an eye, in accordance with the present disclosure.

A healthy human eye is coated with tear fluid. Generally, the tear fluid includes a base mucous layer that coats the cornea of the eye, an aqueous layer, and a lipid layer that protects the aqueous layer by forming an outer hydrophobic barrier that helps to retain the aqueous layer against the mucous layer. The aqueous layer includes metabolites, proteins, electrolytes, and other constituents. The make-up of the tear fluid may result, in part, from a physiological response to an illness or an allergy. In some cases, the make-up of the tear fluid can represent the physiological expression of an individual's unique DNA.

The principles disclosed herein include a method of using the constituents of the tear fluid as biomarkers that can be analyzed to determine a health condition of a user. These biomarkers may be collected on a contact lens worn by the user. Any appropriate type of contact lens can be used to collect the biomarkers. However, unaltered commercially available contact lenses from a wide variety of manufacturers for corrective vision are envisioned to be the contact lens that are used to collect the biomarkers. Biomarkers, such as proteins, generally start to bind to these contact lenses as soon as the contact lenses are placed over the user's eye. Without modifying the contact lens as they are provided by the manufacturers, the contact lens may bind to these proteins, electrolytes, and/or other biomarkers in the tear fluid.

Generally, a user removes the contact lenses after wearing them for a period of time. Often, before the user retires to bed, the user removes the contact lens and places the contact lens in a storage case for the night. The storage case may include a storage solution that disinfects the contact lens and also breaks down the build-up on the contact lens. The storage solution may be an aqueous solution that causes the build-up on the contact lens to dissolve into the solution. After a period of time, the storage solution may be replaced with fresh storage solution to reduce the concentration of tear fluid constituents in the fluid.

The storage solution may be analyzed to determine the type and/or concentration of biomarkers that dissolved off of the contact lens. In some cases, the solution may be analyzed without the contact lens in the solution. In other examples, the contact lens is removed from the solution before analyzing the biomarkers.

Any appropriate type of sensor may be used to identify the type, concentration, and/or characteristics of the biomarkers. In some instances, the sensor is incorporated into the contact lenses' storage container. In this example, the sensor may be an optical spectral analyzer that passes light through the cavity of the storage container holding the storage solution from a light source to a light receiver. The receiver may measure the amount the light's optical transmittance through the storage solution. In some cases, the spectral analyzer passes light through the storage solution at isolated predetermined wavelengths and measures the optical transmittance at each of the predetermined wavelength ranges. Each of the recorded transmittances may correlate to the presence of specific kinds of biomarkers and their concentrations. In this case, the storage container may comprise the sensor, a processor, and a memory. And the sensor may obtain information which indicates a characteristic of at least one biomarker which is derived from a contact lens used by a user and stored in the storage container, and the processor may send the information to a computing device which ascertains a health condition of the user based on the information.

In other examples, the sensor is incorporated into a hand-held device. In one case, the sensor may be incorporated into the user's mobile device, such as a smart phone and/or electric tablet. In one of these types of examples, the user may direct a beam of light into the storage solution and measure a reflection.

In some cases, the measurements may be augmented with complementary information, such as an amount of time that the user wore the contact lens. For example, the user may interact with a user interface to the sensor (technically sensing device including the sensor) to input how long the user wore the contact lenses. In some cases, the user may be requested to input the number of hours that the user wore the contact lens. In other examples, the user may be requested to input the number of days that he or she wore the contact lenses, whether the user removed the contact lenses during the night, the time of when the storage solution was last replaced, other factors that may affect the concentration of biomarkers in the storage solution, or combinations thereof.

In some examples, the sensor may record the measurements to determine a measurement level of each of the desired biomarkers. The measurement level is a numerical value indicative of a measurement value range of each biomarker. In some examples, the sensor may record the measurements in real time. Further, the sensor may include local and/or cloud based logic to determine the type, concentration, and/or other characteristics of the varying kinds of biomarkers. In some cases, the sensor (technically sensing device including the sensor) may use learning algorithms, predictive models, data correlation models, clustering models, any other appropriate computational techniques, and combinations thereof. In some cases, the sensor (technically sensing device including the sensor) may include a database that stores the correlation between the identification/concentration of the biomarkers and a health condition of the user.

The measurements may be sent to a computing device that processes the information retrieved from the sensor. In some cases, at least some computations are performed by the sensor (technically sensing device including the sensor) before sending data to a computing device where the computations are finished. In other examples, the sensor sends raw data to the computing device. In this example, all data processing, including data cleaning, data management, data mining, and any application specific issues, is performed remotely to the sensor.

The determinations of the type of biomarkers, the characteristics of biomarkers, such as the concentration of the biomarkers, chemometric data such as ratio kinetics, peak, plateau, time constant, decay, and so forth may be compared to data points stored in a database. The database may be local to the computing device or the computing device may have remote access to the database. The data in the database may correlate the different types and concentrations of biomarkers with health conditions, such as eye health conditions, allergic conditions, other physiological conditions, or combinations thereof. In some examples, the data in the database may be used as input or training data to implement supervise machine learning techniques, or other statistical learning approaches to solve prediction inference, or other data mining problems related to health conditions, such as eye health conditions, allergic conditions, other physiological conditions, or combinations thereof. The database may correlate the measurement levels of the biomarkers to the health conditions in subcategories base on at least one population demographic.

In some cases, the database is in communication with multiple users and data sources. As data regarding the storage solution of a user is collected, data from each of the users may contribute to the information in the database. In some cases, data collection may automatically launch a data management system of the database. In some examples, the data management system or another process may incorporate additional data into the database, such as the health conditions of each of the users. As result, the correlations in the database may be built from reports from the users. The computing device may update the database based on the reports from the users. In some examples, patient data may be used as predictors in a statistical machine learning process. In some cases where the database is built using thousands of users, the database's input may identify correlations between health conditions and specific levels of different types of biomarkers that are unknown to the scientific community. Thus, even before scientific studies may be conducted to find a correlation between a biomarker and a health condition, the computing device may, with reference to the database, send information related to the diagnosis of a disease, a disease severity assessment, a risk stratification, a therapeutic decision or request, a recommendation to the user to be tested for a specific type of condition, or combinations thereof.

These principles allow a super multivariate database to be built that correlates the health conditions of the users with varying parameters of the biomarkers. For example, the database may include supplementary user data such as age, gender, weight, height, and the like. These principles also allow the user to have a non-invasive procedure to measure the biomarkers. Further, in those cases where the user is already storing and cleaning his or her contact lens from time to time, the user may incur little to no additional effort to measure the biomarkers and receive reports on at least some of his or her health conditions.

Referring now to the figures, FIG. 1 depicts an example of a contact lens 110 situated on the outside of a human eye 150. The contact lens 110 spans an outside surface of the exposed portion of the eye 150. An upper portion of the contact lens 110 is adjacent a set of eyelashes 152 of the upper eye lid. The contact lens 110 may include a posterior side that is in contact with the cornea of the eye 150, and an anterior side that is opposite of the posterior side. As the lid travels over the eye 150, the eye lid moves across the anterior side of the contact lens 110.

A user may wear the contact lens for vision correction purposes. In this type of example, the contact lens may include an optic zone 120 and a peripheral zone 122. The optic zone 120 may include a region that focuses light to the center of the user's retina 12. The peripheral zone 122 may contact the eye near or over the sclera. While this example discloses using a commercially available contact lenses configured for vision correction to be worn on the eye, other types of contact lenses may be used in accordance with the principles described in the present disclosure. For example, the contact lens may not include a curvature or other features that correct vision.

The contact lens 110 may be soft contact lenses, rigid gas permeable (RGP) contact lenses, orthokeratology contact lens, another type of contact lenses, or combinations thereof. The contact lens may be made of any appropriate type of material. A non-exhaustive list of materials that may be used to construct the contact lens include any appropriate silicone material and/or hydrogel material. Such material may be formed of polymers, such as tefilcon, tetrafilcon A, crofilcon, helfilcon A&B, mafilcon, polymacon, hioxifilcon B, lotrafilcon A, lotrafilcon B, galyfilcon A, senofilcon A, sifilcon A, comfilcon A, enfilcon A, lidofilcon B, surfilcon A, lidofilcon A, alfafilcon A, omafilcon A, vasurfilcon A, hioxifilcon A, hioxifilcon D, nelfilcon A, hilafilcon A, acofilcon A, bufilcon A, deltafilcon A, phemfilcon A, bufilcon A, perfilcon, etafilcon A, focofilcon A, ocufilcon B, ocufilcon C, ocufilcon D ocufilcon E, ocufilcon F, phemfilcon A, methafilcon A, methafilcon B, vilfilcon A, other types of polymers, monomers, or combinations thereof. These materials may include various combinations of monomers, polymers, and other materials to form the material that makes up the contact lens.

In one embodiment, the contact lens material is made of hydrogel polymers without any silicone. This may be desirable to increase the wettability of the contact lens. In another embodiment, the contact lens material is made of silicone hydrogel material.

The tear fluid in the ocular cavity may come into contact with the contact lens. In some examples, the entire surface area of the contact lens comes into contact with the tear fluid. The constituents of the tear fluid may include lipids, electrolytes, metabolites, proteins, antibodies, other types of compounds, or combinations thereof. These constituents may be biomarkers that can be indicative of a health condition of the user. The biomarkers may bind to the contact lens.

A non-exhaustive list of biomarkers from the tear fluid that may be of interest includes, but is not limited to, electrolytes, sodium, potassium, chloride, phenylalanine, uric acid, galactose, glucose, cysteine, homocysteine, calcium, ethanol, acetylcholine and acetylcholine analogs, ornithine, blood urea nitrogen, creatinine, metallic elements, iron, copper, magnesium, polypeptide hormones, thyroid stimulating hormone, growth hormone, insulin, luteinizing hormones, chorionogonadotrophic hormone, obesity hormones, leptin, serotonin, medications, dilantin, phenobarbital, propranolol, cocaine, heroin, ketamine, hormones, thyroid hormones, ACTH, estrogen, cortisol, progesterone, histamine, IgE, cytokines, lipids, cholesterol, apolipoprotein A1, proteins and enzymes, lactoferrin, lysozyme, tear-specific prealbumin or lipocalin, albumin, complement, coagulation factors, liver function enzymes, heart damage enzymes, ferritin, virus components, immunoglobulins such as IgM, IgG, proteases, protease inhibitors, lactate, ketone bodies, other types of biomarkers, or combinations thereof.

In some cases, commercially available contact lenses may have surface properties to allow the biomarkers to bind to the contact lens without any modifications. Conventionally, protein build-ups and other types of build-ups on contact lens are considered a problem on regular contact lens that do not have surface modifications to enhance a biomarker's ability to bind to the contact lens. In other examples, the contact lens may be modified to enhance the binding ability of the biomarkers or just for specific biomarkers. In those cases where the surface of the contact lens may be modified to enhance an ability to bind to the biomarkers, the binding enhancements may be made to any appropriate location on the contact lens, including, but not limited to, the peripheral zone, the optical zone, the anterior side of the contact lens, the posterior side of the contact lens, other areas of the contact lens, or combinations thereof.

Figure 2:
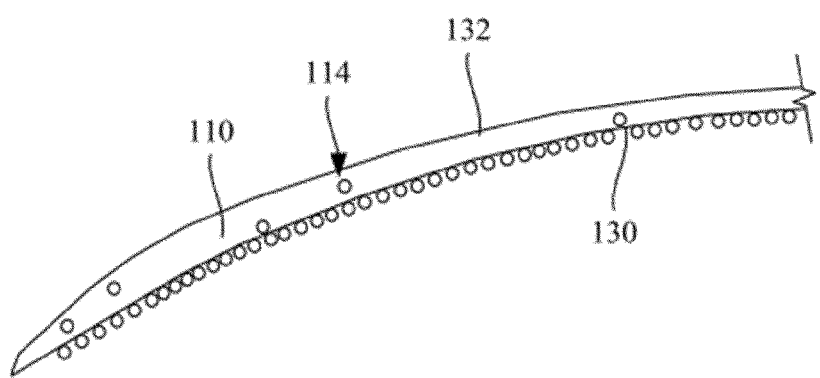
FIG. 2 illustrates an exemplary cross-sectional view of biomarkers adhered to a contact lens, in accordance with the present disclosure.

FIG. 2 depicts an example of biomarkers 114 attached to the posterior surface 130 of the contact lens. While this example depicts the biomarkers 114 attached to the posterior surface 130 of the contact lens, the biomarkers 114 may be attached to just the anterior surface 132 or to both the anterior surface 132 and posterior surface 130 of the contact lens 110. In some cases, the biomarkers 114 may be adsorbed, absorbed, bonded, covalently bonded, ionically bonded, adhered, cohered, or otherwise connected to a surface of the contact lens 110. In some cases, the biomarkers 114 are incorporated into the thickness of the contact lens 110.

When the contact lens 110 is removed from the user's eye, the biomarkers 114 may stay with the contact lens 110 as depicted in FIG. 2. The amount of biomarkers 114 that are attached to the contact lens 110 may be related to the amount of time that the contact lens 110 was on the eye. In some cases, the contact lens 110 may be worn by the user during that day and removed at nighttime. Under these circumstances, biomarkers 114 may cover a substantial amount of the contact lens' surface area. However, in other examples, the contact lens 110 may be worn by the user for a smaller period of time. In one specific instance, a patient may be provided with a contact lens 110 for a period of minutes in a doctor's office to collect biomarkers 114 for analysis. In other examples, a patient may be instructed to keep a contact lens 110 in for a matter of hours or even longer than a day to collect the desired about of biomarkers 114.

Figure 3:
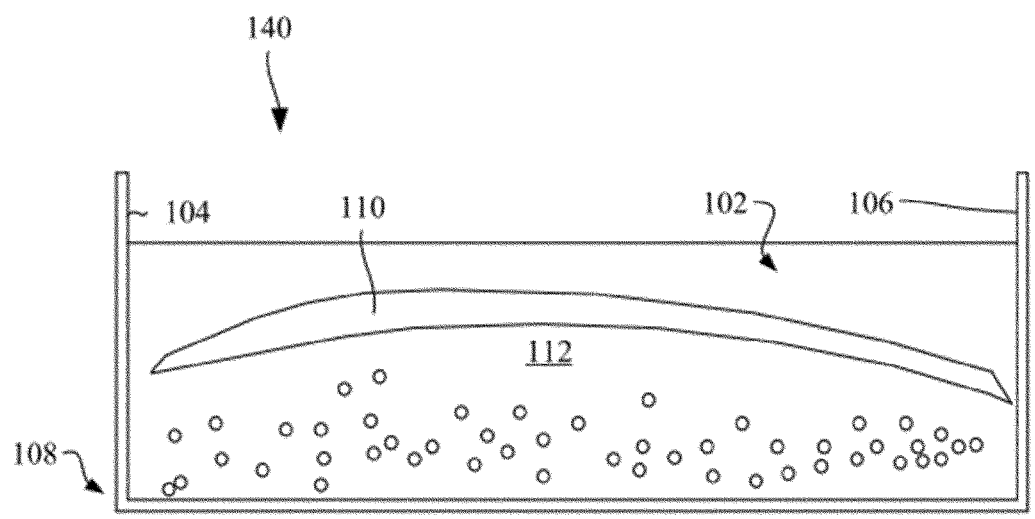
FIG. 3 illustrates an exemplary cross-sectional view of a contact lens in solution, in accordance with the present disclosure.

FIG. 3 depicts an example of a contact lens 110 in a storage container 140 with an internal cavity 102. The cavity 102 is defined by a first wall 104 and a second wall 106 that are connected together at the walls' ends 108. A contact lens 110 and a solution 112 are also disposed within the cavity.

The solution 112 may include a cleansing agent, such as a hydrogen peroxide or another type of agent to clean the contact lens and kill bacteria, fungus, other types of germs, or combinations thereof. The solution 112 may be an off-the-shelf type of storage solution that hydrates and cleans the contact lens. The storage solution 112 may cause the biomarkers 114 to dissolve into the solution 112 thereby cleaning the contact lens 110. The contact lens 110 stays in the storage solution 112 until the contact lens 110 is later retrieved by the user for wearing. In some cases, the contact lens 110 is immersed into the solution for a short period of time, such as a couple of minutes. In other examples, the contact lens 110 may remain in the solution for multiple hours, such as overnight. With the biomarkers 114 removed from the contact lens 110, the biomarkers 114 are in the solution 112 where the biomarker types and their respective concentrations can be analyzed.

The biomarkers 114 may be removed from the contact lens 110 without adversely affecting the contact lens 110. In those examples, the contact lens 110 may be re-worn by the user. In some cases, the contact lens 110 is removed from the solution 112 so that the contact lens 110 is not affected by the testing mechanism performed on the solution. In other examples, the contact lens 110 remains in the solution 112 while the solution 112 is analyzed, but the analysis does not adversely affect the contact lens 110 so that the contact lens 110 can be re-worn by the user.

In some examples, the biomarkers 114 can be analyzed in the storage container 140. In other examples, the solution 112 may be transferred to another type of device with a sensor for taking the measurements. In yet another example, a hand-held device may incorporate a sensor that can perform the analysis on the solution.

Figure 4:
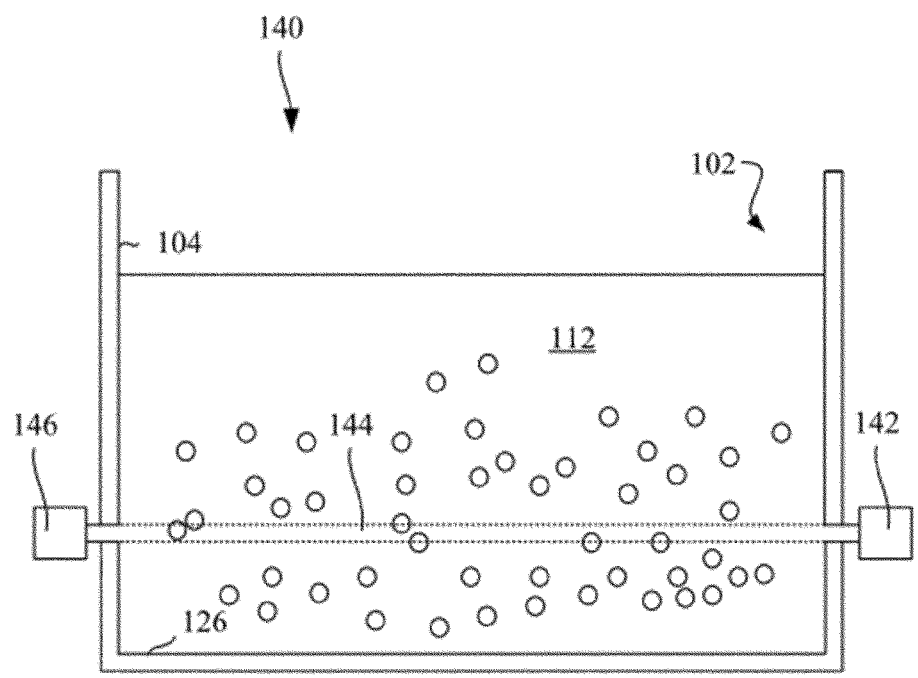
FIG. 4 illustrates an exemplary cross-sectional view of running a test on the solution containing biomarkers from a contact lens, in accordance with the present disclosure.

One type of approach of analyzing the solution is depicted in FIG. 4. In this example, an optical spectral analyzer is a type of sensor that is incorporated into the storage solution container 140. In the example of FIG. 4, a storage container 140 for a contact lens 110 includes a cavity 102 that is defined by at least one wall 104 that is connected by a floor 126. In some cases, a single circular wall defines at least a portion of the cavity 102. In other examples, multiple independent walls are joined together to define the cavity 102.

A light source 142 is incorporated into a first side of the cavity. The light source 142 may be oriented to direct a beam 144 of light through the solution 112 to a light receiver 146. As the beam 144 of light is transmitted through the solution 112, a portion of the light is absorbed by the solution, depending on its contents. A solution 112 with a different type of biomarker 114 may have a different light transmittance through the solution 112. Further, a solution 112 with a different concentration of the same biomarker 114 may also exhibit a different light transmittance.

In some cases, the light source 142 may have an ability to isolate a range of wavelengths to be transmitted independently through the solution 112. The transmittance for each wavelength may be measured. Certain biomarkers in the solution 112 may not affect the optical transmittance at a first wavelength, but may affect the optical transmittance at a second wavelength. Thus, by transmitting light at different wavelengths, a more refined measurement of the solution's composition can be measured. The measured transmittances at each wavelength can be compared to other solutions with known types and known amounts of biomarkers. Thus, the measured transmittance levels can be correlated to the types and concentration of the biomarkers 114 in the solution 112.

Other types of spectroscopic methods can be used to identify the types and concentration of the biomarkers in the solution. In some cases, measuring a frequency rather than a wavelength may be performed by the spectral analyzer. A non-exhaustive list of other types of spectroscopic mechanisms for analyzing the solution may include atomic absorption spectroscopy, attenuated total reflectance spectroscopy, electron paramagnetic spectroscopy, electron spectroscopy, Fourier transform spectroscopy, gamma-ray spectroscopy, infrared spectroscopy, laser spectroscopy, mass spectrometry multiplex or frequency-modulated spectroscopy, Raman spectroscopy, and x-ray spectroscopy.

While the example of FIG. 4 includes the light source 142 and the light receiver 146 on different sides of the cavity walls, the light source 142 and the light receiver 146 may be on the same side of the cavity 102. In such an example, the light source 142 may cause a reflection of the light that was emitted from the light source 142 with the light receiver 146.

Figure 7:
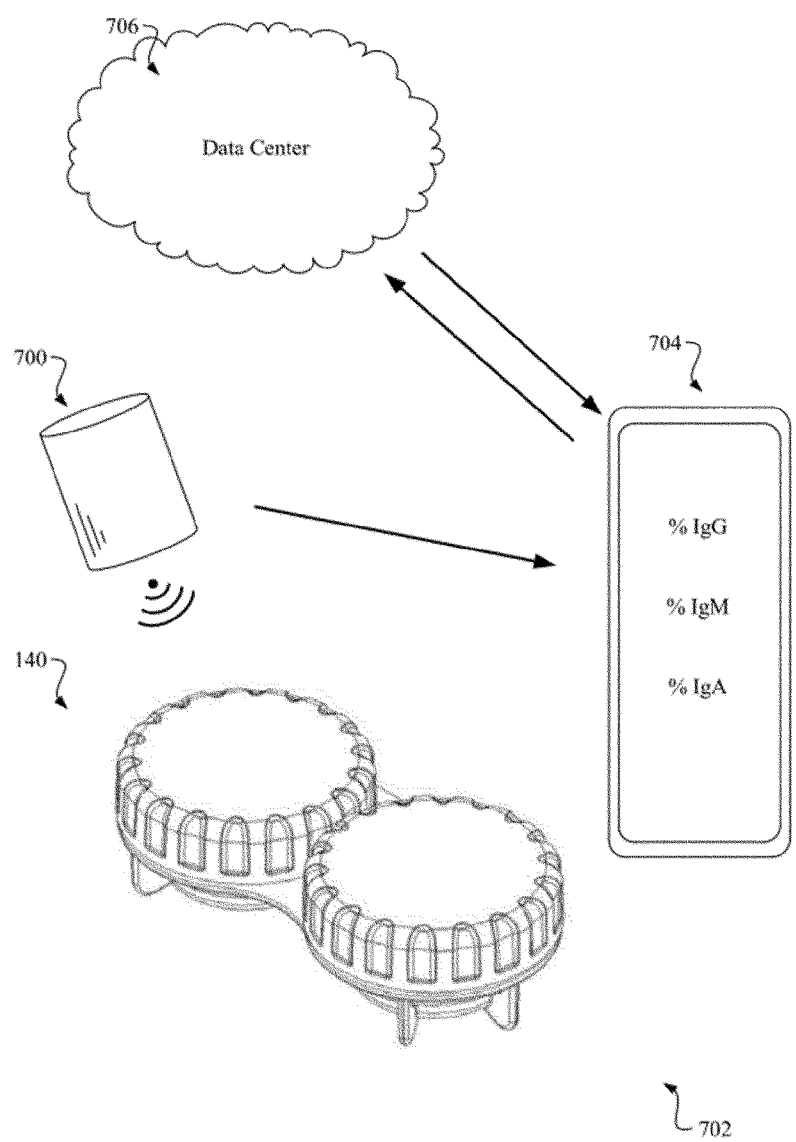
FIG. 7 illustrates a cross-sectional view of an example of a health condition system, in accordance with the present disclosure.

In some examples, the sensor may be part of a hand-held device 700 depicted in FIG. 7. In this example, the hand-held device includes a sensor, such as an infrared spectrometer, that can measure a concentration of a biomarker within the solution. For example, the hand-held device may include an end that has an infrared source that sends infrared light into the solution when the user orients the hand-held device to appropriately direct the infrared light and instructs the hand-held device to send the light. The amount of the infrared light that is absorbed into the solution may be based, at least in part, on the concentration of the biomarker in the solution. Thus, the returning amount of the infrared light to the hand-held device may be measured with an infrared receiver incorporated into the hand-held device.

In yet other examples, the solution may be poured into another device for analysis. In one case, the solution may be poured into an immunodiffusion machine, a centrifuge, another type of device, or combinations thereof for measuring at least one property of the solution.

Figure 5:
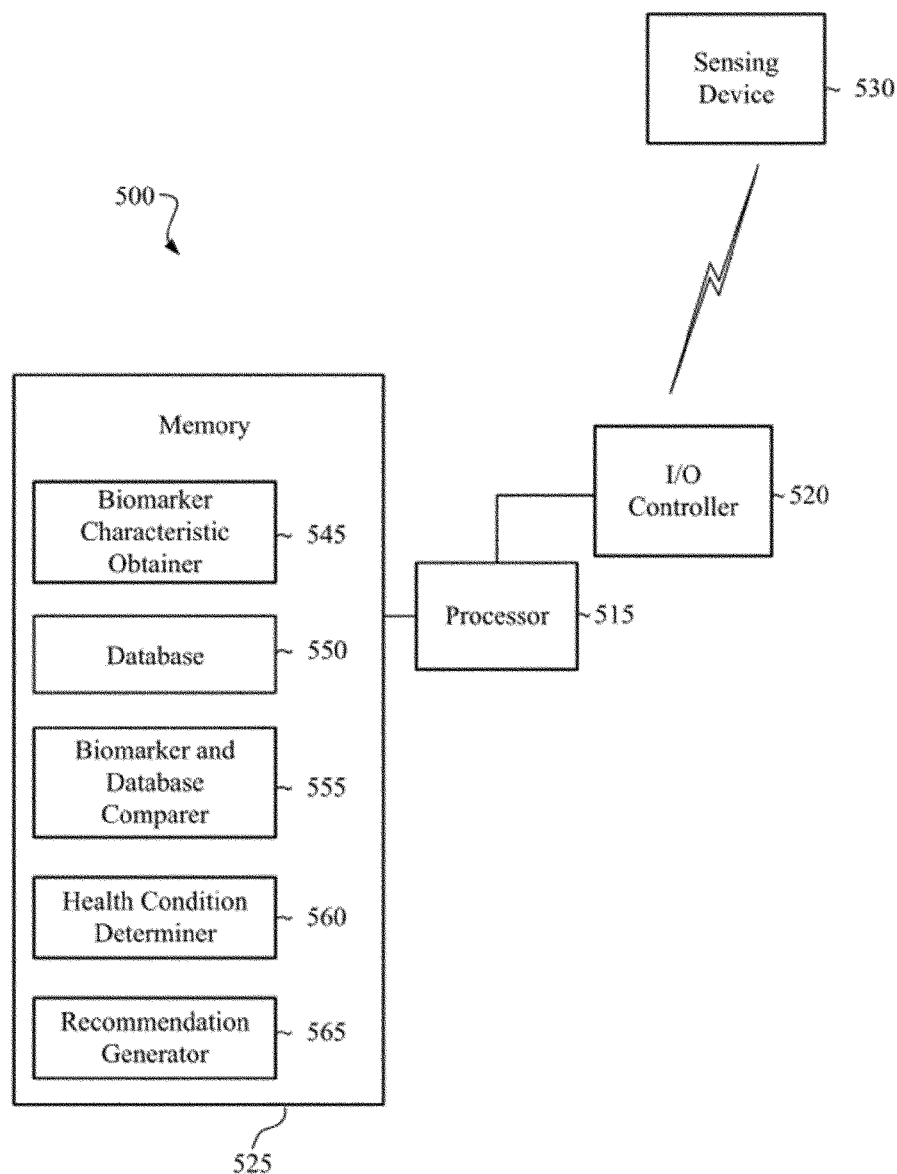
FIG. 5 illustrates a block diagram of an example of a health condition system, in accordance with the present disclosure.

FIG. 5 depicts a diagram of a health condition system 500. The system 500 includes a processor 515, an I/O controller 520, and memory 525. The processor 515 and the memory 525 are components of the computing device. The I/O controller 520 may be in communication with a sensing device 530. In some examples, a sensor of the sensing device 530 is incorporated into the contact lens storage case, into a hand-held device, an independent machine configured to analyze the solution, another type of sensor, or combinations thereof. In some examples, the sensing device may include its own processor, memory, and/or transponder. The components of the system and the sensing device 530 may communicate wirelessly, through hard wired connections, or combinations thereof. The memory 525 of the system may include a biomarker characteristic obtainer 545, a database 550, a biomarker and database comparer 555, a health condition determiner 560, and a recommendation generator 565. In some examples, the system 500 may further include a base station in communication with the processor 515, the base station in communication with the sensing device 530, for example via the transponder.

The processor 515 may include an intelligent hardware device, (e.g., a general-purpose processor, a digital signal processor (DSP), a central processing unit (CPU), a microcontroller, an application-specific integrated circuit (ASIC), a field-programmable gate array (FPGA), a programmable logic device, a discrete gate or transistor logic component, a discrete hardware component, or any combination thereof). In some cases, the processor 515 may be configured to operate a memory array using a memory controller. In other cases, a memory controller may be integrated into the processor 515. The processor 515 may be configured to execute computer-readable instructions stored in a memory to perform various functions (e.g., functions or tasks supporting the evaluation of prescribed optical devices).

The I/O controller 520 may represent or interact with a modem, a keyboard, a mouse, a touchscreen, or a similar device. In some cases, the I/O controller 520 may be implemented as part of the processor. In some cases, a user may interact with the system via the I/O controller 520 or via hardware components controlled by the I/O controller 520. The I/O controller 520 may be in communication with any appropriate input and any appropriate output.

The memory 525 may include random access memory (RAM) and read only memory (ROM). The memory 525 may store computer-readable, computer-executable software including instructions that, when executed, cause the processor 515 to perform various functions described herein. In some cases, the memory 525 may contain, among other things, a basic input/output system (BIOS) which may control basic hardware and/or software operation such as the interaction with peripheral components or devices. The memory 525 storing the software (that is, a program) can be referred to as a "computer readable recording medium". The recording medium can be a "non-transitory tangible medium" such as, for example, a tape, a disk, a card, a semiconductor memory, a programmable logic circuit, or the like. The program can be supplied to the computer via any transmission medium (such as a communication network or a broadcast wave) that can transmit the program. The present invention can also be achieved in the form of a computer data signal in which the various programs are embodied via electronic transmission and which is embedded in a carrier wave.

The biomarker characteristic obtainer 545 represents programmed instructions that cause the processor 515 to obtain a characteristic of the biomarker from the solution. In other words, the processor 515 executes the programmed instructions to function as the biomarker characteristic obtainer 545. The characteristic may include a biomarker identification, a biomarker concentration, another type of characteristic, or combinations thereof. In some examples, the biomarker characteristic obtainer passively receives a signal containing information about the characteristic. In other examples, the biomarker characteristic obtainer actively requests information about the biomarker.

The database 550 represents a data structure that holds information about characteristics of the biomarkers. The database 550 may be filled with information about the characteristics that have been measured in labs, for example by chemometric methods, obtained from at least one user, or combinations thereof. In some examples, the database is initially populated with information from patients and/or users who have known health conditions and the biomarkers types and concentration levels in the tear fluid have been studied in labs or in other settings. Since some users with the same health condition may exhibit slightly different types and level concentrations of biomarkers, the information from many users may be compiled. In some examples, thousands or even millions of samples may be collected.

The biomarker and database comparer 555 represent programmed instructions that cause the processor 515 to compare the obtained biomarker characteristic against the information stored in the database. In other words, the processor 515 executes the programmed instructions to function as the biomarker and database comparer 555. In some examples, the programmed instructions may include data mining algorithms to compare biomarker characteristics. The health condition determiner 560 represents programmed instructions that cause the processor 515 to determine the health condition correlated with similar characteristics stored in the database is a health condition of the user. In other words, the processor 515 executes the programmed instructions to function as the health condition determiner 560.

Correlations between certain biomarkers and their respective concentrations may go unobserved on one-on-one analysis with each of the patients. However, with such a large sample size, correlations that have been previously unobserved may be detected, for example via data mining techniques used by the system 500. For example, an analysis may be run on all the biomarker characteristics of users with a specific health conditions. Such an analysis may reveal that a certain biomarkers that had not previously been linked to that health condition has a statistically significant normal concentration level, a statistically significant low concentration level, a statistically significant high concentration level, another statistically significant concentration level, a statistically insignificant type of concentration level, or combinations thereof that had not previously been observed. These correlations may help identify health conditions that may go otherwise unobserved in a patient. Even in those events where the user's health condition may be eventually diagnosed properly, comparing the obtained biomarker characteristics with the information stored in the database may result in a quicker diagnosis.

The recommendation generator 565 represents programmed instructions that cause the processor 515 to generate a recommendation to the user. In other words, the processor 515 executes the programmed instructions to function as the recommendation generator 565. The recommendation may include having a confirmation test to confirm whether or not the user has that determined health condition. The test may be conducted by a device that used by the user (for example, a mobile device). In those cases where a confirmation test is conducted, the results of the confirmation test may be sent to the computing device. The results may be used to assist the database and its associated analytics to improve the health condition determinations.

Another recommendation may be to receive treatment for the determined health condition. Another recommendation may be to visit a specific type of doctor. Another recommendation may include avoiding certain types of foods. Yet, another recommendation may include a health regime, a particular type of diet, another recommendation to perform a type of action, or combinations thereof.

FIG. 6 depicts an example of a database 600 that associates a characteristic of the tear chemistry, potential indications, and possible causes of the tear chemistry. In this example, the database 600 includes a first column 602 that represents the tear chemistry, a second column 604 that represents the potential indications, and a third column 606 that represents the possible causes of the tear chemistry. The database 600 may include a first row 608 that includes the correlation for a tear chemistry with a normal lactorferrin level and a normal IgE level, a second row 610 that includes the correlation for a tear chemistry with a normal lactorferrin level and a high IgE level, a third row 612 that includes the correlation for a tear chemistry with a low lactorferrin level and a normal IgE level, a fourth row 614 that includes the correlation for a tear chemistry with a low lactorferrin level, a fifth row 616 that includes the correlation for a tear chemistry with a high lactorferrin level, and a sixth row 618 that includes the correlation for a tear chemistry with a high IgE level.

While the example of FIG. 6 depicts an example with the correlations of specific types of biomarkers, any appropriate type of correlation may be included in the database. In some instances, the characteristics correlated with a single biomarker may be included as depicted in rows 614, 616, 618. In other instances, the characteristics correlated with a specific set of biomarkers may be included. For example, the health conditions correlated with two or more characteristics of different types of biomarkers may be included as depicted in rows 608, 610, 612. Any appropriate number of biomarker characteristics may be included. For example, anywhere from one, three, to hundreds of characteristics may be collectively correlated to a specific type of health condition. Further, while the example of FIG. 6 includes specific types of biomarkers, the database may include any appropriate type of biomarker correlations. In the example shown in FIG. 6, whether a biomarker level is "Normal", "Low", or "High" can be determined by comparing the measurement value of the biomarker with a pre-determined threshold.

FIG. 7 depicts an example of a system 702 of determining the health condition of a user. In this example, a storage solution may be contained within a contact lens container 140. A hand-held device 700 with a sensor may be used to take a measurement of at least one characteristic of the biomarkers in the solution. The hand-held device 700 may send the recorded levels to a mobile device 704 (computing device) that is in communication with a cloud based data center 706 that stores the database (FIG. 6, 600). The mobile device 704 may relay the recorded levels to the database in the data center 706, which may send the correlations back to the mobile device 704. The mobile device 704 may present the results from the hand-held device and/or the correlations from the database in a user-interface of the mobile device 704.

At least some of the processing of the measurements obtained from the return signals from the storage solution may occur at the hand-held device 700, the mobile device 704, and/or the data center 706. In some examples, the mobile device 704 includes a program that retrieves the correlations from the database and performs additional tasks. For example, the mobile device 704 may retrieve information about the health condition from another source other than the database in response to receiving the health condition from the database. Another additional task that the mobile device 704 may perform in response to receiving the health condition is to retrieve a health professional's contact information, consult a user's calendar to set up an appointment with the health professional, schedule an appointment with the health professional, perform another task, or combinations thereof.

Figure 8:
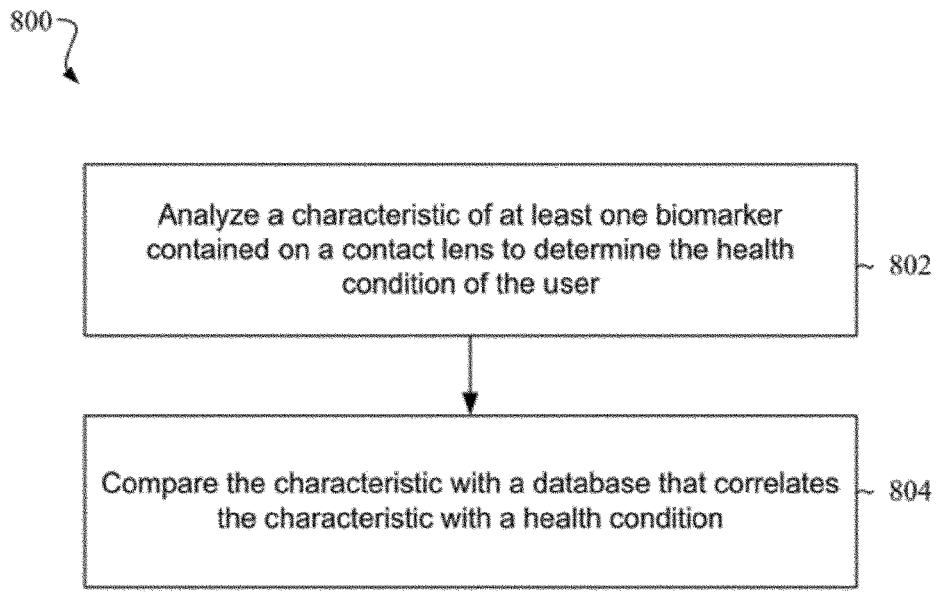
FIG. 8 illustrates a block diagram of a method of an example of determining a health condition, in accordance with the present disclosure.

FIG. 8 illustrates an example of a method 800 of determining a health condition. In this example, the method 800 includes analyzing 802 a characteristic of at least one biomarker contained on a contact lens to determine the health condition of the user and comparing 804 the characteristic with a database that correlates the characteristic with a health condition.

At block 802, a characteristic of at least one biomarker is analyzed. This process may be performed by the sensing device 530 or be performed by the processor 515 (specifically, the biomarker characteristic obtainer 545, for example) after the processor 515 obtains the measurements of the sensor from the sensing device 530. The biomarkers can be obtained from a contact lens. In some cases, the biomarkers remain on the contact lens when the biomarkers are being analyzed. In other examples, the biomarkers are removed from the contact lens before the analysis. The characteristic may include a type of biomarker, a concentration of biomarker, a location of the biomarker on the contact lens, another type of characteristic, or combinations thereof. The characteristic may involve a single biomarker. In other examples, the characteristic includes the collective condition of multiple biomarkers.

At block 804, the characteristic may be compared to a database (for example, the database 550 in FIG. 5) that correlates the characteristic with the health condition. This process is performed by the processor 515 (specifically, the biomarker and database comparer 555). For example, the database may include the type and concentration of a single biomarker that is correlated with a specific health condition. In another example, the database may correlate that when a first type of biomarker has a specific concentration and a second type of biomarker has different specific concentration that is associated with a specific type of health condition.

Figure 9:
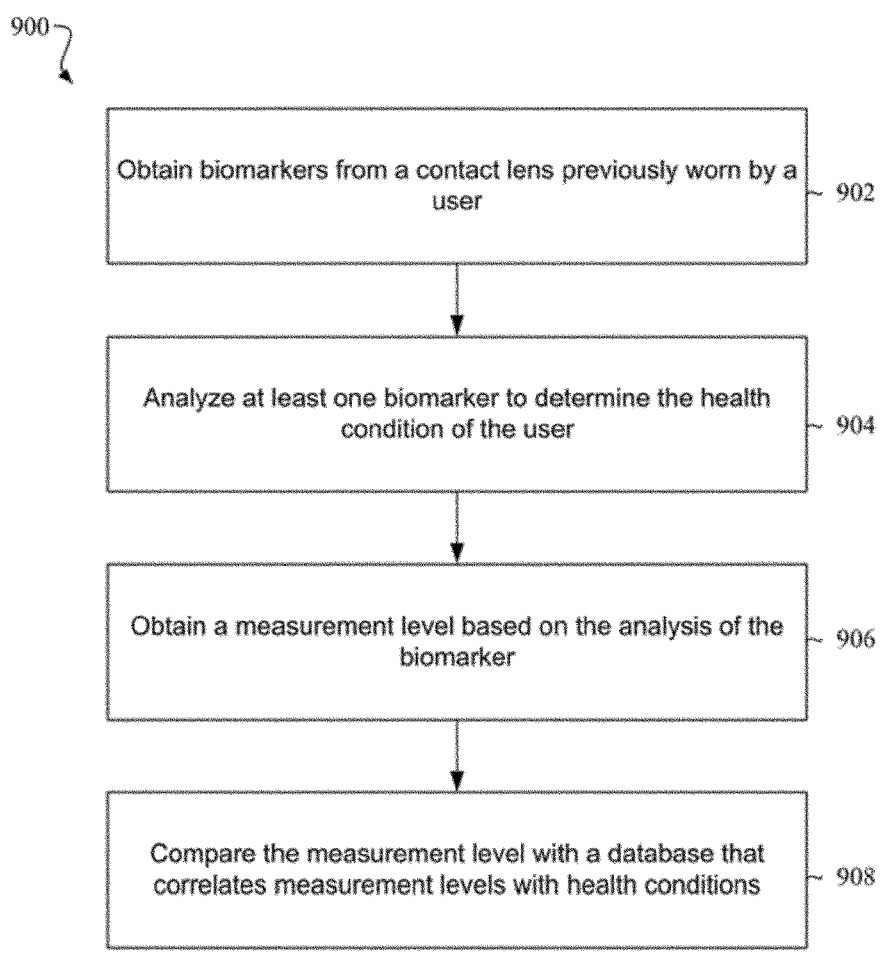
FIG. 9 illustrates a block diagram of a method of an example of determining a health condition, in accordance with the present disclosure.

FIG. 9 illustrates an example of a method 900 of determining a health condition. In this example, the method 900 includes obtaining 902 biomarkers from a contact lens previously worn by a user, analyzing 904 at least one biomarker to determine the health condition of the user, obtaining 906 a measurement level based on the analysis of the biomarker, and comparing 908 the measurement level with a database that correlates measurement levels with health conditions. The process blocks 904 and 906 are performed by the same entity as that for the block 802 in FIG. 8. The process block 908 is performed by the same entity as that for block 804 in FIG. 8.

At block 902, the biomarkers may be obtained from the contact lens in any appropriate way. In some examples, the biomarkers may dissociate from the contact lens in a multipurpose contact lens storage solution. In another example, the biomarkers are obtained from the contact lens by wiping a material across the contact lens' surface. In yet other examples, the biomarkers may be removed from the contact lens by scratching the biomarkers off of the lens's surface. In some cases, obtaining the biomarkers from the contact lens results in a contact lens that can be re-worn by the user. In other examples, obtaining the biomarkers from the contact lens results in modifying the contact lens such that it cannot be re-worn by the user. The biomarker characteristic obtainer 545 obtains from, for example, the sensing device 530 information indicating characteristics of the biomarkers obtained as above.

Figure 10:
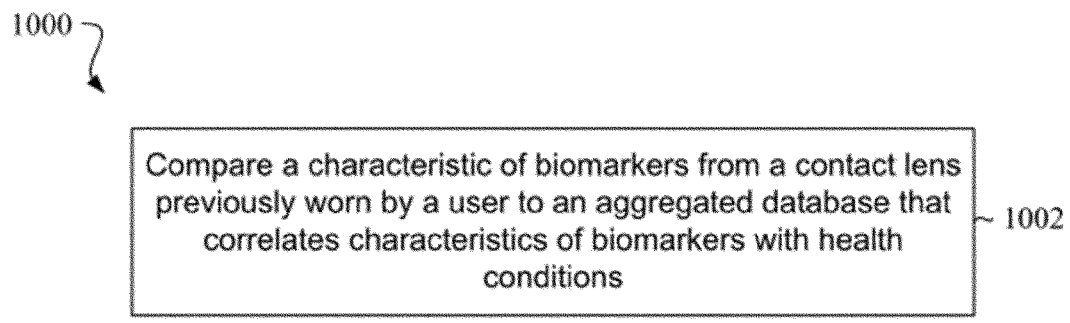
FIG. 10 illustrates a block diagram of a method of an example of determining a health condition, in accordance with the present disclosure.

FIG. 10 illustrates an example of a method 1000 of determining a health condition. In this example, the method 1000 includes comparing 1002 a characteristic of biomarkers from a contact lens previously worn by a user to an aggregated database that correlates characteristics of biomarkers with health conditions. The process block 1002 is performed by the same entity as that for the block 804 in FIG. 8.

The aggregated database may include measurements levels associated with health conditions from multiple sources. In some examples, doctors, patients, other types of professionals, other types of sources, or combinations thereof may contribute information that can be populated into the database. In some cases, thousand and even millions of health conditions with their associated biomarker characteristics may be aggregated into the database.

Further, after the correlated health condition is sent to the user, the user may have an option to confirm whether the health condition was accurate. For example, a user may place his or her contact lens in the storage case and receive a notification that he or she has or may have a health condition. As a result, the user may visit with a doctor, who performs a test to confirm whether the user has that health condition. In the event that the user has the health condition indicated by the database, the user may send a confirmation message to the database. The confirmation message may increase a confidence level of the correlation between the characteristic of the biomarker and the health condition. In the event that the test indicates that the user does not have the health condition indicated by the database, the user may send confirmation message to the database indicating that the user does not have the health condition. This confirmation message may cause a decrease in a confidence level of the correlation between the characteristic of the biomarker and the health condition. In the event that the user does not have the indicated health condition, the database may reassess the correlation drawn and determine whether the correlation drawn is based on proper assumptions. In some cases, the message indicating that the user does not have the indicated health condition may include that the user has a different health condition that was not identified by the database previously. The database may correlate the different health condition with the user's determined biomarker characteristics.

Figure 11:
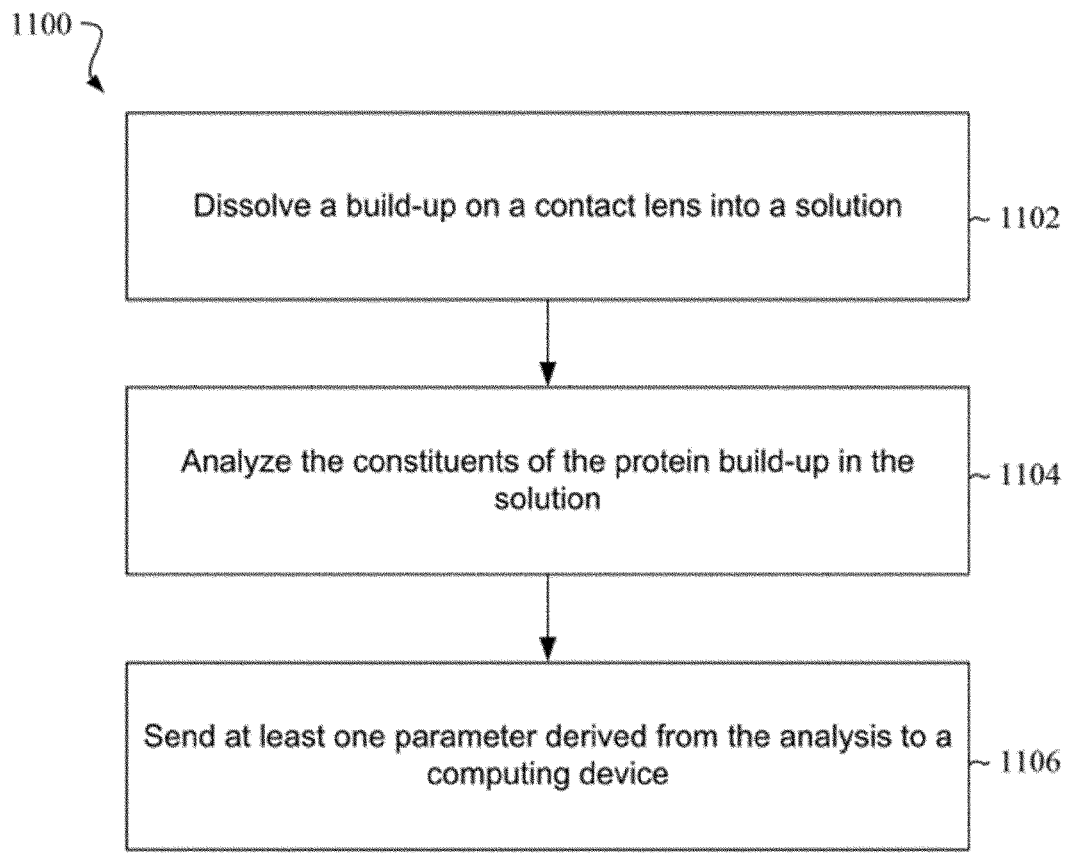
FIG. 11 illustrates a block diagram of a method of an example of determining a health condition, in accordance with the present disclosure.

FIG. 11 illustrates an example of a method 1100 of determining a health condition. In this example, the method 1100 includes dissolving 1102 a build-up on a contact lens into a solution, analyzing 1104 the constituents of the protein build-up in the solution, and sending 1106 at least one parameter derived from the analysis to a computing device. The process blocks 1104 and 1106 are performed by, for example, the sensing device 530.

At block 1102, the build-up may be dissolved by placing the contact lens into a contact lens storage solution. Any appropriate type of contact lens solution may be used. For example, the contact lens solution may be a hydrogen peroxide solution, a multiple purpose storage solution, another type of solution, or combinations thereof.

In some cases, the contact lens solution includes hyaluronan, sulfobetaine, poloxamine, boric acid, sodium borate, ascorbic acid, edetate disodium, sodium chloride, hydroxyalkyl phosphate, poloxamer, sodium phosphate buffer, polyoxyethylene polyoxypropylene block copolymer with ethylene diamine, and polyaminopropyl biguanide, or combinations thereof. The contact lens may include a disinfectant, a surfactant, an anti-fungal agent, an anti-bacterial agent, another type of agent, or combinations thereof.

The removal of the biomarkers from the contact lens into the solution may occur over any appropriate time period. In some examples, the biomarkers are in the solution for at least one minute, at least five minutes, at least 20 minutes, at least 45 minutes, at least an hour, at least two hours, at least 5 hours, at least 7 hours, at least one day, at least two days, another appropriate time period, or combinations thereof.

In some examples, the contact lens is free of surface cavities that are constructed to be binding sites for biomarkers or to draw in tear fluid into the contact lens. In some examples, the contact lens is free of surface treatments that target the binding of specific biomarkers to the contact lens.

In some situations, the storage solutions includes binding agents that are configured to facilitate the bonding between a surface of the contact lens and a biomarker from the tear fluid. In other cases, no binding agents are introduced to the contact lens solution. The contact lens may include a surface where the biomarkers are as likely to bind to any surface of the contact lens as any other surface of the contact lens. In some cases, the biomarkers may attach to the optical zone of the contact lens, a peripheral zone of the contact lens, an edge of the contact lens, a posterior side of the contact lens, an anterior side of the contact lens, another area of the contact lens, or combinations thereof.

The dissolved contents may then be analyzed at block 1104, for example according to the process 802 or 904 described herein with reference to FIGS. 8 and 9, respectively. At block 1106 at least one parameter derived from the analysis is sent to a computing device, for example as described with reference to FIG. 7.

The contact lens may be made through any appropriate mechanism. In some cases, the contact lenses are molded (i.e. cast molded) into their shape. In other examples, the contact lenses are machined to their precise shape. In yet other examples, the contact lens are spin cast. Spin cast contact lenses can have an advantage of making a continuous surface on the posterior side of the contact lens that matches a profile constructed to assist the user with his or her vision. The front side of the contact lens during a spin casting procedure may include a profile that matches a contact lens mold. The contact lens mold may include a continuous, curved surface without interruptions. In some examples, the spin cast contact lens provide for a continuous surface that is substantially free of interruptions, such as micro-cavities. In some cases, having a continuous, interruption free surface on both the anterior side and the posterior side may prevent the collection of tear fluid in the contact lens. Avoiding the collection of tear fluid may prevent the contact lens from having an additional amount of weight. Further, when the contact lens is introduced into the solution, a substantial amount of tear fluid may not mix with the contact lens solution, which may skew the volume of fluid in being analyzed and affect the concentration analyses. In some examples where tear fluid is not collected, just the biomarkers may be carried with the contact lens into the solution. Thus, the analysis does not have to be adjusted to accommodate an increase in fluid. But, in some examples, the amount of fluid being analyzed may not require a precise amount of fluid. In one example, the contact lens case may include a fill line and the measurements performed by the sensor may be adequate enough if the solution is close to being at the fill line, but not required to be precisely at the fill line. Further, by not modifying the contact lens to have an enhanced ability to collect specific biomarkers, the concentrations of the biomarkers that bind to the contact lens may be more reflective of the actual concentration of that biomarker in the tear fluid. An enhanced ability to collect a particular biomarker or a wide variety of biomarkers may cause a disproportionate amount of that biomarker to bind to the contact lens, which may skew the measurement levels made when analyzing the solution and potentially lead to an inaccurate characterization of the biomarker's actual concentration.

FIGS. 12-15 illustrate various components that can be used in certain examples for making a contact lens 110 in accordance with the principles described in the present disclosure. A liquid lens material 1052 can be applied to a profile 1054 of the mold 1042. The mold 1042 with the liquid lens material 1052 can be loaded into a spinning structure 1068 that is configured to spin the mold 1042 so that the liquid lens material 1052 centrifugally spreads across the profile 1054 into the desired shape of the contact lens. A curing agent (e.g., temperature, actinic radiation, or another type of curing agent) is exposed to the liquid lens material 1052 while the mold 1042 is spinning. As a result, the liquid lens material 1052 hardens into the contact lens 110.

Figure 12:
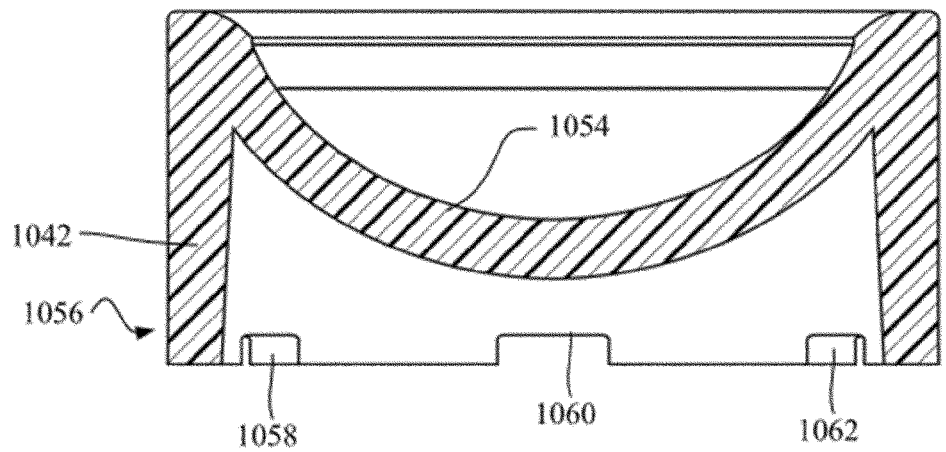
FIG. 12 illustrates an example of a mold for making a contact lens, in accordance with the present disclosure.

FIG. 12 is a cross-sectional view of one embodiment of a mold for a contact lens according to the principles of the present disclosure. In this example, the mold 1042 has a base 1056 with multiple cut outs 1058, 1060, 1062 that are spaced and shaped to interlock with an internal surface of a spinning structure during a later stage of manufacturing. The profile 1054 of the mold 1042 is shaped to form the anterior surface of the contact lens 110. In some examples, the profile 1054 of the mold 1042 may be continuous without substantial interruptions.

Figure 13:
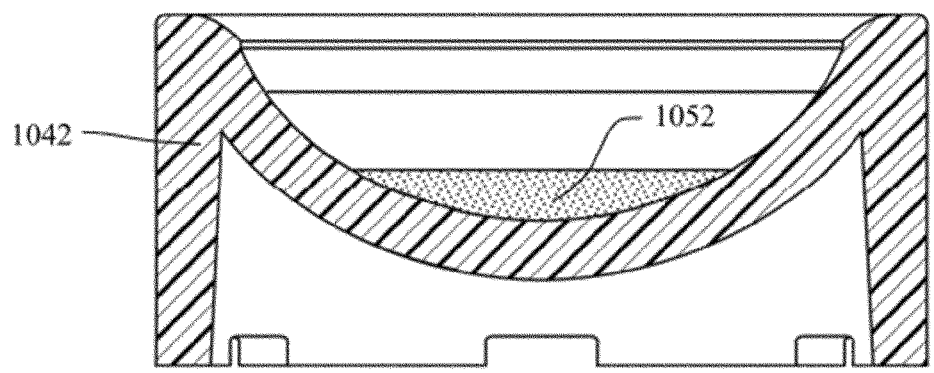
FIG. 13 illustrates an example of a mold for making a contact lens, in accordance with the present disclosure.

FIG. 13 is a cross-sectional view of one embodiment of a mold 1042 with a liquid lens material 1052 according to the principles of the present disclosure. In this example, the liquid lens material 1052 is deposited into the profile 1054 of the mold.

The liquid lens material 1052 can be made from any material suitable for use in contact lenses. For example, the liquid lens material 1052 can be made of any silicone material and/or hydrogel material. Such material may be formed of polymers, such as tefilcon, tetrafilcon A, crofilcon, helfilcon A&B, mafilcon, polymacon, hioxifilcon B, lotrafilcon A, lotrafilcon B, galyfilcon A, senofilcon A, sifilcon A, comfilcon A, enfilcon A, lidofilcon B, surfilcon A, lidofilcon A, alfafilcon A, omafilcon A, vasurfilcon A, hioxifilcon A, hioxifilcon D, nelfilcon A, hilafilcon A, acofilcon A, bufilcon A, deltafilcon A, phemfilcon A, bufilcon A, perfilcon, etafilcon A, focofilcon A, ocufilcon B, ocufilcon C, ocufilcon D ocufilcon E, ocufilcon F, phemfilcon A, methafilcon A, methafilcon B, vilfilcon A, other types of polymers, monomers, or combinations thereof. These materials may include various combinations of monomers, polymers, and other materials to form the liquid lens material.

In one embodiment, the liquid lens material is made of hydrogel polymers without any silicone. This may be desirable to increase the wettability of the contact lens. In another embodiment, the liquid lens material is made of silicone hydrogel material.

The contact lens 110 can be shaped and sized based on a variety of factors, including the shape and size of the user's eye and various optical properties to be achieved by a central portion of the contact lens. In some examples, the total thickness of the contact lens 110 can be approximately 0.1 mm to approximately 0.14 mm. The thickness of the contact lens 110 may gradually vary at different locations on the contact lens 110. For example, the contact lens 110 can be thicker near the outer edge of the contact lens 110 than in the central portion of the contact lens 110.

Figure 14:
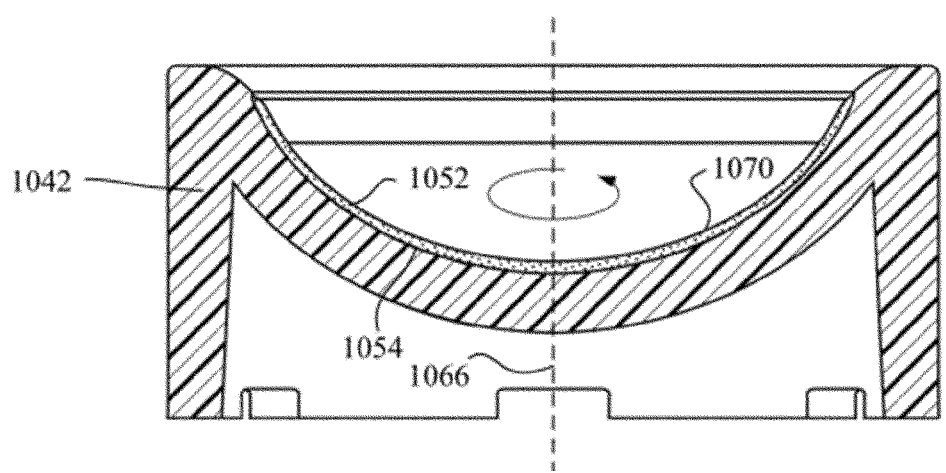
FIG. 14 illustrates an example of a mold for making a contact lens, in accordance with the present disclosure.
Figure 15:
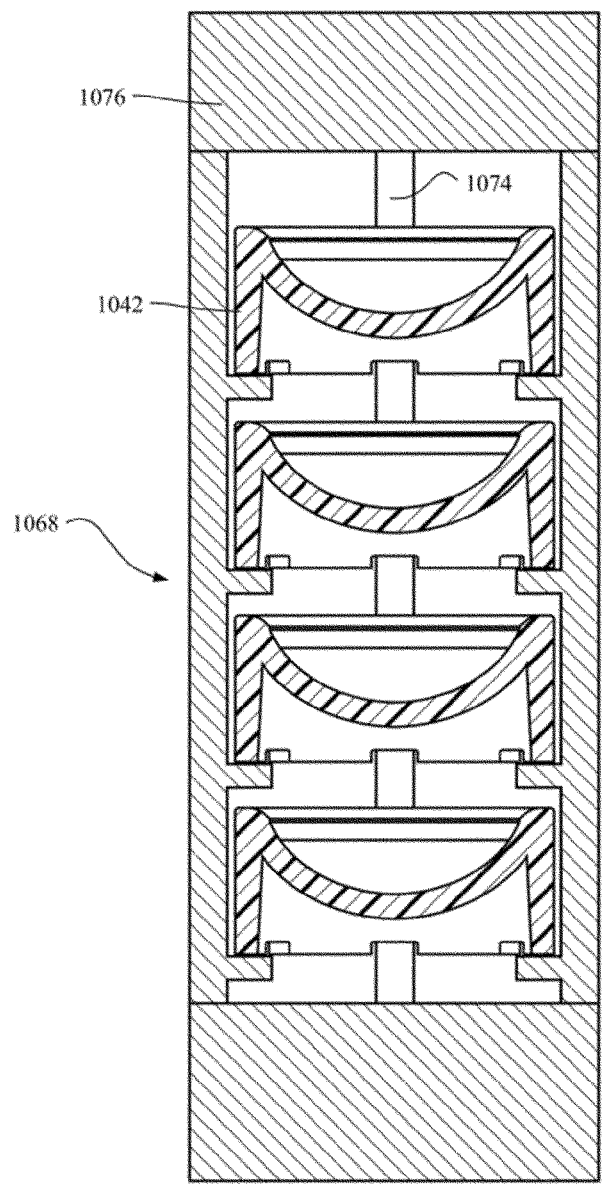
FIG. 15 illustrates an example of a spinning structure for making a contact lens, in accordance with the present disclosure.

FIGS. 14 and 15 are cross-sectional views of a mold 1042 with a liquid lens material 1052 centrifugally spreading across a profile 1054 of the mold 1042 according to the principles of the present disclosure. In this example, the mold 1042 is spun around a central axis 1066 within a spinning structure (1068, FIG. 15). The spinning structure 1068 is rotated at a speed and in such a way that forms the desired posterior surface 1070 of the contact lens 110.

The spinning structure 1068 includes a central loading region that can receive the molds 1042 that contain the liquid lens material 1052. The central loading region may be formed by a glass tube, a metal tube, or another type of structure that can retain the molds 1042 in a stacked orientation. In examples where actinic radiation is used as the curing agent, the spinning structure 1068 may have an opaque material, a semi-transparent material, or a transparent material that include a sufficient amount of openings to allow the actinic radiation into the central loading region. In the example of FIG. 15, the spinning structure 1068 includes multiple guide posts 1074 that retain the molds 1042 in a stacked orientation. The spinning structure 1068 also includes a region 1076 that can be used to attach to a spinning driver, such as a motor.

The spinning structure 1068 may be programmed to rotate in a precise manner to form the desired posterior surface 1070 of the contact lens 110, which is the surface of the contact lens that is intended to contact the eye. The program that causes the spinning structure 1068 to rotate can be modified to create a desired profile for different users based on each user's individual prescription. The curing agent is applied to the liquid lens material 1052 while the spinning structure 1068 rotates the molds 1042. As a result, the contact lens 110 is formed while the spinning structure rotates. In some examples, the contact lenses are fully cured within the spinning structure. But, in other examples, the contact lens 110 may be fully cured over the course of multiple curing stages. For example, the contact lens may be cured in the spinning structure 1068 to a point where the liquid lens material retains its shape but is not fully cured. At this stage, the mold with the contact lens may be removed from the spinning structure to finish curing in an environment that is cost effective. A spinning structure that is compatible with the principles described herein is described in U.S. Patent Publication 2012/0133064 issued to Stephen D. Newman. U.S. Patent Publication 2012/0133064 is herein incorporated by reference for all that is discloses.

The spin casting method of forming the curve of the posterior side of the contact lens may result in a continuous surface that is substantially free or entirely free of cavities or micro-cavities.

The principles described in the present disclosure may be applied to other devices that may reside within cavities of the user. For example, a user's mouth guard may be placed in a solution for cleaning when it is removed from the user's mouth after a night's sleep. Proteins, antibodies, lipids, enzymes, electrolytes, and so forth may bind to the mouth guard. These biomarkers may dissociate with the mouth guard into the solution and may be analyzed. The measured biomarker levels may be compared to the correlations contained in a database to determine a dental condition of a user or another type of condition of a user.

In other examples, the device may be a tooth brush, cotton swabs, floss, a q-tip, a head phone, needles, a digestible device, band aids, another type of bandage, removable orthopedic hardware, other types of hardware, chewing gum, other types of device, or combinations thereof.

Figure 16:
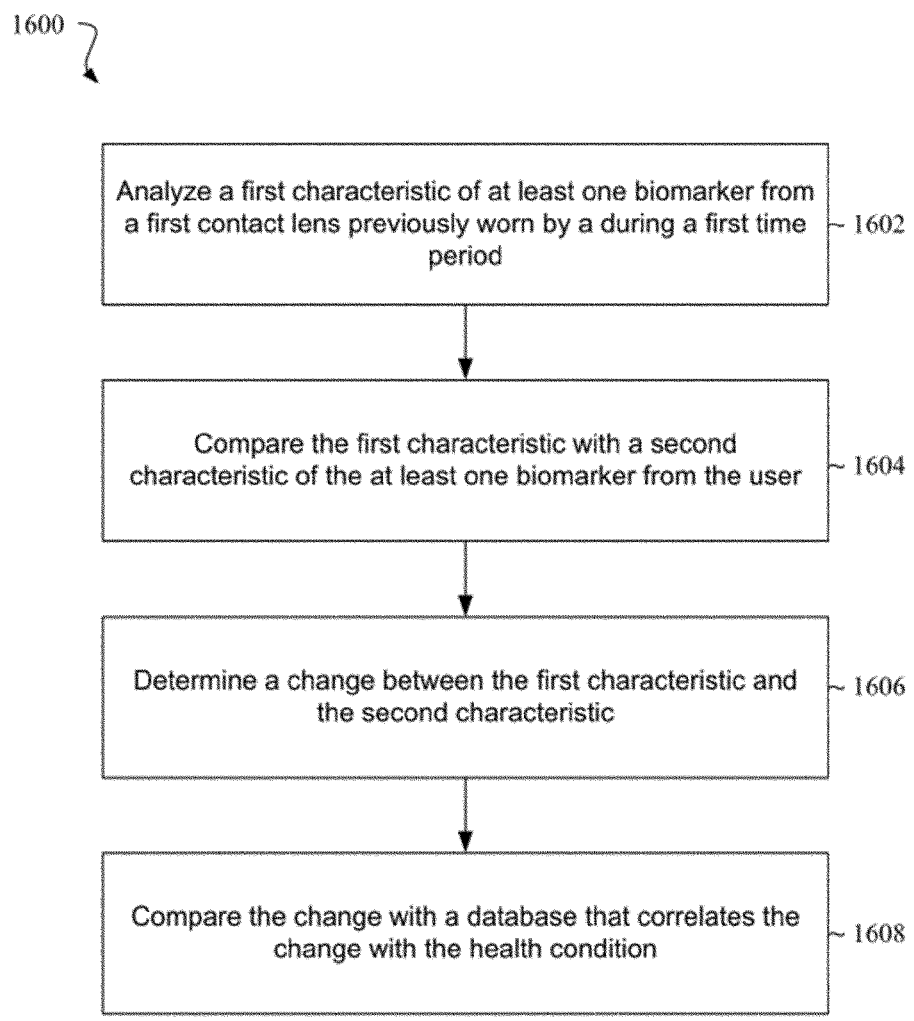
FIG. 16 illustrates a block diagram of a method of an example of determining a health condition, in accordance with the present disclosure.

FIG. 16 depicts an example of a method 1600 for determining a health condition of a user. In this example, the method 1600 includes analyzing 1602 a first characteristic of at least one biomarker from a first contact lens previously worn by a user during a first time period, comparing 1604 the first characteristic with a second characteristic of the at least one biomarker from the user, determining 1606 a change between the first characteristic and the second characteristic, and comparing 1608 the change with a database that correlates the change with the health condition. The process block 1602 is performed by the same entity as that for the block 802 in FIG. 8. The process block 1604 through 1608 are performed by the processor 515 (specifically, the biomarker and database comparer 555, for example).

At block 1604, the first characteristic is compared to a second characteristic. The first and second characteristics may be obtained from the same contact lens that is worn at different times. For example, the user may wear the contact lens on a first day and remove the contact lens at the end of the first day when the user has the biomarkers removed from contact lens. An analysis on the biomarkers may be done to obtain the first concentration, such as a first concentration of a first biomarker. On the second day, the user may place the contact lens back into his or her eye and removed the contact lens at the end of the day. The biomarker removal and analysis may also be performed. The second characteristic may be a different concentration of the first biomarker. Thus, the change may be an increased concentration, a decreased concentration, another type of concentration, or combinations thereof.

In some cases when the same contact lens is used to obtain the second set of biomarkers, the database may include specific correlations. In some cases, not all of the biomarkers may be removed from the contact lens during the first night of cleaning, therefore, the second night when the contact lens is placed in the solution for cleaning more biomarkers may be obtained. In other examples, those biomarkers that remain on the contact lens after the first cleaning may block other biomarkers from attaching to the contact lens such that it is common to obtain fewer biomarkers on the second night. In other examples, the second set of biomarkers may be obtained from a fresh contact lens. In those situations, lingering biomarkers from the previous cleaning time may not an issue. The second set of biomarkers (second characteristics) may be obtained from a second contact lens that is different than a first contact lens (the contact lens from which the first characteristics are obtained).

At block 1608, the change between the first and second concentrations may be compared to the database where the change is correlated with a health condition. The computing device may, with reference to the database, send, and the user (i.e. the mobile device, hand-held device, sensor, etc.) may receive an indication of the correlated health condition.

In some cases, the first characteristic is obtained at a different time than when the second characteristic is obtained. In other cases, the first and second characteristics may be obtained in about the same time period. For example, a first contact lens may be worn in a first eye and a second contact lens may be worn in a second eye, and the characteristics of the biomarkers may be analyzed. In those situations where the characteristics are different, there may be condition present in one of the eyes that is not in the other eye.

The user may have an account associated with the hand-held device, the mobile device, the database, or associated with another computing device that stores at least some of the characteristics of the user's biomarkers when they are sent to the database. These stored recordings may compile a health history of the user. The health history may be reviewed by the doctor to assist with helping to detect other health conditions, assist in making a treatment plan, assist in making a prevention plan, assist in helping diagnosis health conditions of relatives, determine other types of information, or combinations thereof.

Unless otherwise indicated, all numbers or expressions, such as those expressing dimensions, physical characteristics, etc., used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques.

In addition, all ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

Embodiment 2

The following description will discuss Embodiment 2. The reference signs which contain the same numerals will be given to configurations already described above, and descriptions on such members may be omitted. The same is true of Embodiment 3 and its subsequent embodiments.

Figure 17:
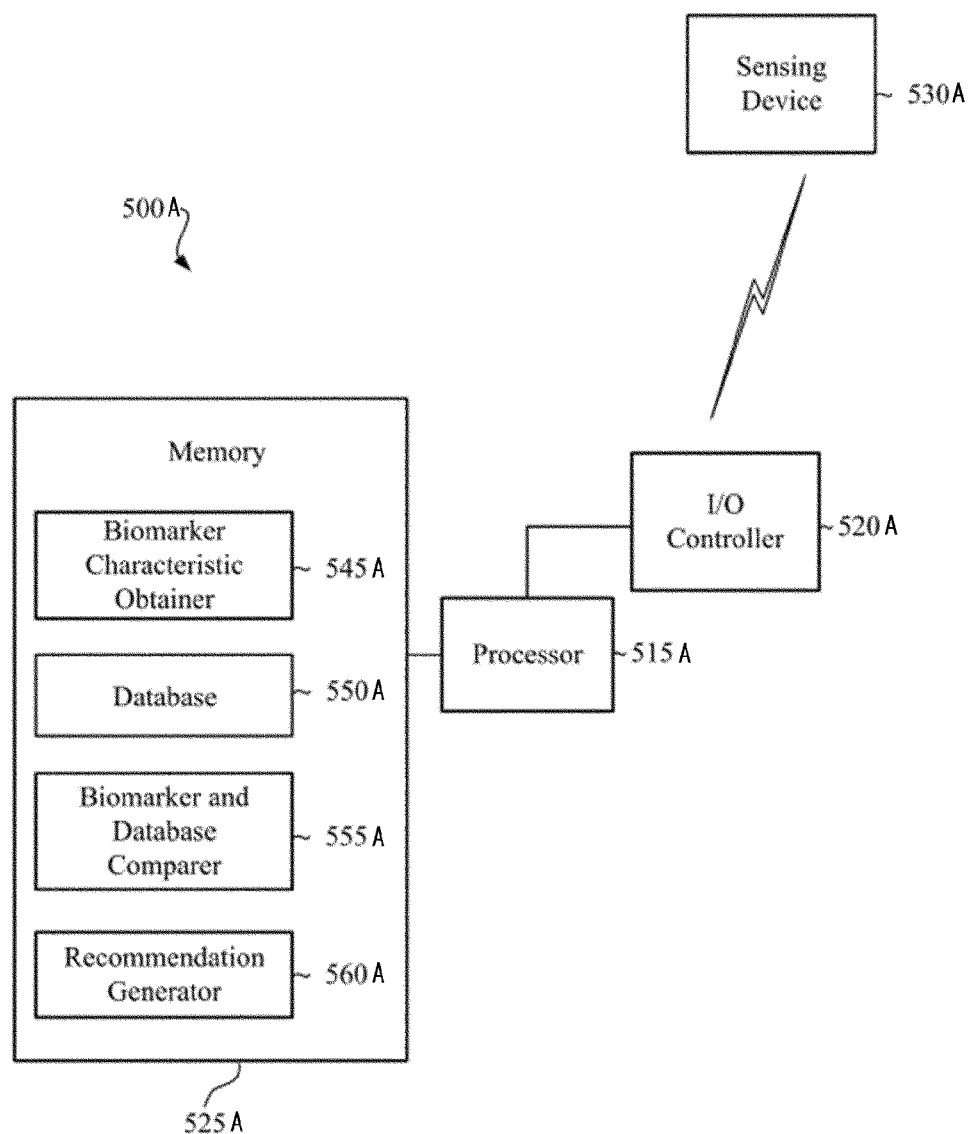
FIG. 17 depicts a diagram of a recommendation system.

FIG. 17 depicts a diagram of a recommendation system 500A. The system 500A includes a processor 515A, an I/O controller 520A, and memory 525A. The processor 515A and the memory 525A are components of the computing device. The database 550A represents a data structure that holds information about characteristics of the biomarkers. The database 550A may be filled with information about the characteristics that have been measured in labs, for example by chemometric methods, obtained from at least one user, or combinations thereof. In some examples, the database may be initially populated with information from users with a history of wearing contact lens that know that certain contact lens types were comfortable for them, caused them discomfort, or had a different experience. These users may submit their biomarkers profiles along with their contact lens histories. In some cases, the users have their biomarker profiles determined to detect a health condition or for another reason other than a contact lens recommendation. In some examples, thousands to millions of samples may be collected.

The biomarker and database comparer 555A represents programmed instructions that cause the processor 515A to compare the obtained biomarker characteristic against the information stored in the database. In other words, the processor 515A executes the programmed instructions to function as the biomarker and database comparer 555A. In some examples, the programmed instructions may include data mining algorithms to compare biomarker characteristics. The recommendation generator 560A represents programmed instructions that cause the processor 515A to generate a contact lens recommendation based on the user's biomarker profile. In other words, the processor 515A executes the programmed instructions to function as the recommendation generator 560A.

Correlations between certain biomarkers and their respective concentrations may go unobserved on one-on-one analysis with each of the patients. However, with such a large sample size, correlations that have been previously unobserved may be detected. For example, an analysis may be run on all the biomarker characteristics of users with a specific contact lens preference. Such an analysis may reveal that certain biomarkers that had not previously been linked to that contact lens preference has a statistically significant normal concentration level, a statistically significant low concentration level, a statistically significant high concentration level, another statistically significant concentration level, a statistically insignificant type of concentration level, or combinations thereof that had not previously been observed.

The recommendation may include having a confirmation request to confirm whether or not the user has a good experience with the recommended contact lens. In those cases where a confirmation request is sent and a confirmation message is received, the results of the confirmation test may be sent to the computing device. The results may be used to assist the database and its associated analytics to improve future recommendations. The confirmation may be conducted by a device that used by the user (for example, a mobile device).

FIG. 18 depicts an example of a database 600A that associates a characteristic of the tear chemistry, eye condition (health condition), and contact lens recommendation. In this example, the database 600A includes a first column 602A that represents the tear chemistry, a second column 604A that eye conditions, and a third column 606A that represents the recommendation. The database 600A may include a first row 608A that includes the correlation for a tear chemistry with a normal first biomarker level and a normal second biomarker level, a second row 610A that includes the correlation for a tear chemistry with a normal first biomarker level and a high second biomarker level, a third row 612A that includes the correlation for a tear chemistry with a low first biomarker level and a normal second biomarker level, a fourth row 614A that includes the correlation for a tear chemistry with a low first biomarker level, a fifth row 616A that includes the correlation for a tear chemistry with a high first biomarker level, and a sixth row 618A that includes the correlation for a tear chemistry with a high second biomarker level.

While the example of FIG. 18 depicts an example with the correlations of specific types of biomarkers, any appropriate type of correlation may be included in the database. In some instances, the characteristics correlated with a single biomarker may be included as depicted in rows 614A, 616A, 618A. In other instances, the characteristics correlated with a specific set of biomarkers may be included. For example, the recommendations correlated with two or more characteristics of different types of biomarkers may be included as depicted in rows 608A, 610A, 612A. Any appropriate number of biomarker characteristics may be included. For example, three to hundreds of characteristics may be collectively correlated to a specific type of health condition. Further, while the example of FIG. 18 includes specific types of biomarkers, the database may include any appropriate type of biomarker correlations. In the example shown in FIG. 18, whether a biomarker level is "Normal", "Low", or "High" can be determined by comparing the measurement value of the biomarker with a predetermined threshold.

Figure 19:
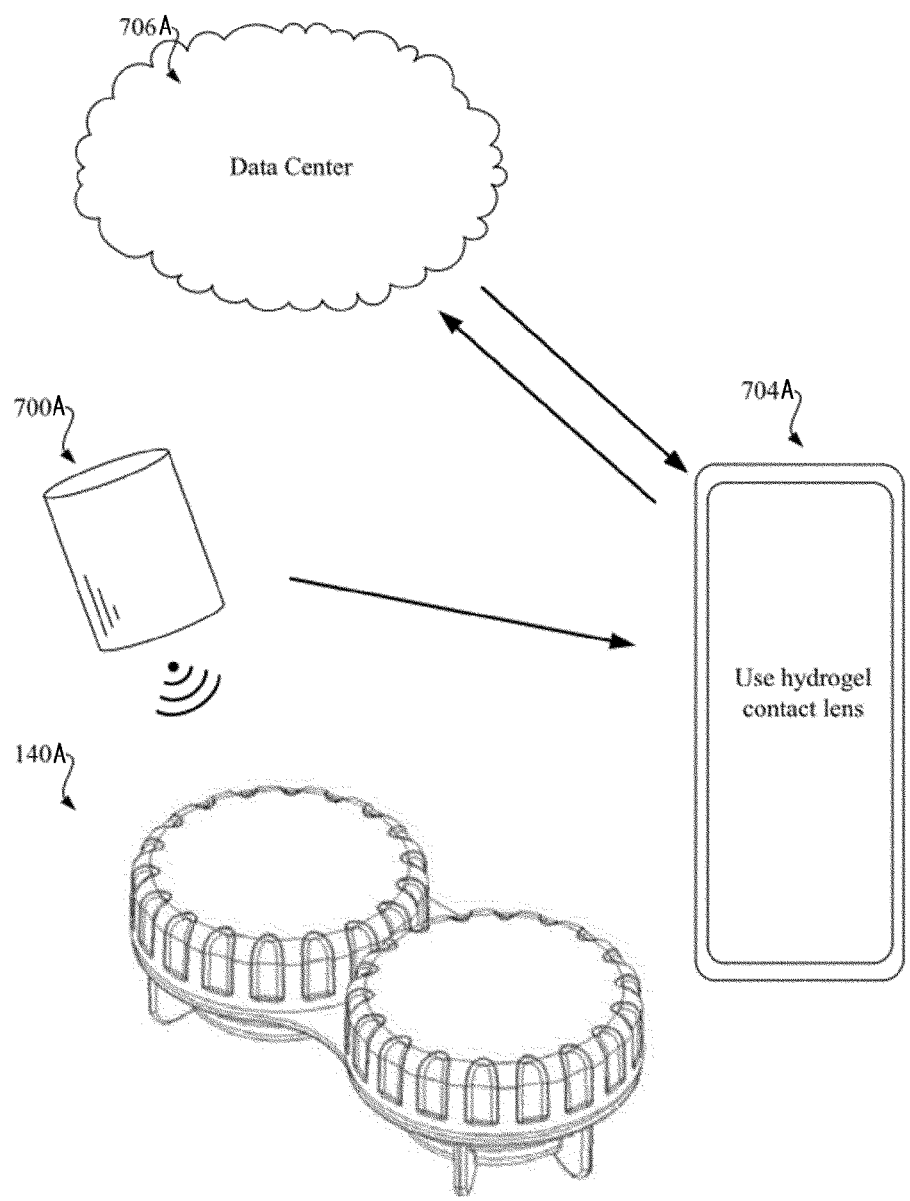
FIG. 19 depicts an example of a system of recommending a contact lens of a user.

FIG. 19 depicts an example of a system 702A of recommending a contact lens of a user. In this example, a storage solution may be contained within a contact lens container 140A. A hand-held device 700A with a sensor may be used to take a measurement of at least one characteristic of the biomarkers in the solution. The hand-held device 700A may send the recorded levels to a mobile device 704A (computing device) that is in communication with a cloud based data center 706A that stores the database (FIG. 18, 600A). The mobile device 704A may relay the recorded levels to the database in the data center 706A, which may send the correlations back to the mobile device 704A. The mobile device 704A may present the results from the hand-held device and/or the correlations from the database in a user-interface of the mobile device 704A.

At least some of the processing of the measurements obtained from the return signals from the storage solution may occur at the hand-held device 700A, the mobile device 704A, and/or the data center 706A. In some examples, the mobile device 704A includes a program that retrieves the correlations from the database and performs additional tasks. For example, the mobile device 704A may retrieve information about the recommended contact lens from another source other than the database in response to receiving the recommendation from the database. Another additional task that the mobile device 704A may perform in response to receiving the health condition is to retrieve a health professional's contact information that can preside that type of contact lens, consult a user's calendar to set up an appointment with the health professional, schedule an appointment with the health professional, perform another task, purchase that type of contact lens, request samples of that type of contact lens for the user, or combinations thereof.

Figure 20:
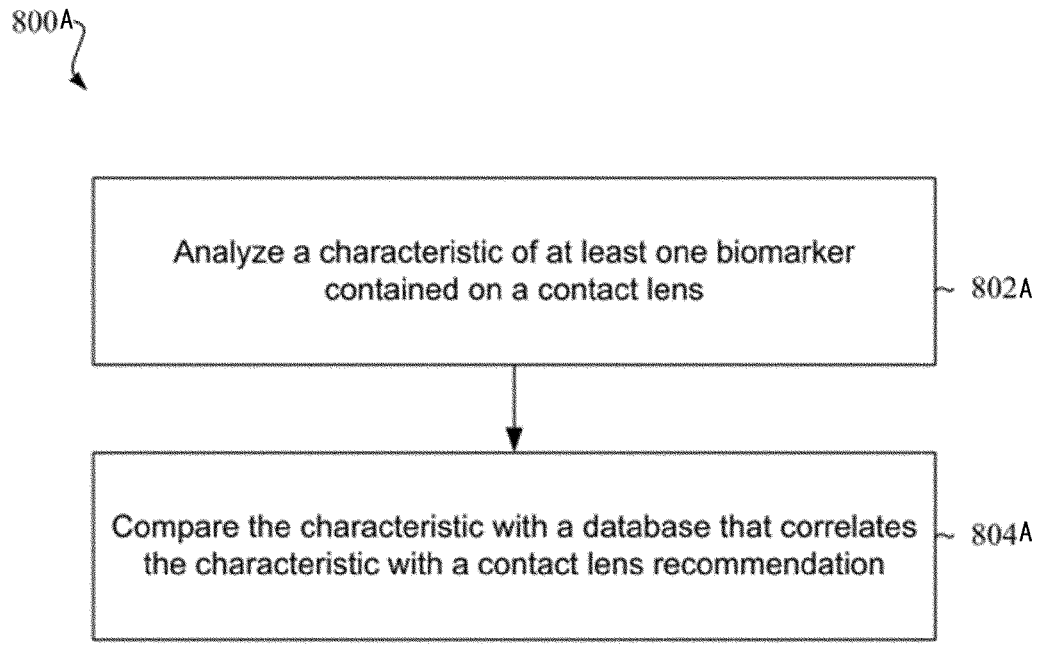
FIG. 20 illustrates an example of a method of recommending a contact lens.

FIG. 20 illustrates an example of a method 800A of recommending a contact lens. In this example, the method 800A includes analyzing 802A a characteristic of at least one biomarker contained on a contact lens and comparing 804A the characteristic with a database that correlates the characteristic with a contact lens recommendation.

At block 802A, a characteristic of at least one biomarker is analyzed. This process may be performed by the sensing device 530A or by the processor 515A (specifically, the biomarker characteristic obtainer 545A) after the processor 515A obtains the measurements of the sensor from the sensing device 530A. The biomarkers can be obtained from a contact lens. In some cases, the biomarkers remain on the contact lens when the biomarkers are being analyzed. In other examples, the biomarkers are removed from the contact lens before the analysis. The characteristic may include a type of biomarker, a concentration of biomarker, a location of the biomarker on the contact lens, another type of characteristic, or combinations thereof. The characteristic may involve a single biomarker. In other examples, the characteristic includes the collective condition of multiple biomarkers.

At block 804A, the characteristic may be compared to a database (for example, the database 550A in FIG. 17) that correlates the characteristic with a contact lens type or recommendation. This process is performed by the processor 515A (specifically, the biomarker and database comparer 555A). For example, the database may include the type and concentration of a single biomarker that is correlated with a specific type of contact lens. In another example, the database may correlate that when a first type of biomarker has a specific concentration and a second type of biomarker has different specific concentration that is associated with a specific type of contact lens.

Figure 21:
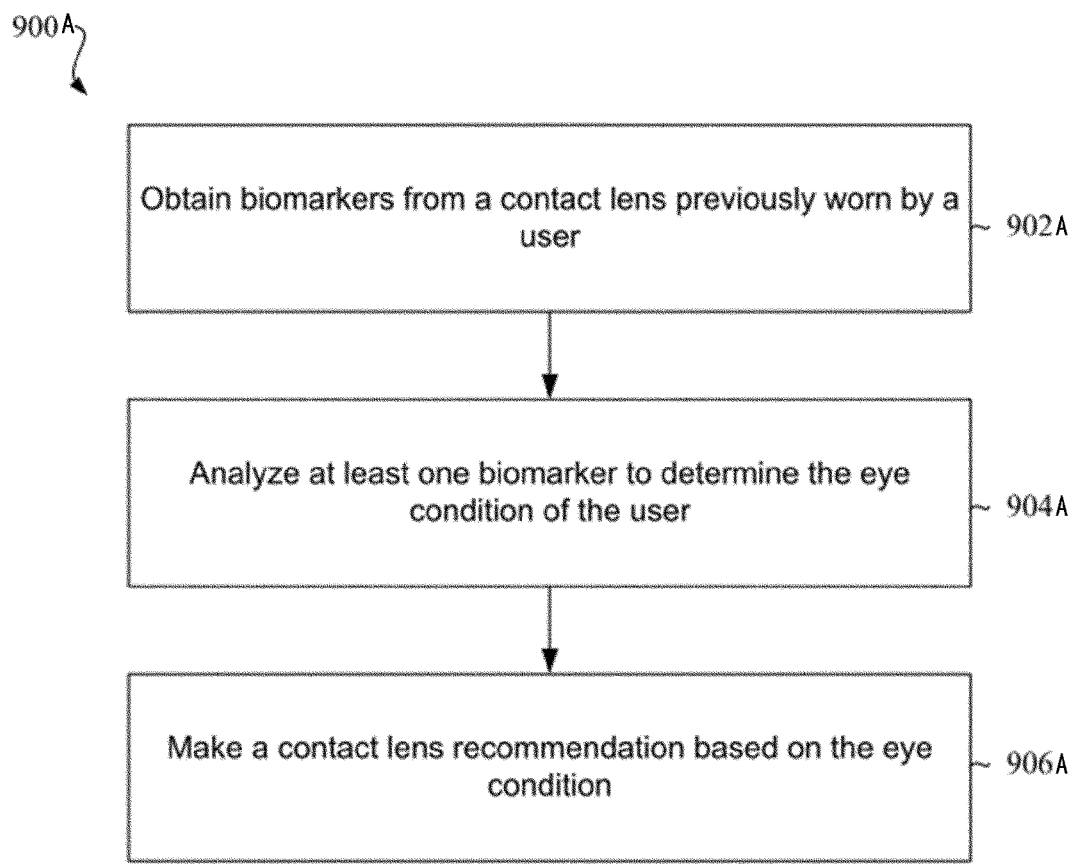
FIG. 21 illustrates an example of a method of making a contact lens recommendation.

FIG. 21 illustrates an example of a method 900A of making a contact lens recommendation. In this example, the method 900A includes obtaining 902A biomarkers from a contact lens previously worn by a user, analyzing 904A at least one biomarker to determine the eye condition of the user, making 906A a contact lens recommendation based on the eye condition. The process block 904A is performed by the same entity as that for the block 802A in FIG. 20. The process block 906A is performed by the processor 515A (specifically, the recommendation generator 560A).

At block 902A, the biomarkers may be obtained from the contact lens in any appropriate way. In some examples, the biomarkers may dissociate from the contact lens in a multiple purpose contact lens storage solution. In another example, the biomarkers are obtained from the contact lens by wiping a material across the contact lens' surface. In yet other examples, the biomarkers may be removed from the contact lens by scratching the biomarkers off of the lens's surface. In some cases, obtaining the biomarkers from the contact lens results in a contact lens that can be re-worn by the user. In other examples, obtaining the biomarkers from the contact lens results in modifying the contact lens such that it cannot be re-worn by the user. The biomarker characteristic obtainer 545A obtains from, for example, the sensing device 530A information indicating characteristics of the biomarkers obtained as above.

Figure 22:
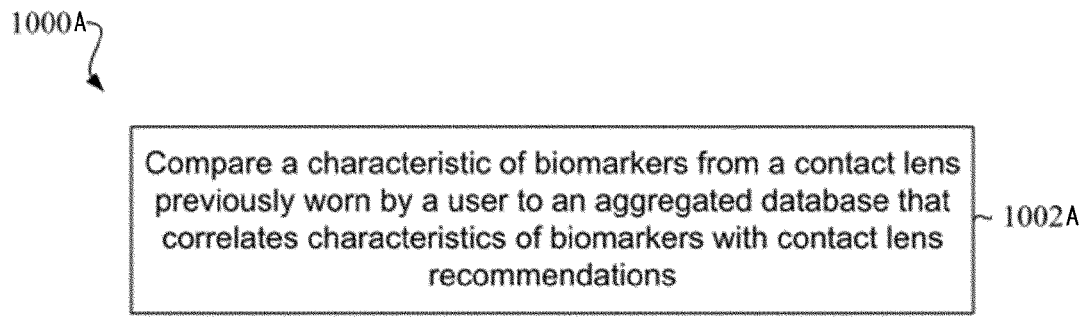
FIG. 22 illustrates an example of a method of making a contact lens recommendation.

FIG. 22 illustrates an example of a method 1000A of making a contact lens recommendation. In this example, the method 1000A includes comparing 1002A a characteristic of biomarkers from a contact lens previously worn by a user to an aggregated database that correlates characteristics of biomarkers with contact lens recommendations. The process block 1002A is performed by the same entity as that for the block 804A in FIG. 20.

The aggregated database may include measurements levels associated with contact lens recommendations from multiple sources. In some examples, doctors, patients, other types of professionals, other types of sources, or combinations thereof may contribute information that can be populated into the database. In some cases, thousand and even millions of health conditions and/or contact lens recommendations with their associated biomarker characteristics may be aggregated into the database.

Further, after the correlated contact lens type is sent to the user, the user may have an option to confirm whether the contact lens type was accurate. For example, a user may place his or her contact lens in the storage case and receive a recommendation indicating that another contact lens may be a better fit for the user. As a result, the user may purchase that type of contact lens. In the event that the user likes the recommended contact lens, the user may send a confirmation message to the computing device to update the database to indicate the user's experience with the contact lens. The confirmation message may increase a confidence level of the correlation between the characteristic of the biomarker and the recommendation. In the event that the user does not have a good experience with the recommended contact lens after trying them, the user may send confirmation message to the database indicating the poor experience. This confirmation message may cause a decrease in a confidence level of the correlation between the biomarker profile and the recommended contact lens. In the event that the user does not like the recommended contact lens, the database may reassess the correlation drawn and determine whether the correlation drawn is based on proper assumptions.

Figure 23:
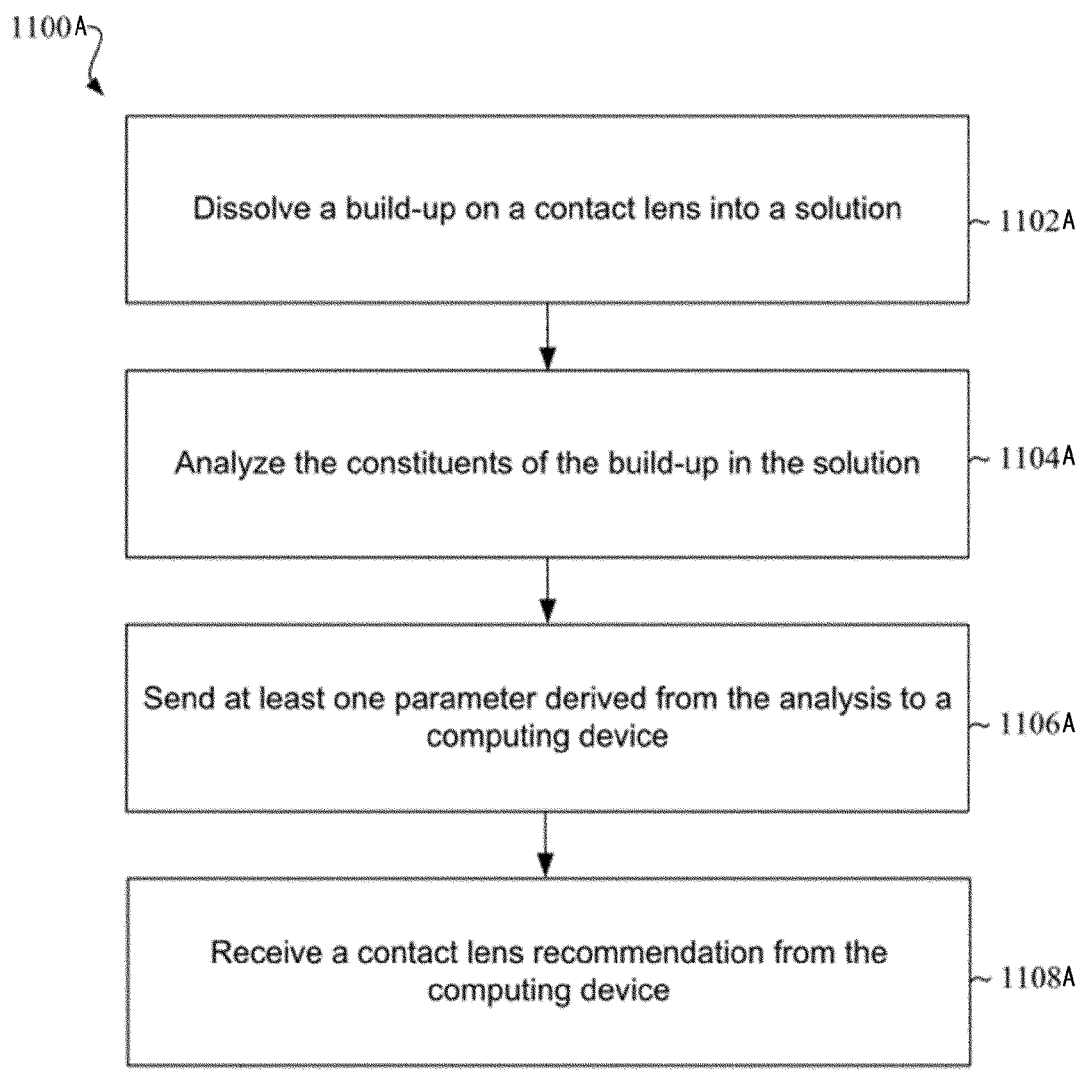
FIG. 23 illustrates an example of a method of recommending a contact lens.

FIG. 23 illustrates an example of a method 1100A of recommending a contact lens. In this example, the method 1100A includes dissolving 1102A a build-up on a contact lens into a solution, analyzing 1104A the constituents of the protein build-up in the solution, sending 1106A at least one parameter derived from the analysis to a computing device; and receiving 1108A a contact lens recommendation from the computing device. The process blocks 1104A and 1106A are performed by, for example, the sensing device 530A. The process block 1108A is performed by, for example, a mobile device of the user.

At block 1102A, the build-up may be dissolved by placing the contact lens into a contact lens storage solution. Any appropriate type of contact lens solution may be used. For example, the contact lens solution may be a hydrogen peroxide solution, a multiple purpose storage solution, another type of solution, or combinations thereof.

In some cases, the contact lens solution includes hyaluronan, sulfobetaine, poloxamine, boric acid, sodium borate, ascorbic acid, edetate disodium, sodium chloride, hydroxyalkyl phosphate, poloxamer, sodium phosphate buffer, polyoxyethylene polyoxypropylene block copolymer with ethylene diamine, and polyaminopropyl biguanide, or combinations thereof. The contact lens may include a disinfectant, a surfactant, an anti-fungal agent, an anti-bacterial agent, another type of agent, or combinations thereof.

The removal of the biomarkers from the contact lens into the solution may occur over any appropriate time period. In some examples, the biomarkers are in the solution for at least one minute, at least five minutes, at least 20 minutes, at least 45 minutes, at least an hour, at least two hours, at least 5 hours, at least 7 hours, at least one day, at least two days, another appropriate time period, or combinations thereof.

In some examples, the contact lens is free of surface cavities that are constructed to be binding sites for biomarkers or to draw in tear fluid into the contact lens. In some examples, the contact lens is free of surface treatments that target the binding of specific biomarkers to the contact lens.

In some situations, the storage solutions includes binding agents that are configured to facilitate the bonding between a surface of the contact lens and a biomarker from the tear fluid. In other cases, no binding agents are introduced to the contact lens solution. The contact lens may include a surface where the biomarkers are as likely to bind to any surface of the contact lens as any other surface of the contact lens. In some cases, the biomarkers may attach to the optical zone of the contact lens, a peripheral zone of the contact lens, an edge of the contact lens, a posterior side of the contact lens, an anterior side of the contact lens, another area of the contact lens, or combinations thereof.

The dissolved contents may then be analyzed at block 1104A, for example according to the process 802A or 904A described herein with reference to FIGS. 20 and 21, respectively. At block 1106A at least one parameter derived from the analysis is sent to a computing device, for example as described with reference to FIG. 19. At block 1108A, the user (technically the user's device) receives a contact lens recommendation from the computing device. In some cases, the recommendation may be derived from the at least one parameter sent to the computing device, according to the methods described herein.

Figure 24:
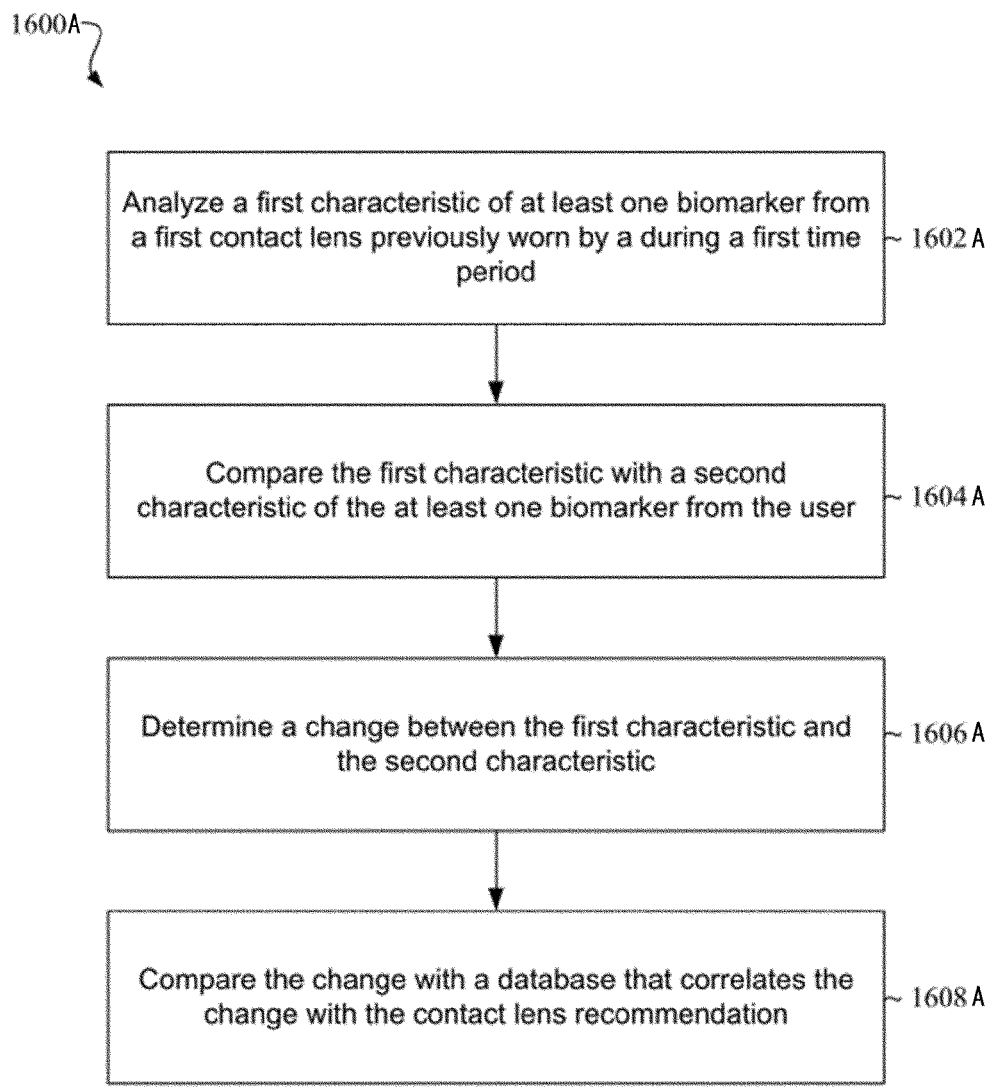
FIG. 24 depicts an example of a method for determining a contact lens recommendation.

FIG. 24 depicts an example of a method 1600A for determining a contact lens recommendation. In this example, the method 1600A includes analyzing 1602A a first characteristic of at least one biomarker from a first contact lens previously worn by a user during a first time period, comparing 1604A the first characteristic with a second characteristic of the at least one biomarker from the user, determining 1606A a change between the first characteristic and the second characteristic, and comparing 1608A the change with a database that correlates the change with the contact lens recommendation. The process block 1602A is performed by the same entity as that for the block 802A in FIG. 20. The process block 1604A through 1608A are performed by the processor 515A (specifically, the biomarker and database comparer 555A, for example).

At block 1604A, the first characteristic is compared to a second characteristic. The first and second characteristics may be obtained from the same contact lens that is worn at different times. For example, the user may wear the contact lens on a first day and remove the contact lens at the end of the first day when the user has the biomarkers removed from contact lens. An analysis on the biomarkers may be done to obtain the first concentration, such as a first concentration of a first biomarker. On the second day, the user may place the contact lens back into his or her eye and remove the contact lens at the end of the day. The biomarker removal and analysis may also be performed. The second characteristic may be a different concentration of the first biomarker. Thus, the change may be an increased concentration, a decreased concentration, another type of concentration, or combinations thereof.

In some cases when the same contact lens is used to obtain the second set of biomarkers, the database may include specific correlations. In some cases, not all of the biomarkers may be removed from the contact lens during the first night of cleaning, therefore, the second night when the contact lens is placed in the solution for cleaning more biomarkers may be obtained. In other examples, those biomarkers that remain on the contact lens after the first cleaning may block other biomarkers from attaching to the contact lens such that it is common to obtain fewer biomarkers on the second night.

In other examples, the second set of biomarkers may be obtained from a fresh contact lens. In those situations, lingering biomarkers from the previous cleaning time may not be an issue. The second set of biomarkers (second characteristics) may be obtained from a second contact lens which is different from a first contact lens (the contact lens from which the first characteristics are obtained).

At block 1608A, the change between the first and second concentrations may be compared to the database where the change is correlated with a recommendation of a contact lens, the recommendation being correlated with the health condition of the user. The computing device may, with reference to the database, send, and the user (i.e. the mobile device, hand-held device, sensor, etc.) may receive an indication of the recommendation. The database may include the correlated health condition. In this case, the computing device may send, and the user may receive an indication of the correlated health condition.

In some cases, the first characteristic is obtained at a different time than when the second characteristic is obtained. In other cases, the first and second characteristics may be obtained in about the same time period. For example, a first contact lens may be worn in a first eye and a second contact lens may be worn in a second eye, and the characteristics of the biomarkers may be analyzed. In those situations where the characteristics are different, there may be a condition present in one of the eyes that is not in the other eye.

The user may have an account associated with the handheld device, the mobile device, the database, or associated with another computing device that stores at least some of the characteristics of the user's biomarkers when they are sent to the database. These stored recordings may compile a health history of the user. The health history may be reviewed by the doctor to assist with helping to detect other health conditions, assist in making a treatment plan, assist in making a prevention plan, assist in helping diagnosis health conditions of relatives, determine other types of information, change contact lens recommendation, or combinations thereof. In some cases, the eye may react to a contact lens by producing a certain biomarker over time. By comparing the user's biomarker profile from earlier sessions of wearing that contact lens, a baseline profile may be obtained that is specific to that user. As the biomarker profile changes over time, it may be discovered that the user's eye is producing a higher level of a certain biomarker that is high for that user, even though the user's concertation of that biomarker may be within a normal level of a significant portion of the population.

Embodiment 3

Figure 25:
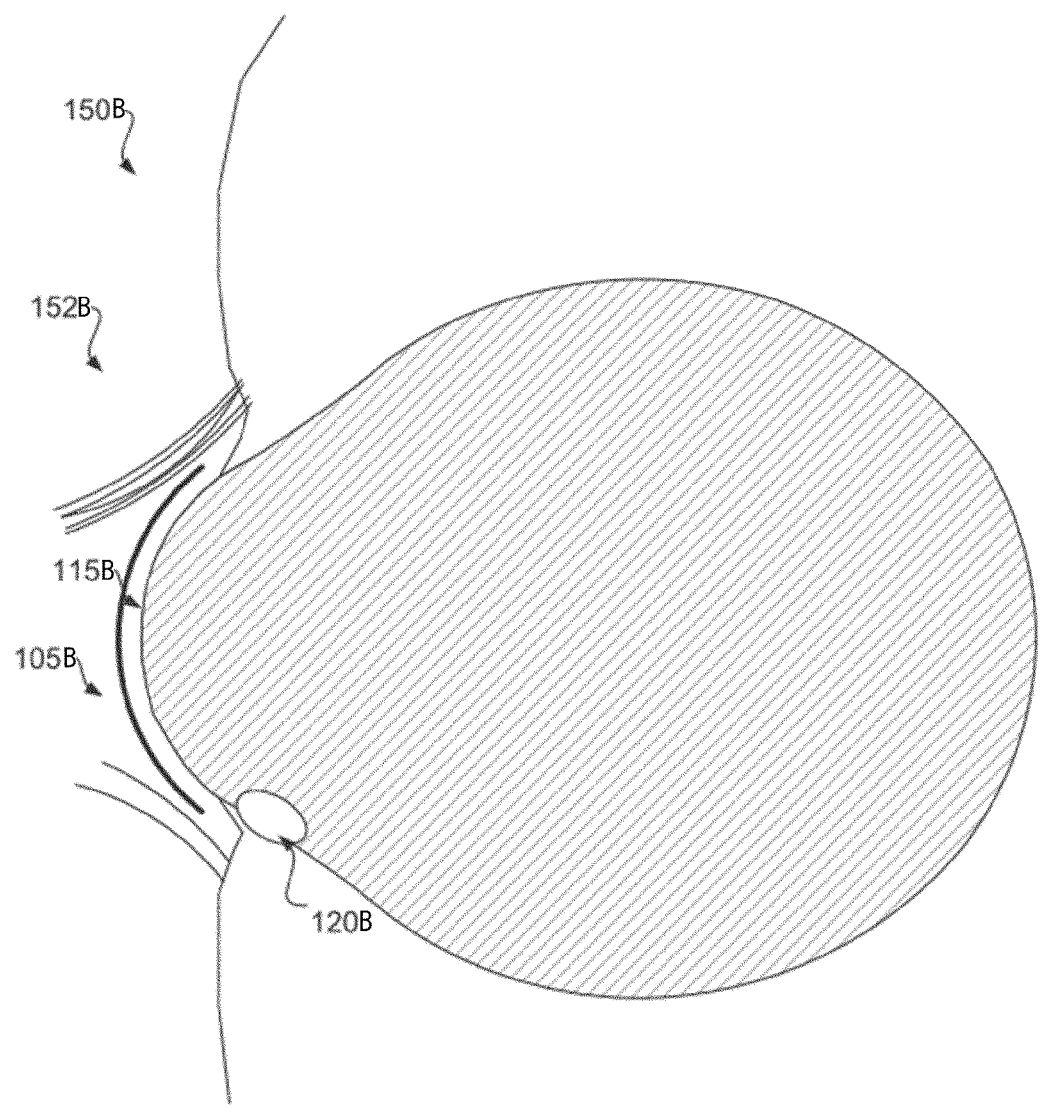
FIG. 25 depicts an example of a contact lens situated on the outside of a human eye.

FIG. 25 depicts an example of a contact lens 105B situated on the outside of a human eye 150B. The contact lens 105B spans the outside surface of the eye 150B, known as the cornea 115B. The cornea 115B is lubricated with tears formed by the lacrimal gland 120B. The contact lens 105B sits atop the cornea 115B and contacts the tears. The contact lens 105B may measure glucose levels in a user through the interaction between the contact lens 105B and the tears on the cornea 115B.

The contact lens 105B may include a hard contact lens, hydrogel lens, silicone hydrogel lens, hydrogel lens, extended wear contacts, spherical contacts, toric contacts, multifocal contacts, monovision contacts, rigid gas permeable lens, toric lens, and the like. In some embodiments, the contact lens 105B may incorporate a colored portion such as to change the appearance of a user's iris.

Any monomer material suitable for use in manufacturing the contact lens 105B can be used. In some embodiments, the monomer is HEMA/GMA. While this example has been described with reference to specific types of monomers that can be used to make the contact lens 105B, any appropriate type of monomer may be used to construct the contact lens 105B. Further, in other examples, silicon, polymers, other types of constituents, or combinations thereof may be used with the monomers or in lieu of the monomers for constructing the contact lens 105B.

In some embodiments, additional materials can be used with the monomer to make the contact lens 105B. Any additives known in the art for improving various characteristics of the contact lens 105B can be used. Examples of additives that may be used in conjunction with the monomer include, but are not limited to, thickeners, dyes, buffers, other types of additives, or combinations thereof. The amount of additive used in conjunction with the monomer may vary based on a variety of factors, including optical properties of the contact lens 105B and the desired characteristics imparted by the additives. Generally speaking, the additives are used in quantities that are sufficiently small that they do not significantly impact the mass of the resulting contact lens 105B.

The contact lens 105B can be formed with any appropriate type of material. In some embodiments, the contact lens may be a hydrogel contact lens 105B or rigid gas permeable (RGP) contact lens 105B. In some embodiments, the contact lens 105B may be a silicone hydrogel contact lens 105B.

Other optical and structural properties of the contact lens 105B can be adjusted and/or fixed to produce a more comfortable and well performing contact lens 105B. In some embodiments, the contact lens 105B includes a fixed base curve. In other words, the contact lens 105B can have the same volume of monomer and the same base curve across a wide range of powers. In some embodiments, the fixed base curve for the contact lens 105B across a range of powers is selected from within a range of from 7.50 to 9.10.

Figure 26:
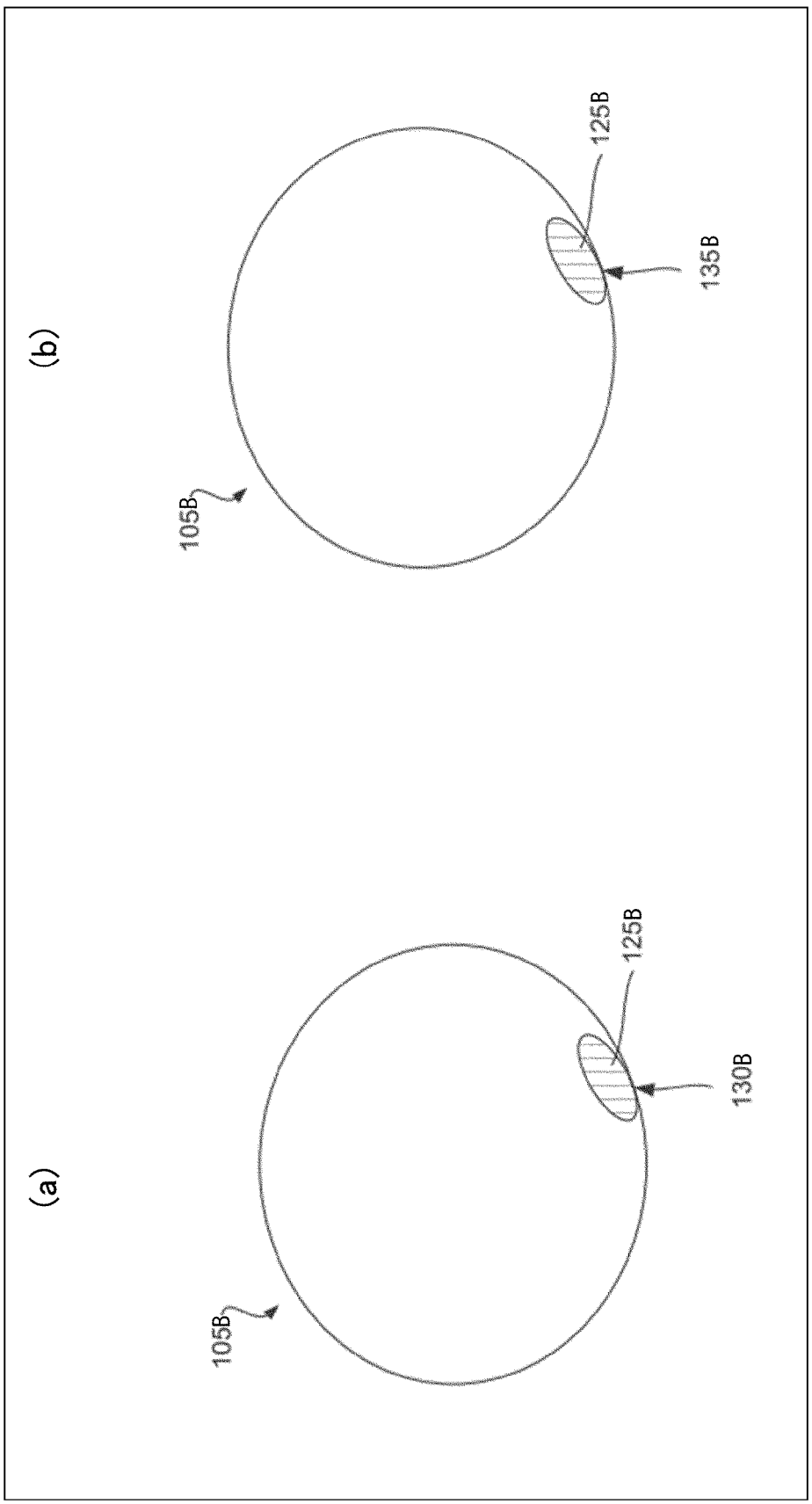
FIG. 26 illustrates a diagram of an example of contact lens.

FIG. 26 depict examples of a contact lens 105B with glucose sensing capabilities. The contact lens 105B is shown with a glucose sensor 125B in a bottom right corner of the lens 105B. The glucose sensor 125B may be positioned at any location on the contact lens 105B. In some embodiments, the glucose sensor 125B may be away from a center of the contact lens 105B to prevent potential interference with a user's vision.

A characteristic of the glucose sensor 125B may change in the presence of glucose. For example, the glucose sensor 125B may contact the tears located on the cornea of an eye (e.g., FIG. 25, cornea 115B of the eye 110B). Glucose may be present in the tears which may be indicative of an overall level of glucose present in the user's body and/or blood. If the amount of glucose present reaches a threshold, the user's health may be in danger. The glucose sensor 125B may alter its appearance to visibly indicate when an excessive amount of glucose is available.

For example, when a user puts on a new contact lens 105B on her cornea 115B, the contact lens 105B may have a first state 130B. An opacity of the first state 130B may be a first, initial state which may be maintained or constant when a first, predetermined amount of glucose is present. For example the first, predetermined amount of glucose may include a range of glucose present in a person's system. The range may encompass what is considered a normal or healthy range for the general population or for a specific user or population of users. In some embodiments, the predetermined amount of glucose may include an amount that corresponds to a blood glucose level of about 80-180 milligrams of glucose per deciliter of blood. This range may include a normal, fasting glucose level and may also incorporate a post-meal glucose level.

In some embodiments, the glucose sensor 125B may maintain the first state 130B when a healthy, acceptable range of glucose is present in a person's tears. In some embodiments, the first state 130B of the glucose sensor 125B may transition to a second state 135B when the glucose level has exceeded a threshold representing healthy glucose concentration. In further embodiments, the glucose sensor 125B may change to a second state 135B when the glucose level has been exceeded for a predetermined time period. For example, if a person's glucose level has surpassed an acceptable range for a truncated period of time, the status of the glucose sensor 125B may remain unchanged. If the person's glucose level has surpassed an acceptable range for a longer duration of time, the status of the glucose sensor 125B may change. In other embodiments, the glucose sensor 125 may transition from a first state 130B to a second state 135B when a predetermined threshold of glucose is detected in the users system.

In some embodiments, the glucose sensor 125B may include a biosensor which may transition from the first state 130B to the second state 135B depending upon a concentration of glucose present in a user's tear fluid. In some embodiments, the glucose sensor 125B may include an enzyme-free biosensor. The enzyme-free biosensor based glucose sensor 125B may be stable at room temperature and within the physiological conditions present in a user's eye. The biosensor may have a first appearance in a first state 130B and a second appearance in a second state 135B.

For example, in some embodiments, the status of the glucose sensor 125B may have two settings of opacity: a first opacity associated with the first state 130B for a first glucose level or range and a second opacity for a second state 135B associated a second glucose level or range. The first opacity may include an opaque or mostly opaque region located within the glucose sensor 125B on the contact lens 105B. The opaqueness may have a color associate with it. For example, the first opacity may include a white opaque region on the contact lens 105B. The size and shape of the opaque region may vary based on size of the contact lens and other factors. A second opacity may be mostly and/or completely transparent.

In some embodiments, the glucose sensor 125B may include a material which changes opacity in the presence of glucose. In some examples, the material may change opacity by a chemical reaction with glucose in a user's tear fluid. In some examples, the material may change opacity by a chemical reaction or series of chemical reactions with glucose and/or another chemical in a user's tear fluid. In some embodiments, the glucose sensor 125B may be a boronic acid copolymer biomaterial. The glucose sensor 125B may react with glucose and change optical characteristics. In some embodiments, the glucose sensor 125B may include an enzyme-free material.

In some embodiments, the glucose sensor 125B may change in color. In further embodiments, the glucose sensor 125B may change opacity and color. For example, in a healthy glucose range, the glucose sensor 125B may have a first color. In a second, unhealthy, glucose range, the glucose sensor 125B may include a second color. In some embodiments, the glucose sensor 125B may transition slowly to the second color to indicate a rise in glucose. For example, the first color may include red and the second color may include blue. As the user's glucose level rises, the glucose sensor 125B may change to varying shades of purple as the red color fades and the blue color emerges. In further embodiments, the opacity and color of the glucose sensor 125B may change. For example, the first state 130B may have a first opacity and a first color, for example white, associated with it. As the glucose level rises to an unhealthy level, the opacity of the first state 130B may begin to fade and, at the same time, the color of the glucose sensor 125B may change. The initial color and end color or opacity may include any combination of colors or opacity. In some cases, the first and second colors and opacity are different enough to be easily distinguishable with the naked eye. In other examples, opacity sensors and/or color sensors are used to determine when the area changes its state.

In some embodiments, the amount of glucose present in a user's system may be easily characterized by viewing the glucose sensor 125B. For example, a user may look in a mirror and be able to visibly see if the first state 130B or second state 135B, or tertiary indicator, are present to quickly establish if the user has a healthy or unhealthy range of glucose in their system. Multiple observation methods may be utilized. For example, a third party may view the user's contact lens 105B and determine if the first or second state 130B, 135B is present in the glucose sensor 125B. A user may also use an image capturing device such as a mobile device or laptop to photograph their eye, with the contact lens 105B, and visibly distinguish between the first and second states 130B, 135B. The user may view the image herself or may transmit the image to a third party for observation or recordation purposes.

Figure 27:
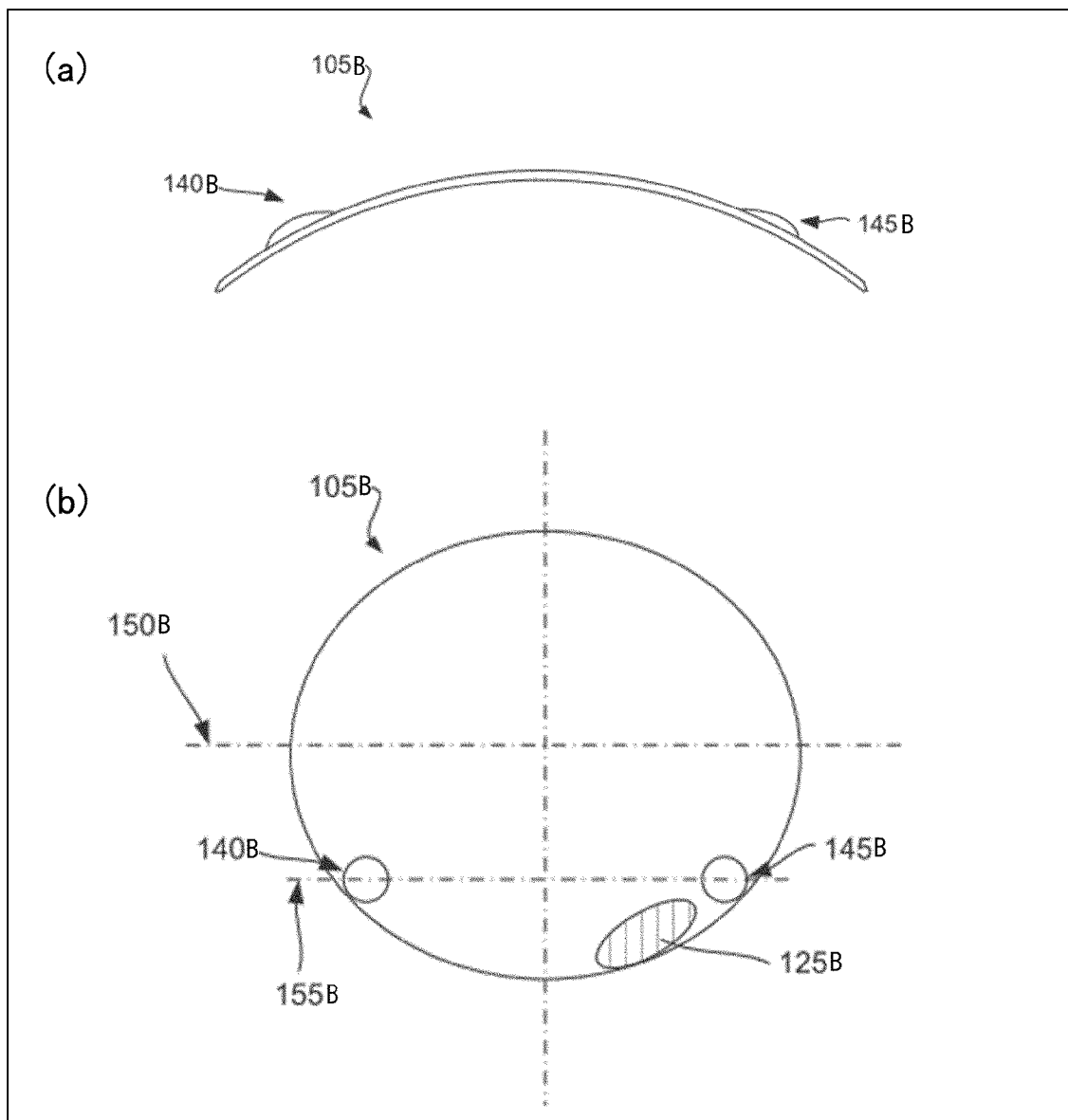
FIG. 27 illustrates a diagram of an example of contact lens.

In further embodiments, the contact lens 105B may align the glucose sensor 125B to be below an eyelid when worn in a user's eye. The contact lens 105B may incorporate one or more features to align the contact lens 105B such that the glucose sensor is visible and may be observed by the user or a third party. For example, in FIG. 27 displays a contact lens 105B with one or more protrusions 140B, 145B. The protrusions 140B, 145B may align the contact lens 105B in the eye in a desired orientation.

For example, a first protrusion 140B may be larger than a second protrusion 145B. In some embodiments, the protrusions 140B, 145B may extend from the contact lens 105B by about 0.1 mm to about 3 mm, from about 0.25 mm to about 3 mm, from about 0.5 mm to about 3 mm, or from about 1 mm to about 3 mm. In some examples, one or more protrusions 140B, 145B may extend more than about 3 mm from the contact lens 105B. In some examples, one or more protrusions 140B, 145B may extend less than about 0.1 mm from the contact lens. The protrusions 140B, 145B may be multiple shapes and sizes. The protrusions 140B, 145B may be substantially symmetric or may be asymmetric.

When the contact lens is in use, the eyelid will interact with the contact lens 105B. As the eyelid closes, the eyelid may contact one of the protrusions 140B, 145B first. Depending upon the orientation of the contact lens 105B in the eye, the eyelid may contact either the first protrusions 140B or second protrusion 145B. As the eyelid continues to move downward, the eyelid will contact a protrusion, for example the first protrusion 140B. The first protrusion 140B will move downward with the eyelid and, eventually, the eyelid will contact the second protrusion 145B. When the eyelid contacts both protrusions 140B, 145B, the contact lens 105B will rotate until the protrusions 140B, 145B are substantially level within the eye. When both protrusions 140B, 145B contact the eyelid, the eyelid overcomes the resistance of the protrusions 140B, 145B and the eyelid slips over the protrusion 140B, 145B such that the contact lens 105B is oriented so that the glucose sensing area is away from the eyelid.

The protrusions 140B, 145B may be located substantially centric to or below a centerline 150B of the contact lens 105B. This may enable the protrusions 140B, 145B to align the contact lens 105B within the eye such that the glucose sensor 125B is visible and is not hidden under a user's eyelid. For example, the glucose sensor 125B may be located substantially below either the centerline 150B of the contact lens 105B or a centerline 155B between the protrusions 140B, 145B.

Figure 28:
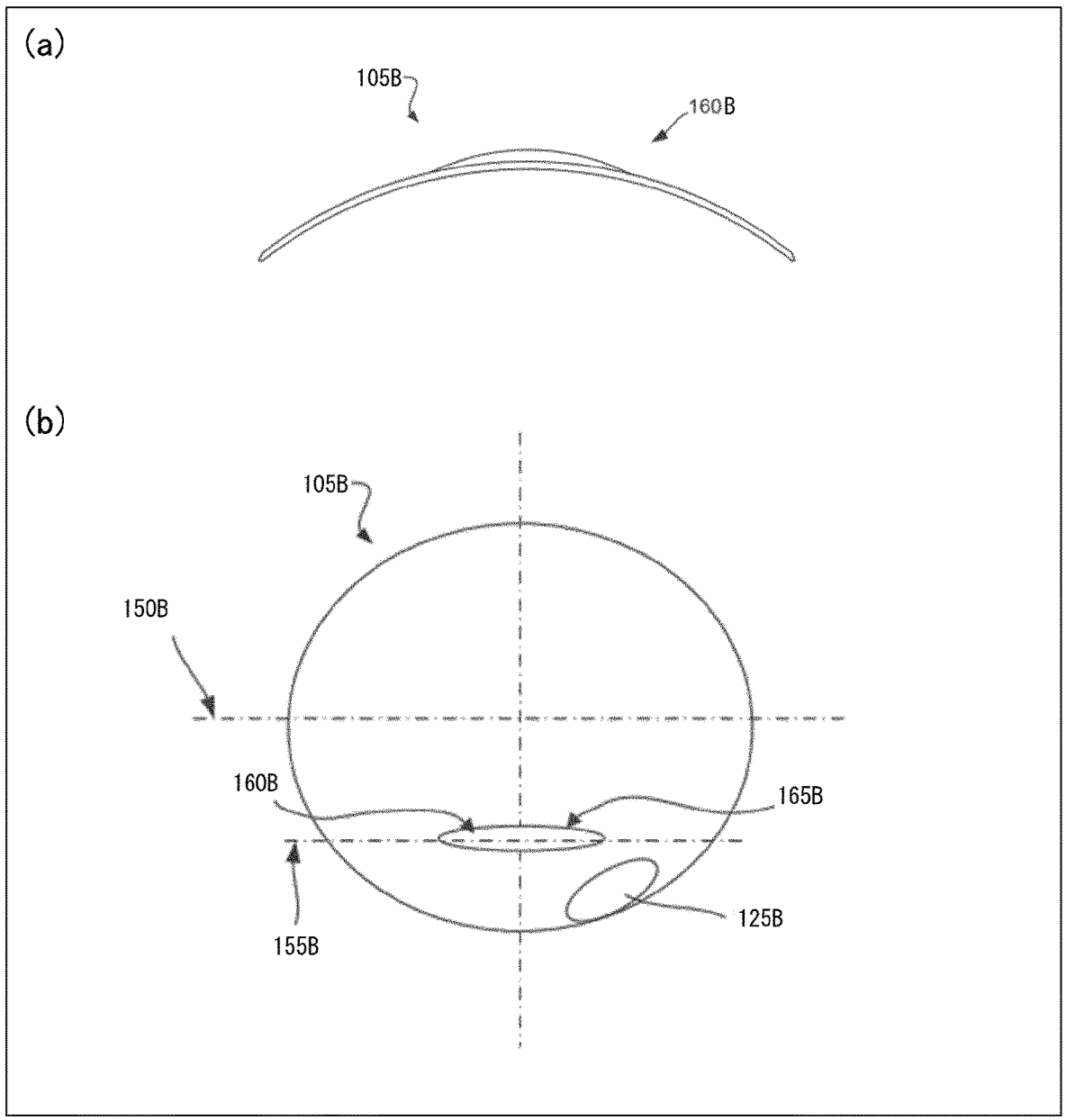
FIG. 28 illustrates a diagram of an example of contact lens.

FIG. 28 depicts an alternative embodiment of a protrusion 160B. The protrusion 160B may be a single raised member on the contact lens 105B. The protrusion 160B may be located below the centerline 150B of the contact lens 105B. The protrusion 160B may have a substantive width such that the eyelid may contact an upper surface 165B of the protrusion 160B, the eyelid may orient the contact lens 105B into a desired rotational position within the eye. The desired orientation may locate the glucose sensor 125B below the eyelid such that the user or third party may view the glucose sensor 125B easily.

Figure 29:
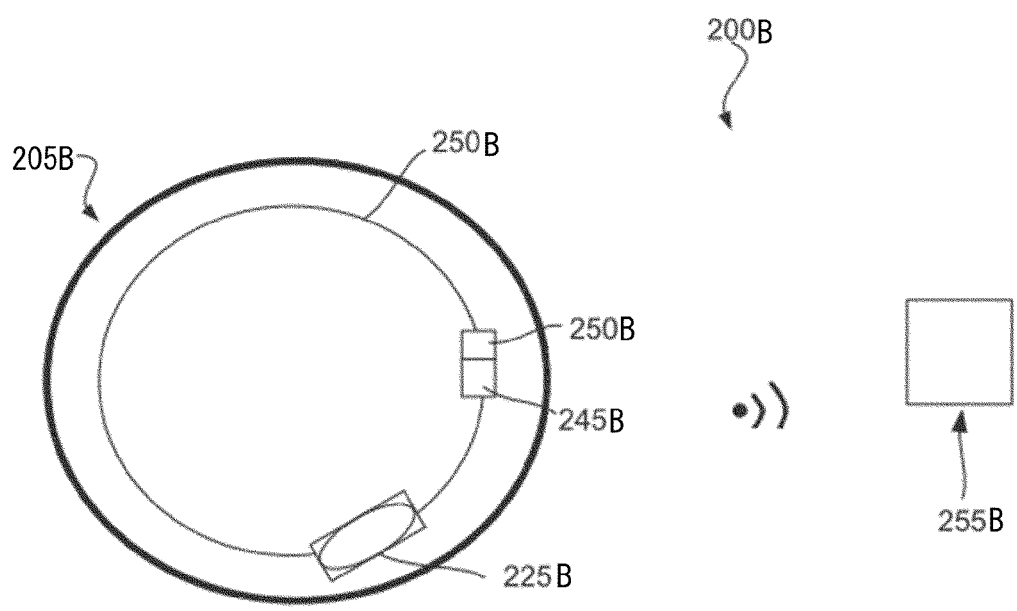
FIG. 29 illustrates a diagram of an example of contact lens.

FIG. 29 depicts an example of a smart contact lens system 200B for glucose sensing. The smart contact lens system 200B may include a smart contact lens 205B. An example of smart contact lens 205B may include the contact lens 105B described with reference to FIGS. 25-28. The smart contact lens 205B may include a glucose sensor 225B. The glucose sensor 225B may be identical to or similar to the glucose sensor 125B described with reference to FIGS. 26-28. In some embodiments, the smart contact lens 205B may include an antenna 240B, an energy source 245B, and a wireless transmitter 250B. In some embodiments, a wireless receiver 255B may be remote from the contact lens 205B. The glucose sensor 225B may transmit a message to the wireless receiver 255B via the antenna 240B.

Figure 30:
FIG. 30 illustrates a cross sectional view of an example of glucose sensor.

The glucose sensor 225B, shown in a side view in FIG. 30, may include a glucose sensing area 260B and an optical sensor 265B. The glucose sensor 225B may include an upper, outer facing layer of the glucose sensing area 260B. The glucose sensing area 260B may be located on the smart contact lens 205B facing away from the eye. Underneath the glucose sensing area 260B is the optical sensor 265B. For example, the optical sensor 265B may be between the glucose sensing area 260B and the user's eye. The glucose sensing area 260B may be similar to the glucose sensor 125B described with reference to FIGS. 26-28. The glucose sensing area 260B may include a first state and a second state. The first state and second state may be similar to the first state 130B and second state 135B described with reference to FIG. 26.

The optical sensor 265B may initially be hidden or obscured by the glucose sensing area 260B in a first state. As the glucose sensing area 260B transitions from the first state to the second state, the optical sensor 265B may gradually become partially or fully exposed. As the optical sensor 265B becomes exposed, the optical sensor 265B may begin to take measurements.

For example, the optical sensor 265B may include a thin-film solar cell. The optical sensor 265B may include one or more thin layers of thin film of photovoltaic material on a substrate. The substrate may include a plastic. The optical sensor 265B may be a few nanometers thick up to a tens of micrometers thick. As the solar cell is exposed to light, the solar cell operating as the optical sensor 265B, may begin to charge the energy source 245B. As the energy source 245B becomes charged, the energy source 245B may power the antenna 240B and begin to transmit one or more messages or communications to the wireless receiver 255B. The messages may include predetermined communications regarding a level of glucose concentration in a user's tear fluid. In some embodiments, the message may be a simple pinging upon the optical sensor 265 being exposed.

In some embodiments, the optical sensor 265B may additionally and/or alternatively include a photometer sensor. The optical sensor 265B may measure light intensity or the optical intensity. The optical sensor 265B may measure illuminance, irradiance, light absorption, scattering of light, reflection of light, fluorescence, phosphorescence, luminescence, and the like. The optical sensor 265B may detect light using at least one of a photoresistors, photodiode, photomultipliers, or the like. In some embodiments, the optical sensor 265B may measure an amount of light after it has passed through a filter or monochromator. The use of a filter or monochromator may enable the optical sensor 265B to determine light intensity at defined wavelengths or to analyze a spectral distribution of the light.

In other embodiments, the optical sensor 265B may measure individual photons rather than incoming flux. Flux may include spectral flux or spectral power of the light that reaches the optical sensor 265B. In some embodiments, the optical sensor 265B may include a reflectance photometer which may measure the reflectance of a surface as a function of wavelength.

In some embodiments, the optical sensor 265B may alternatively or additionally measure the absorption of light of a given wavelength. For example, the optical sensor 265B may measure the concentration of a colored substance in a solution. The optical sensor 265B may include an absorption photometer to measure ultraviolet and visible ranges of specific light wavelengths.

The optical sensor 265B, as a photometer, may transmit a message to the wireless receiver 255B through the antenna 240B and energy source 245B. For example, as the optical sensor 265B is exposed, the optical sensor 265B may begin measuring various optical qualities as discussed. When the optical qualities reach a predetermined threshold, the optical sensor 265B may transmit a message to the wireless receiver 255B. For example, the optical sensor 265B may slowly reach a threshold measurement as the optical sensor 265B is slowly exposed as the glucose sensing area 260B transitions from a first state to a second state. Therefore, the optical sensor 265B may not directly transmit a glucose concentration level but may indicative of a glucose concentration based on the exposure of the optical sensor 265B as the glucose sensing area 260B transitions from a first state to a second state.

In some embodiments, the optical sensor 265B may act as a capacitor. For example, the optical sensor 265B may store a charge which may be released when the optical sensor 265B is exposed, for example, when the glucose sensing area 260B transitions from the first state to the second state. As the optical sensor 265B, as a capacitor, is exposed, the capacitor may release a charge and may power the energy source 245B. Once the energy source 245B is powered, the antenna 240B may transmit a message to the wireless receiver 255B.

The energy source 245B may include a battery. The battery may be rechargeable. The energy source 245B may initially have a stored charge or the energy source 245B may be charged by the optical sensor 265B. The energy source 245B may include graphene. In some embodiments, the energy source 245B may be printed to a surface of the contact lens. The energy source 245B may be graphene printed battery. In some embodiments, the energy source 245B may be fully printable, may include a planar architecture. In some embodiments, the energy source 245B may be flexible and have a long shelf-life. The energy source 245B may function in a moist environment. In some embodiments, the energy source 245B may have approximately one microampere per square millimeter capacity per unit area. The energy source 245B may include approximately twenty-five microampere per cubic centimeter capacity per unit volume.

Figure 31:
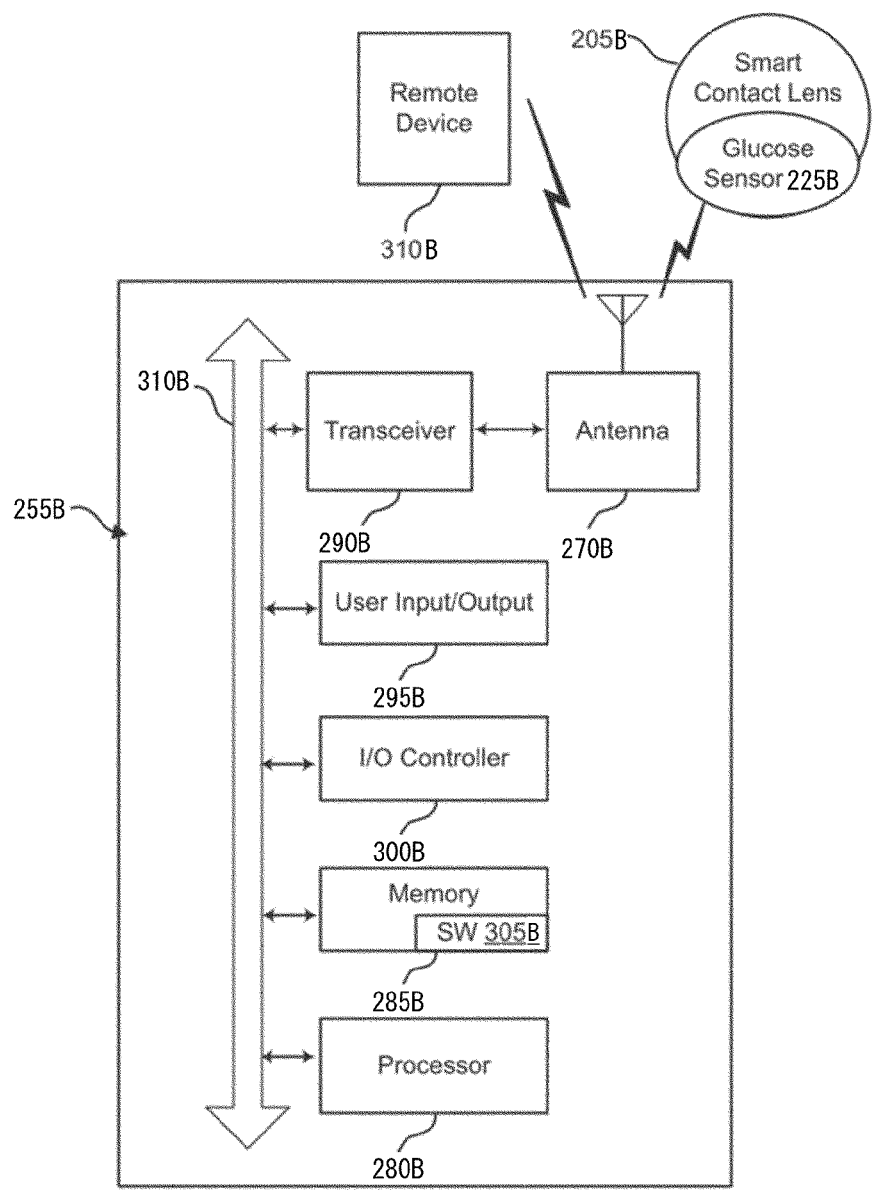
FIG. 31 illustrates a block diagram of an example wireless receiver.

An embodiment of the wireless receiver 255B is shown in FIG. 31. The wireless receiver 255B may include an antenna, and a power source. The wireless receiver 255B may also include a processor module 280B, and memory 285B (including software/firmware code (SW) 305B), an input/output controller module 300B, a user input/output module 295B, a transceiver module 290B, and one or more antennas 270B each of which may communicate—directly or indirectly—with one another (e.g., via one or more buses 310B). The transceiver module 290B may communicate bi-directionally—via the one or more antennas 270B and/or wireless links—with the smart contact lens 205B. For example, the transceiver module 290B may receive communications from and/or communicate bi-directionally with one or more smart contact lenses 205B. In some embodiments, the transceiver module 290B may communicate bi-directionally with a remote device 315B. The remote device may include a mobile device, laptop, or other device. The transceiver module 290B may modulate packets to send to the one or more antennas 270B for transmission, and to demodulate packets received from the one or more antenna 270B. While the wireless receiver 255B may include a single antenna 270B, the wireless receiver 255B may also have multiple antennas 270B capable of concurrently transmitting or receiving multiple wireless transmissions.

In some embodiments, the wireless receiver 255B may alternatively connect to a remote device via a wired transmission. In some embodiments, one element of the wireless receiver 255B (e.g., one or more antennas 270B, transceiver module 290B, etc.) may provide a connection using wireless techniques, including digital cellular telephone connection, Cellular Digital Packet Data (CDPD) connection, digital satellite data connection, and/or another connection. The signals associated with wireless receiver 255B may include wireless communication signals such as radio frequency, electromagnetics, local area network (LAN), wide area network (WAN), virtual private network (VPN), wireless network (using 802.11, for example), 345 MHz, Z-WAVE (registered trademark), cellular network (using 3G and/or LTE, for example), and/or other signals. The one or more antennas 270B and/or transceiver module 290B may include or be related to, but are not limited to, WWAN (GSM, CDMA, and WCDMA), WLAN (including BLUETOOTH (registered trademark) and Wi-Fi), WMAN (WiMAX), antennas for mobile communications, antennas for Wireless Personal Area Network (WPAN) applications (including RFID and UWB). In some embodiments, each antenna 270B may receive signals or information specific and/or exclusive to itself. In other embodiments, each antenna 270B may receive signals or information not specific or exclusive to itself.

In some embodiments, the user input output module 295B may include an audio device, such as an external speaker system, a visual display, and/or an input device. A speaker may provide an audible output when a glucose concentration has reached a predetermined level. For example, once the glucose concentration reaches an unhealthy level that is detected by the glucose sensor (e.g., glucose sensor 225B), the wireless receiver 255B may receive a communication and may sound an audible alert to the user. In some embodiments, a visual display such as a screen or light may additionally and/or alternatively alert the user of an unhealthy glucose concentration.

One or more buses 310B may allow data communication between one or more elements of the wireless receiver 255B (e.g., processor module 280B, memory 285B, I/O controller module 300B, user interface module 295B, etc.).

The memory 285B may include random access memory (RAM), read only memory (ROM), flash RAM, and/or other types. The memory 285B may store computer-readable, computer-executable software/firmware code 305B including instructions that, when executed, cause the processor module 280B to perform various functions described in this disclosure (e.g., receiving an alert concerning glucose concentration, communicating an alert to the user, and the like).

Figure 32:
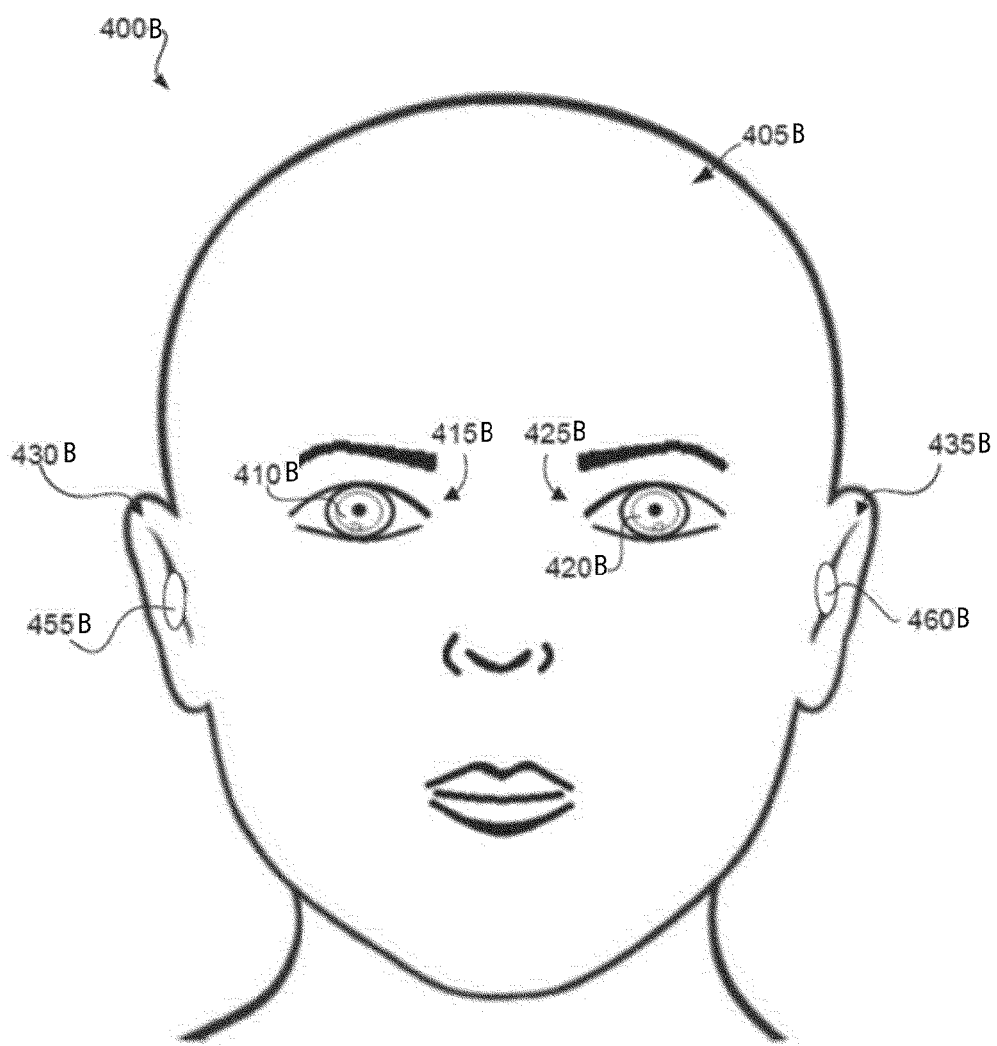
FIG. 32 illustrates a diagram of an example contact lens system.

FIG. 32 is a schematic of a smart contact lens system 400B being worn by a user 405B. The user 405B may have a first contact lens 410B in a first eye 415B and a second contact lens 420B in a second eye 425B. A wireless receiver 455B may be in a first ear 430B. In some embodiments, a second wireless receiver 460B may be in a second ear 435B. The first contact lens 410B may be a smart contact lens 205B as discussed with reference to FIGS. 29-30. The second contact lens 420B may additionally be a smart contact lens 205B or may be a control contact lens.

For example, each contact lens 410B, 420B may include a smart contact lens 205B and may detect a glucose concentration present in a tear fluid of the user 405B. The wireless receivers 455B, 460B may be in a respective ear closest to the coupling contact lens 410B, 420B. Having the wireless receiver 455B, 460B mountable in or proximate the user's ear 430B, 435B provides a consistent short distance between the contact lens 410B, 420B and the wireless receiver 455B, 460B. The consistent distance provides predictability in the strength of signal needed from the contact lens 410B, 420B to the wireless receiver 455B, 460B. Having a wearable wireless receiver 455B, 460B also provides that the receiver will remain within the predetermined distance. The wireless receiver 455B, 460B may alert the user to an unhealthy glucose concentration and/or may transmit a message to a device associated with the user to communicate a glucose concentration.

In some embodiments, both contact lens 410B, 420B are smart contact lenses 205B and provide a dual detection system for increasing glucose concentrations. In alternative embodiments, one of the contact lens, for example, the second contact lens 420B may include a control contact lens. The control contact lens may include an antenna and a power source similar to the smart contact lens 205B. However, the glucose sensor may be replaced with the optical sensor. For example, instead of the glucose sensor, the control contact lens may include the optical sensor without the glucose sensing area. By having a contact lens with only the optical sensor, the optical sensor may transmit a message to the wireless receiver to alert the user that their contact lens is functioning properly. In alternative embodiments, one or more of the contact lenses 410B, 420B may include the glucose sensor as well as an additional optical sensor. The additional optical sensor may continuously communicate a first message to the wireless receiver 455B, 460B ensuring the components of the contact lens 410B is working properly. Furthermore, the use of a control contact lens allows the overall system to identify a differential in light or energy received by the optical sensor that includes the glucose sensor, relative to the optical sensor configured without the glucose sensor. This can reduce false positives based on changes in ambient light or environment experienced by the user.

Figure 33:
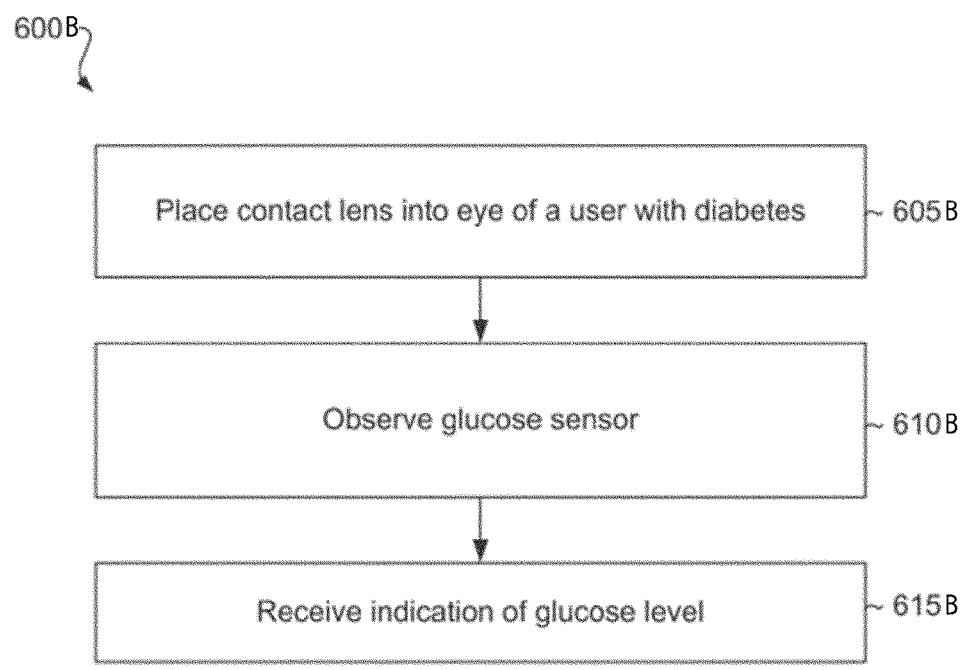
FIG. 33 illustrates a block diagram of an example of a method of using a glucose sensor.

FIG. 33 illustrates an example of a method 600B of using a contact lens. In this example, the method 600B includes placing a contact lens onto an eye of a user with diabetes 605B, observing the glucose sensor 610B, and receiving an indication of a glucose level of the user 615B.

At block 605B, the contact lens is placed in the eye of a user. The use of the sensor may be most effective if the user has a confirmed case of diabetes or signs indicative of someone with diabetes. At block 610B, the glucose sensor is observed. The user may observe their own glucose sensor via a minor, or picture, e.g. a selfie or other self-photograph, reflection, or other method of viewing one-self. At block 615B, the method 600B may include receiving an indication of a glucose level. In some embodiments, the indication may include a change in the glucose sensor from the first state to the second state. For example, the glucose sensor may have a visible first state which may transition to a second state. The transition between the first state and second state may indicate to the user or a third party that the glucose concentration has reached an unhealthy level. In other embodiments, a third party may view the glucose sensor and communicate to the user. In another embodiment, the glucose sensor may be a smart sensor and may automatically detect a level of glucose in the user's system. The glucose sensor may communicate to a remote device. The remote device may connect or communicate to the user to alert the user of a glucose concentration. In some embodiments, a lack of communication from the glucose sensor may indicate an acceptable glucose level in the user's system. Once the sensor structure begins to communicate with remote sensor, the user may be alerted to an unhealthy glucose concentration level in their system.

Embodiment 4

The principles described herein include incorporating a tonometer system including a test body into a contact lens that can be worn on a user's eye. While the contact lens is worn on the user's eye a tonometer system can wirelessly measure the absolute intraocular pressure of the eye by measuring the rebound of the test body on the eye surface. In some cases, the rate of deceleration of the test body caused by the physical properties of the eye is detected and used to calculate the absolute intraocular pressure of the eye. In some cases, the rate of return of the eye and/or lens from an expanded state to a non-expanded state is measured and used to calculate the absolute intraocular pressure of the eye. The rate of deceleration of the testbody and/or the rate of return of the contact lens or eye can be measured by a sensor which is situated on or incorporated into the contact lens and which can wireles sly transmit the relevant data to a secondary device, such as an electronic device. In some cases, the tonometer system may include the sensor. In some cases this sensor may be a variable capacitance sensor, and may measure the mechanical strain of the contact lens while on the eye.

In some cases, the contact lens may comprise lens material and a test body in contact with the lens material. The test body may be disposed on a surface of the lens material, or it may be incorporated into the lens material. In some embodiments, the test body may be positioned outside of the optic zone of the contact lens that is configured to correct the user's vision. In this type of example, the test body may not interfere with or obstruct a user's vision while wearing the contact lens. In some cases, a tonometer system may include a test body to exert force on the eye. In some cases, the test body may be a selectively expandable material which may exert a force on the eye when the expandable material is in an expanded state. That is, the expandable material may expand under certain conditions and may return to an initial state when those conditions are stopped or removed. For example, in some cases the selectively expandable material may be a magnetoresponsive elastomer. The magnetoresponsive elastomer material may expand in the presence of a magnetic field, and may return to an initial state when the magnetic field is removed.

In certain embodiments, the contact lens may further include a sensor, for example as a component of the tonometer system that can detect certain characteristics of the test body and/or contact lens to determine the absolute intraocular pressure of the eye. For example, the contact lens may include a sensor that can measure the amount of time it takes for the test body to return from an expanded state to the initial state. In some cases, the contact lens may include a sensor that can measure the deceleration of the test body caused by the eye as it enters the expanded state. The sensor can wirelessly communicate this information to a secondary device, such as an electronic device, which can manage sensor data in real time and calculate the absolute intraocular pressure of the eye, a relatively pressure of the eye, another parameter of the eye, or combinations thereof. In some cases, the sensor may be a transparent variable capacitance sensor that is capable of measuring the mechanical strain of the contact lens on the eye by correlating its changes in capacitance when the expandable material is expanded verses when the expandable material is in the initial state. As used herein, the term "absolute intraocular pressure" may refer to the total fluid pressure inside an eye, whereas the term "relative intraocular pressure" may refer to an amount of deviation or fluctuation from a baseline intraocular pressure value.

A contact lens including a test body may be manufactured by a variety of methods, including spin coating, dip coating, printing, stamping, or some combination thereof. In certain embodiments contact lens material may be provided and the test body may be deposited or formed on the lens material in a layer-by-layer deposition process. Thus, the test body may comprise one or more polymer layers which are deposited or formed on the lens material by printing, spin coating, and/or dip coating. However, in some other embodiments the contact lens may be manufactured by a stamping process, and the test body is deposited or formed on a mold, attached to a stamp or tool, and then deposited on the contact lens material. The stamping process may greatly reduce the processing or manufacturing time for the contact lens because the test body can be deposited or formed separately from the lens material, allowing for parallel processing lines. Once both the lens material and test body have been formed, they can be joined by stamping. In some cases, the contact lens body is formed through a spin casting process, and at least a portion of the circuitry for measuring the eye's intraocular pressure is manufactured separately and joined to the spin casted contact lens body.

Figure 34:
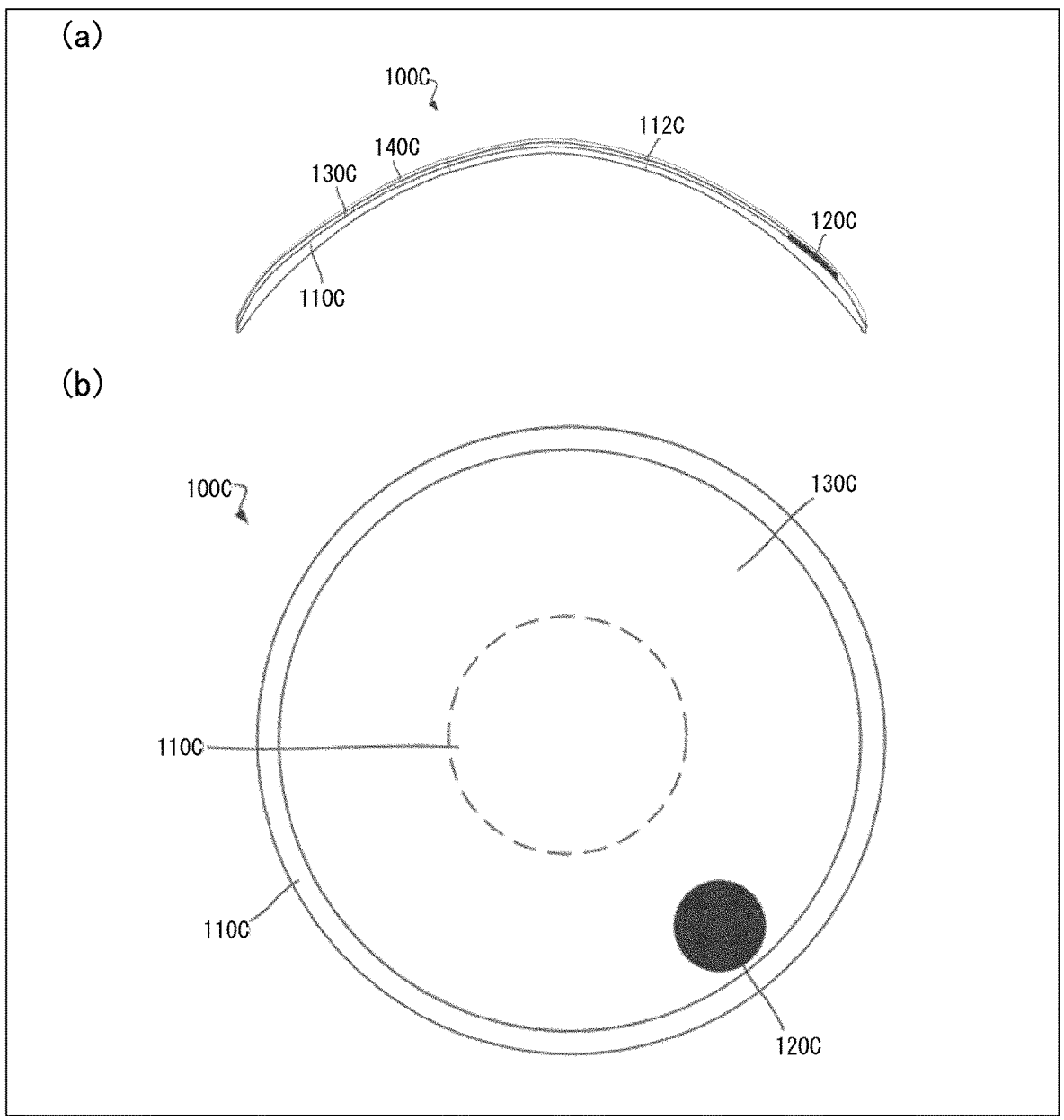
FIG. 34 illustrates an example contact lens incorporating a tonometer system.

FIG. 34 depict an example of a contact lens 100C comprising a lens material 110C and a tonometer system including a test body 120C disposed thereon. The test body 120C may be disposed outside of the optic zone 112C of the contact lens 100C. The lens material 110C may comprise any material suitable for use as a contact lens. That is, in some examples, the lens material 110C may comprise a typical hydrogel contact lens. For example, in some embodiments the lens material 110C may comprise a transparent polymer material, such as a hydrogel. In some cases the lens material 110C may comprise a silicone hydrogel material.

In some embodiments, the test body 120C may be disposed completely or partially within the optic zone 112C of the contact lens 100C. In some of these cases, the test body 120C may be transparent and may not distort or interfere with the user's vision, at least when in an initial state. In some cases, however, a test body 120C positioned at least partially within the optic zone 112C of the contact lens 100C may interfere with or distort a user's vision when in an expanded state and/or the initial state.

The test body 120C may selectively exert the force on the eye sufficient to obtain an intraocular pressure value via rebound tonometry. In some embodiments, the test body 120C may be a selectively expandable material. That is, the test body 120C may be a material that expands under a predetermined condition or set of conditions, and returns to its initial state when the condition or conditions are removed. In certain embodiments, the expandable material may be a polymer material, and in some cases the expandable material may be an elastomer. In some embodiments, the expandable material may be a hydrogel material.

In some cases, the expandable material may comprise a magnetoresponsive material that expands in the presence of a magnetic field and returns to the initial state when no longer in the presence of the magnetic field or within the presence of a magnetic field with a sufficient strength to expand the material. In these cases, the expandable magnetoresponsive material may include a polymer film including a plurality of molecular microchains which may be preferentially aligned with a magnetic field when the material is exposed to a magnetic field of sufficient strength. In some embodiments the expandable magnetoresponsive material may include aligned magnetic microchains throughout an entire thickness of the polymer film. In some embodiments, the aligned magnetic microchains may be formed upon the magnetophoretic transport and assembly of microparticles during polymer curing of the expandable magnetoresponsive material, for example during formation of the test body 120.

In some embodiments, the expandable magnetoresponsive material may include a plurality of magnetic nanocrystals embedded in a polymer matrix, such as a polyvinyl alcohol (PVA) matrix. In some embodiments, the expandable magnetoresponsive material may include an elastomer, such as a silicone elastomer. In some examples, the elastomer may be a matrix in which magnetic microchains are dispersed. In some embodiments the magnetic microchains may be formed of particles having an average size of less than about 500 microns, less than about 250 microns, less than about 100 microns, less than about 50 microns, less than about 10 microns, or smaller. In some embodiments, the particles forming the magnetic microchains may be ferromagnetic particles, such as metallic ferromagnetic alloy particles. In some examples, these particles may include one or more of Nd, Fe, Pr, Co, B, Dy, Ga, or other elements. In some embodiments, the magnetic particles may be from about 1 wt % to about 50 wt % of the cured magnetoresponsive material. In some embodiments, magnetic microchains may be formed in an elastomeric matrix by applying an external magnetic field to the magnetoresponsive material while it is being cured or formed so that the magnetic particles are transported and aligned to form microchains having a substantially uniform orientation throughout the cured elastomeric matrix.

In some embodiments, when the expandable magnetoresponsive material is not exposed to a magnetic field of sufficient strength to expand the material, for example less than about 100 mT, less than about 10 mT, or less than about 1 mT or lower, the material may comprise a homogenous dispersion of microparticles or polymer blocks.

In some cases, the tonometer system and/or test body 120C do not comprise separate mechanical moveable parts. That is, in some embodiments the tonometer system and/or test body 120C may not comprise parts which move or slide with respect to one another. For example, in some cases a tonometer system and/or test body 120C may not include a slideable or moveable central piece, such as a magnet and housing piece, such as a coil, through which the central piece may move. In some embodiments, the tonometer system and/or test body 120C may not comprise a permanent magnet and/or an electromagnet.

The test body 120C may have a diameter in an initial state of from about 1 millimeters to about 3 millimeters. In some cases the test body 120C may have a diameter of about 2 millimeters. The test body 120C may have a thickness of about from about 25 micrometers to about 200 micrometers, or from about 50 micrometers to about 100 micrometers. It has been advantageously found that a test body 120C having a thickness of, for example, less than 100 micrometers allows for the ability to measure the absolute intraocular pressure of the eye without causing discomfort when the contact lens 100C is on the eye. Although the test body 120C is depicted in FIG. 34 as approximately circular in shape, other shapes are expressly contemplated. For example, in some embodiments the test body 120C may be elliptical, rectangular, or irregular shape. In some cases, the test body 120C may have a surface area of from about 1 square millimeter to about 10 square millimeters. In some cases, the test body 120C may have a surface area of about 4 square millimeters. In some situations, the surface area of the tonometer may be less than 10 percent of the contact lens' surface area, more than 10 percent of the contact lens' surface area, more than 20 percent of the contact lens' surface area, more than 30 percent of the contact lens' surface area, more than 50 percent of the contact lens' surface area, more than another percentage of the contact lens' surface area, or combinations thereof.

The contact lens material 110C may include an optic area or zone 112C positioned at the center of the contact lens 100C. The optic zone 112C is typically about the same size as the pupil of the eye in low-light conditions, for example the optic zone may have a diameter of about 10 millimeters. The optic zone 112C contains the corrective power of the contact lens 100C, if any corrective power is present. According to some embodiments, the test body 120C described herein is positioned on the contact lens material 110C outside of the optic zone 112C. In some cases, the test body may be positioned substantially adjacent to the optic zone 112C, however in some other cases the tonometer may be positioned near an edge of the lens material 112C, or any position therebetween.

In some embodiments, the tonometer system of the contact lens 100C may further comprise a sensor 130C. The sensor 130C may be in contact with the lens material 110C. In some cases, the sensor 130C may detect and/or wirelesly transmit information regarding the rate of change of the mechanical strain of the contact lens 110C as the test body 120C transitions from an expanded state to an initial state. In some cases, the sensor 130C may detect and/or wirelessly transmit information regarding the deceleration of the test body 120C caused by the eye as the expandable material enters the expanded state. The sensor 130C may be, for example, a variable capacitance sensor. The sensor 130C thus may include a parallel plate capacitor and an antenna structure. The parallel plate capacitor of the sensor 130C may include at least a first transparent conductive layer and a second transparent conductive layer, with a dielectric layer disposed therebetween. The antenna connected to the sensor 130C may be electrically connected to each of the conductive layers to thereby form an electrical oscillator. In some cases, the natural frequency of the electrical oscillator comprising the sensor 130C may correspond to the amount of mechanical strain experienced by the contact lens 100C, for example due to the expansion of the test body 120C. Accordingly, a secondary electronic device, such as a vector network analyzer (VNA) may be used to detect the mechanical strain of the contact lens 100C via the sensor 130C in order to determine the rate of change of the mechanical strain and the absolute intraocular pressure of the eye.

In some cases, the contact lens 100C may further comprise an encapsulation layer 140C disposed over the test body 120C and/or sensor 130C. The encapsulation layer 140C may be in direct contact with the test body 120C. In some examples, the encapsulation layer 140C may comprise a polymer material, such as a hydrogel. In some cases the encapsulation layer 140C may comprise a silicone hydrogel material and may be the same material as the lens material 110C. The encapsulation layer 140C may have a thickness of from about 0.1 micrometers to about 20 micrometers, from about 0.5 micrometers to about 15 micrometers, or from about 1 micrometers to about 10 micrometers.

Figure 35:
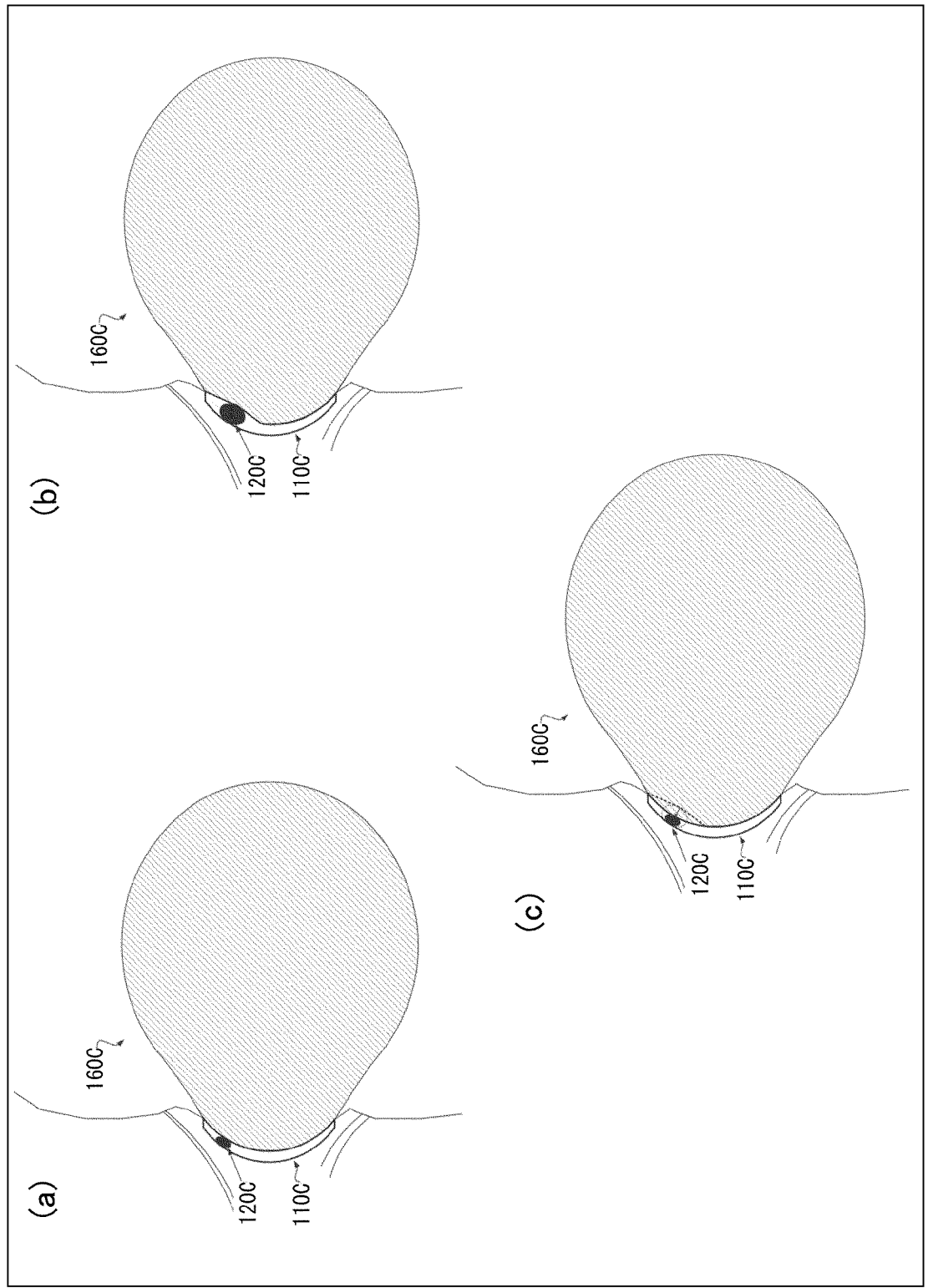
FIG. 35 illustrates a cross sectional view of an example contact lens including a test body.

FIG. 35 (a) shows a cross sectional view of contact lens 100C, including test body 120C in an initial state, positioned on the eye 160C of a user. As described herein, the test body 120C is positioned outside the optic zone 112C of the eye. FIG. 35(b) shows the contact lens 100C and test body 120C positioned on the eye 160C while the test body 120C is, for example, exposed to a magnetic field sufficient to expand the expandable magnetoresponsive material which may comprise the test body. As can be seen in FIG. 35(b), and as described herein, when the test body 120B is in an expanded state it may exert a pressure on the eye 160B due to the expansion of the test body. This expansion and associated force may cause a slight deformation in the eye 160B. When the test body 120C is removed from, for example, a magnetic field and it may return to an initial state as the eye 160C rebounds to its original shape, as illustrated in FIG. 35(c). As described herein, the amount of time involved for the test body 120C to transition back to the initial state, as shown in FIG. 35(c), is measured by wirelessly detecting the change or rate of change in the mechanical strain experienced by the contact lens, which may then be used to determine the absolute intraocular pressure of the eye. It should be noted that the degree of expansion of the expandable material comprising the test body 120C as depicted in FIG. 35 may be exaggerated in order to better aid in the understanding of the present disclosure.

Figure 36:
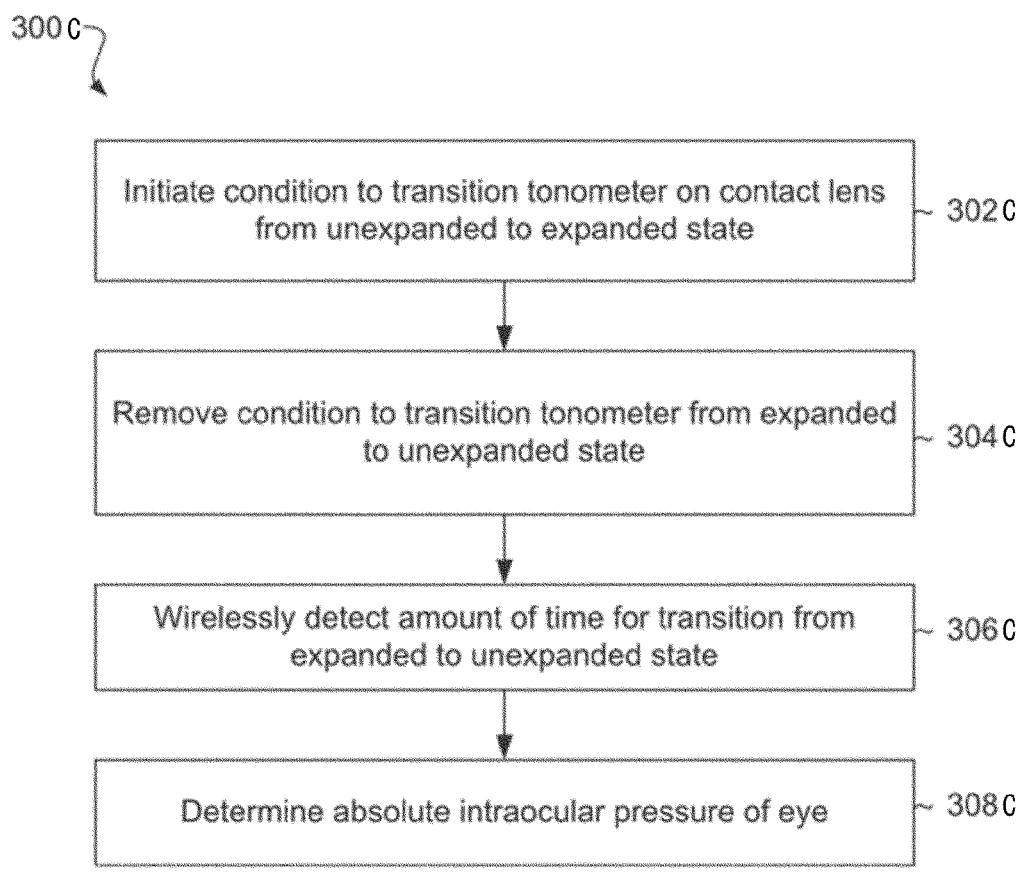
FIG. 36 illustrates a block diagram of an example method for wirelessly determining the absolute intraocular pressure of an eye.

Referring now to FIG. 36, a method 300C of wireles sly determining the absolute intraocular pressure of an eye is illustrated. In this example, the method 300C includes initiating a condition in order to transition a test body on a contact lens, for example a test body of a tonometer system, to an expanded state 302C, stopping the condition so that the test body transitions from the expanded state to the initial state 304C, wirelessly monitoring an amount of time involved for the test body to transition from an expanded state to an initial state 306C, and determining the absolute intraocular pressure of the eye from the amount of time involved for the test body to transition from the expanded state to the initial state 308C.

At block 302C, a contact lens including a test body as described herein, for example with regard to FIG. 34 may be exposed to a condition such that the test body transitions from an initial state to an expanded state, to thereby exert a force on the eye as shown in FIG. 35. For example, where the contact lens includes a tonometer system including a magnetoresponsive test body as described herein, the test body may be exposed to a magnetic field such that the test body transitions from an initial state to an expanded state, for example as shown in FIG. 35 (b). In some cases a secondary device, such as an electromagnetic device capable of generating a magnetic field may be positioned near the contact lens to transition the test body from an initial state to an expanded state. For example, a device included in the contact lens may generate the magnetic field. In some cases, the antenna, when it receives a signal carries an electric current that produces a magnetic field, which causes the expandable material to expand. In another example, the user may be provided with a device that generates the magnetic field. In yet another example, the magnetic field is generated by a hand-held device or another type of device. In some cases, the magnetic field is generated in a doctor's office or another type of location.

At block 304C the condition that initiated the transition of the test body from the initial state to the expanded state is removed. For example, in some cases where the test body was exposed to a magnetic field at block 302C, the magnetic field may be removed at block 304C. In some cases, the contact lens may be removed from the magnetic field, or a device used to generate a magnetic field may be removed from the vicinity of the contact lens. In some cases where the magnetic field is generated by an electromagnetic device, the magnetic field may be turned off. In some embodiments when the condition, such as the magnetic field, is turned off or removed the test body may transition from an expanded state to an initial state as described herein.

At block 306C the amount of time involved for the test body to transition from the expanded state to an initial state, for example as shown in FIG. 35 (c), is wirelessly monitored. The transition time may be wirelessly monitored by, the sensor 130C as described herein with respect to FIG. 34. In some cases the amount of time involved for the test body to transition is measured by wirelessly detecting the change or rate of change in the mechanical strain experienced by the contact lens. In some cases this may be achieved with a variable capacitance sensor, as described herein. For example, in some cases a first mechanical strain may correspond to the expanded state of the magnetoresponsive test body and a second mechanical strain may correspond to the initial state of the magnetoresponsive test body, and the amount of time between detecting the first mechanical strain and detecting the second mechanical strain may be wirelessly recorded, for example by an electronic device in communication with the sensor. However, in some other cases the deceleration of the test body as the expandable material transitions from an initial state to an expanded state at block 302C may be wirelessly measured or detected.

At block 308C the information from block 306C, for example the amount of time involved for the test body to transition from the expanded state to the initial state, or the rate of change of the mechanical strain of the contact lens is used to determine the absolute intraocular pressure of the eye. In some cases, the amount of time for the test body to transition from the expanded state to the initial state may correspond to the absolute intraocular pressure of the eye. Similarly, in some cases the rate of change of the mechanical strain of the test body may correspond to the absolute intraocular pressure of the eye.

Embodiment 5

The principles described herein include incorporating a variable capacitance sensor into a contact lens which can be worn on a user's eye. While the contact lens is worn on the user's eye, the relative intraocular pressure of the eye can be wirelessly measured and monitored by detecting changes in the mechanical strain of the contact lens via the variable capacitance sensor.

In some cases, the variable capacitance sensor may include one or more layers of transparent material and may be disposed on an outer surface of the contact lens. For example, the variable capacitance sensor may include a first conductive layer, a second conductive layer, and a dielectric layer disposed between the first and second conductive layers. One or more of the conductive layers may include a polymer, a metal, a microcomposite material, a nanocomposite material, any appropriate material, or combinations thereof. For example, the conductive layers may be transparent polymer layers and may include, for example, poly (3,4-ethylenedioxythiophene) polystyrene sulfonate. The dielectric layer may be a transparent polymer layer and may include, for example, polydimethylsiloxane. In some examples, one or more of these layers may be deposited on the contact lens by a number of deposition process, for example cast molding, printing, or spin coating. In some cases the layers may be deposited on a mold and may then be stamped onto the contact lens. In some cases, a diffusion or migration barrier is included between one or more layers to avoid material contamination between the layers. For example, a diffusion or migration barrier may be included between a conductive layer and dielectric layer to prevent the diffusion or migration of materials therebetween.

In some embodiments the variable capacitance sensor including first and second conductive layers with a dielectric layer disposed there between may function as a capacitor. For example, the variable capacitance sensor may be a parallel plate capacitor, with the first and second conductive layers serving as parallel plates. In this example the capacitance of the variable capacitance sensor is related to the separation distance between the first and second conductive layers, or, in other words, the thickness of the dielectric layer disposed there between. In some cases, as the contact lens, and variable capacitance sensor disposed thereon, is bent or stretched due to, for example, the expansion or retraction of an eye from changes in intraocular pressure, the dielectric layer may experience a corresponding change in thickness. This change in thickness, for example due to stretching of the dielectric material, may thereby result in a change in the capacitance of the capacitor including the variable capacitance sensor.

The variable capacitance sensor may further include an antenna structure. In some cases the antenna structure may be incorporated into the topmost conductive layer of the capacitor including the variable capacitance sensor. In some cases the antenna structure may be the topmost conductive layer of the capacitor including the variable capacitance sensor. Thus, in some examples, the variable capacitance sensor may be an electrical oscillator formed by the capacitor, the antenna, which has a constant inductance, and the natural resistance of the variable capacitance sensor. In some cases this electrical oscillator may have a natural frequency which is dependent on, or corresponds to the mechanical strain of the variable capacitance sensor. Thus, in some cases where the variable capacitance sensor is disposed on the contact lens, the mechanical strain of the contact lens, or how much the contact has been stretched by the eye, can be measured by detecting the natural frequency of the electrical oscillator including the variable capacitance sensor. In some examples, the contact lens and/or variable capacitance sensor may further include a temperature sensor. In some embodiments, data from the temperature sensor may be used to mathematically compensate for the natural thermal expansion of materials in the contact lens in order to obtain a more accurate reading.

In some examples, the natural frequency of the variable capacitance sensor may be wirelessly detected by an electronic device. For example, an electronic device may send a signal having a signal frequency to the contact lens such that the contact lens sends a response signal when the signal frequency matches the natural frequency of the electrical oscillator including the variable capacitance sensor. In this way, the mechanical strain of the contact lens, and thus relative intraocular pressure of the eye, may be wirelessly measured. Further, the contact lens may not include a battery or integrated circuit, thereby simplifying manufacturing and reducing costs. In some cases, the electronic device may have a wireless remote powering system and may use a far field electromagnetic coupling method to transmit power to the contact lens. In some cases, the electronic device may have a wireless remote powering system and may use an inductive coupling, or near field, method to transmit power to the contact lens. In some examples, communication between the contact lens and electronic device may occur via a half duplex or full duplex scheme. That is, in some examples both power and data may be wirelessly transmitted between the contact lens and an electronic device via a single wireless connection. However, in some examples power may be transmitted by one method or connection and data may be transmitted by a second method or connection.

Figure 37:
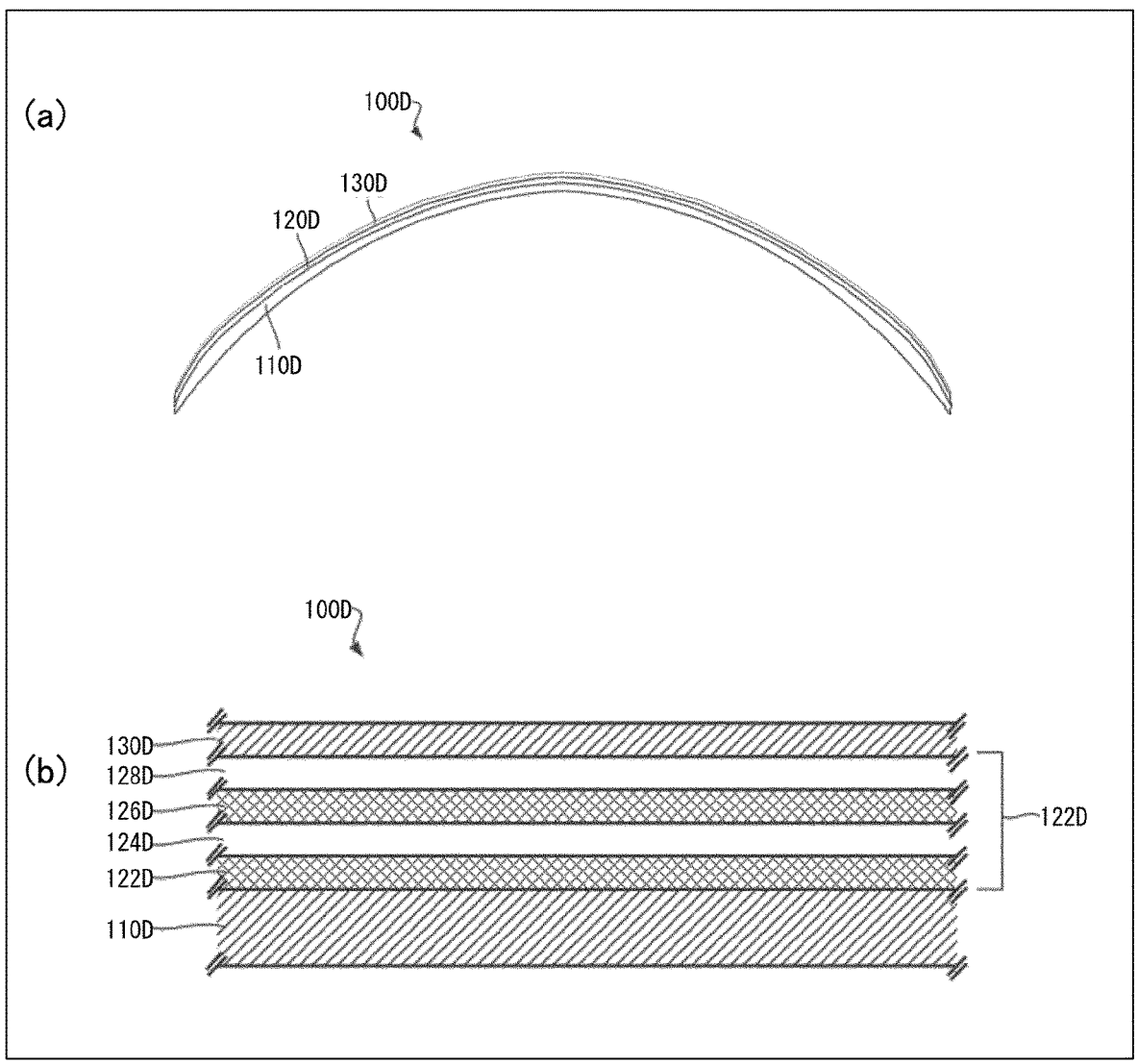
FIG. 37 is a cross sectional view of an example contact lens incorporating a variable capacitance sensor.

FIG. 37 depicts an example of a contact lens 100D including a lens material 110D and a variable capacitance sensor 120D disposed thereon. The lens material 110D may include any material suitable for use as a contact lens as is now know or may be developed in the future. That is, in some examples, the lens material 110D may include a typical hydrogel contact lens as is known in the art. For example, in some embodiments the lens material 110D may include a transparent polymer material, such as a hydrogel. In some cases the lens material 110D may include a silicone hydrogel material. Further, the contact lens 100D may include an encapsulation layer 130D disposed over the variable capacitance sensor 120D.

In some embodiments and as shown in FIG. 37 (b), the variable capacitance sensor 120D may contain at least a layer of conductive material 124D, also referred to as conductive layer 124D, and a layer of dielectric material 126D, also referred to as dielectric layer 126D, overlying the layer of conductive material 124D. In some cases the layer of dielectric material 126D may be disposed directly on the layer of conductive material 124D. In some examples the variable capacitance sensor 120D may include a first conductive layer 124D, a dielectric layer 126D overlying the first conductive layer 124D, and a second conductive layer 128D overlying the dielectric layer 126D. The second conductive layer 128D may be disposed directly on the dielectric layer 126D.

The conductive layer or layers 124D, 128D and the dielectric layer 126D may cover or be disposed over a substantially similar area of the underlying lens material 110D. That is, the conductive layer or layers 124D, 128D and the dielectric layer 126D may have a substantially identical shape and/or border when viewed from above. In some cases the conductive layer or layers 124D, 128D and the dielectric layer 126D may have an approximately circular, elliptical, or ovular shape on the lens material 110D. However, in some other examples, the conductive layer or layers 124D, 128D and the dielectric layer 126D may include any shape and/or boundary as is suitable for use in the variable capacitance sensor 120D as described herein, for example a conductive layer 124D, 128D may have a half-moon shape. In some examples, a single conductive layer, for example conductive layer 124D or 128D may include two half-moon shapes separated from one another. The conductive and/or dielectric layers may be substantially continuous layers. In some cases the conductive and/or dielectric layers may not be substantially continuous and may include one or more separate areas of the same layer.

In some cases, the conductive material including the layer or layers of conductive material 124D, 128D, may be a transparent polymer material. The conductive material may include a polymer mixture of two or more ionomers. In some examples the conductive material may include a polymer or polymer mixture having aromatic cycles and/or double bonds. In some cases the conductive material may include a polymer or polymer mixture including nitrogen and/or sulfur. In some cases the conductive material may include a macromolecular salt. For example, in some embodiments the conductive material may include poly(3,4-ethylenedioxythiophene) polystyrene sulfonate (PEDOT:PSS). In some cases the conductive material may include one or more additives, such as polyethylene glycol (PEG), for example to control or adjust the viscosity of the conductive material during processing.

In some other embodiments the conductive material may include a gel, such a hydrogel mixed with a suitable salt. For example, the conductive material may include a silicone hydrogel mixed with a salt to thereby form an ionic conductor. In some cases the salt may be sodium chloride (NaCl). In some cases where the conductive material include a hydrogel mixed with a salt the layer or layers forming the conductive material may advantageously have substantially the same or similar mechanical properties as the underlying lens material 110D.

In some cases the dielectric material including the dielectric layer 126D may include a transparent polymer material. The dielectric material may be an elastomer. In some cases the dielectric material may include any transparent elastomer having a lower electrical and/or ionic conductivity than the conductive material. For example, in some cases the dielectric material may include polydimethylsiloxane (PDMS).

As used herein, the term 'conductive' refers to the ability of the layer or material to act as an electrical and/or ionic conductor while the term 'dielectric' refers to the ability of the layer or material to act as an electrical or ionic insulator. When used herein in conjunction with one another, the terms 'conductive' or 'conducting' refers to the fact that the 'conductive' material has a higher electrical and/or ionic conductivity than the 'dielectric' material.

In some embodiments the variable capacitance sensor 120D can further include an additional layer of dielectric material 122D disposed below the first conductive layer 124D. Thus, in some embodiments the first conductive layer 124D of the variable capacitance sensor 120D can be disposed directly on the lens material 110D, for example on the outer surface of the lens material 110D, however in some other embodiments the variable capacitance sensor 120D can include a lower dielectric layer 122D that is disposed directly on the lens material 110D. In some cases this lower dielectric layer 122D can function as a substrate layer during manufacturing of the variable capacitance sensor 120D as further described herein.

In some cases where the variable capacitance sensor 120D may include two or more conductive layers 124D, 128D, each conductive layer may include the same conductive material, or each layer may include a different conductive material from any other conductive layer. Similarly, in cases where the variable capacitance sensor 120D may include two or more dielectric layers 122D, 126D, each dielectric layer may include the same dielectric material, or each layer may include a different dielectric material from any other dielectric layer.

In some cases the contact lens 100D may further include an encapsulation layer 130D disposed over the variable capacitance sensor 120D. The encapsulation layer 130D may be in direct contact with the variable capacitance sensor 120D. In some examples the encapsulation layer 130D may include a polymer material, such as a hydrogel. In some cases the lens material 110D may include a silicone hydrogel material and may be the same material as the lens material 110D. The encapsulation layer 130D may have a thickness of from about 0.1 micrometers to about 20 micrometers, from about 0.5 micrometers to about 15 micrometers, or from about 1 micrometers to about 10 micrometers.

The variable capacitance sensor 120D may have a thickness on the lens material 110D of from about 10 micrometers to about 100 micrometers, or from about 20 micrometers to about 50 micrometers. It has been advantageously found that when the variable capacitance sensor 120D has a thickness of less than about 100 micrometers, specifically less than about 50 micrometers, the variable capacitance sensor 120D is able to function well in detecting the relative intraocular pressure of an eye, while the contact lens 100D including the variable capacitance sensor 120D perform in a substantially identical way with respect to user comfort and visions correction to a typical contact lens that does not include a sensor. In some examples the one or more conductive layers which include the variable capacitance sensor 120D may each have a thickness of from about 0.1 micrometers to about 20 micrometers, from about 0.5 micrometers to about 15 micrometers, or from about 1 micrometer to about 10 micrometers. Similarly, the one or more dielectric layers 122D, 126D which may include the variable capacitance sensor 120D, may have a thickness of from about 0.1 micrometers to about 20 micrometers, from about 0.5 micrometers to about 15 micrometers, or from about 1 micrometer to about 10 micrometers.

Figure 38:
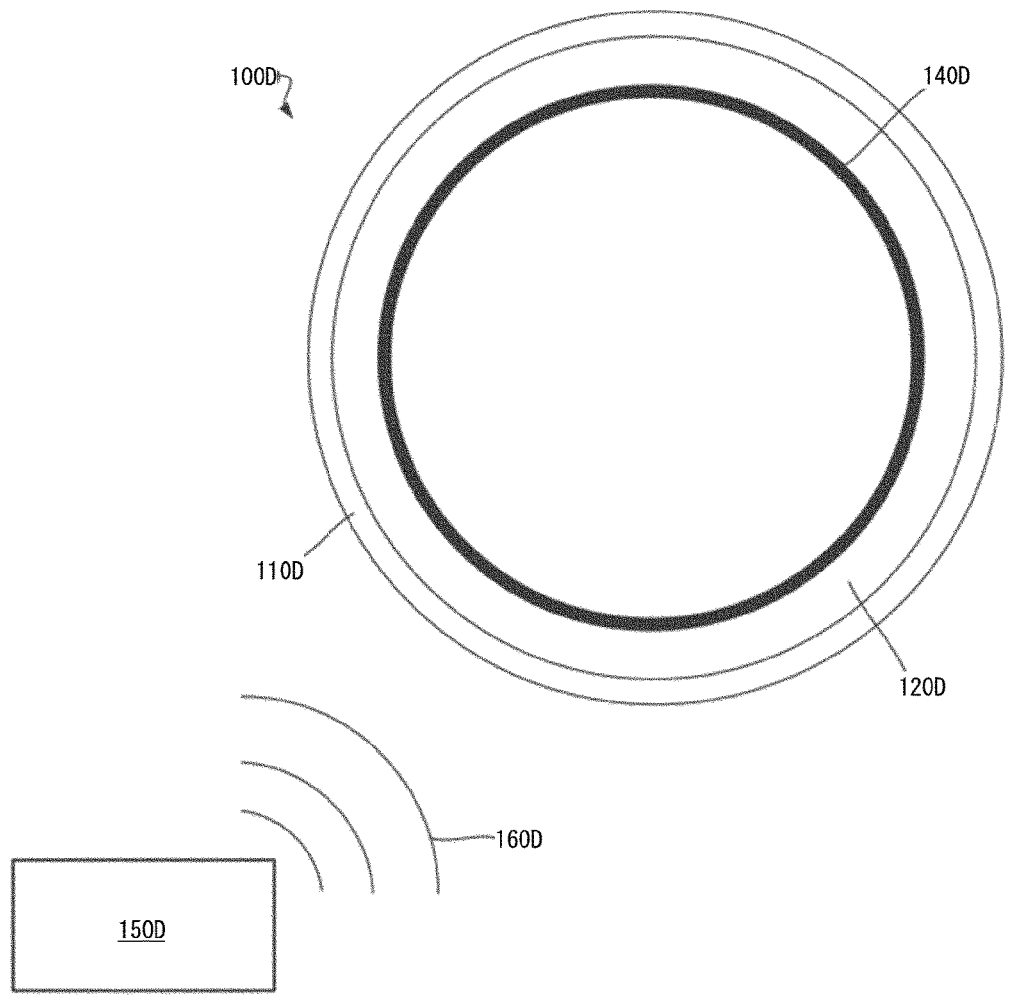
FIG. 38 is a top view of an example contact lens system including a contact lens incorporating a variable capacitance sensor and an antenna, and an electronic device.

As described herein and illustrated in FIG. 38, in some cases the variable capacitance sensor 120D may include an antenna structure 140D. The antenna structure 140D may include a loop or coil structure as is well known in the art, however other antenna designs are expressly contemplated herein. For example, any antenna design capable of functioning as described herein and which may be incorporated into the variable capacitance sensor 120D as described herein may be utilized as will be understood by the skilled artisan. In some cases the antenna structure 140D may include conductive lines which include, for example, the coil or loop structure as shown. The conductive lines may include the conductive material used to form the conductive layers 124D, 128D described herein and may have a line width of from about 25 micrometers to about 200 micrometers, or from about 50 micrometers to about 100 micrometers. Where the variable capacitance sensor 120 includes a capacitor, the antenna structure 140D may be electrically connected to each side of the capacitor to thereby form an electrical circuit. For example, where the variable capacitance sensor 120D includes a parallel plate capacitor including two conductive layers 124D, 128D, the antenna structure may be electrically connected to each of the conductive layers 124D, 128D to thereby form an electrical circuit.

In some cases, the antenna structure 140D may be formed on the upper conductive layer 128D, for example, by printing conductive material in the form of the antenna structure 140D. In some cases the antenna structure 140D may be formed by inkjet printing conductive material on the upper conductive layer 128D. The antenna structure 140D may also be formed by a stencil process wherein conductive material is painted or applied into a stencil including the desired antenna structure 140D which is disposed over the conductive layer 128D. Other methods of forming the antenna structure 140D may be utilized as are known in the art or may be developed in the future. The antenna structure may have a thickness of from about 0.1 micrometers to about 20 micrometers, from about 0.5 micrometers to about 15 micrometers, or from about 1 micrometer to about 10 micrometers. In some cases the antenna structure 140D may thus be incorporated into, or become a part of the upper conductive layer 128D after it has been deposited or formed. However, in some other cases an additional layer including dielectric material (not shown) may be deposited or formed over the upper conductive layer 128D and the antenna structure 140D may be formed on this additional dielectric layer, for example by printing or a stencil process.

As described herein, in some cases the variable capacitance sensor 120D may include a capacitor having two parallel conductive layers 124D, 128D with a dielectric layer 126D disposed there between. In these cases where the conductive layers 124D, 128D act as the plates in a parallel plate capacitor, the capacitance (C) of the capacitor may be given by the equation:

[Math. 1]

$$C = \frac{e_0 e_r A}{d} \quad \text{Equation 1}$$

Where $e_0$ is the permittivity of free space, a constant, $e_r$ is the relative permittivity of the dielectric layer 126D, A is the effective surface area of the plates of the capacitor, that is, conductive layers 124D, 128D, and d is the thickness of the dielectric layer 126D. When the contact lens 100D is subjected to a mechanical strain, for example during relative changes in intraocular pressure while the lens 100D is on the eye, the lens 100D will expand or contract with the eye. This expansion or contraction will cause changes in the area of the conductive layers 124D, 128D (A) and in the thickness of the dielectric layer 126(*d*), and thus will cause corresponding changes in the capacitance (C). For example, an increase in intraocular pressure will cause the eye and lens 100D to expand, thereby causing an increase in the area of the conductive layers 124D, 128D (A) and a decrease in the thickness of the dielectric layer 126(*d*). Similarly, a decrease in intraocular pressure will cause the eye and lens 100D to contract, thereby causing a decrease in the area of the conductive layers 124D, 128D (A) and an increase in the thickness of the dielectric layer 126(*d*). The corresponding changes to the capacitance (C) can ultimately be detected as described herein in order to determine the relative intraocular pressure of the eye.

However, rather than continuously measuring the area of thickness of the layers forming the capacitor, it was found that when a uniaxial force stretches the capacitor with a factor (λ), as occurs during changes in intraocular pressure of the eye, the capacitance (C) scales as:

[Math.2]

$$C = C_0 \lambda^4 \quad \text{Equation 2}$$

Where $C_0$ is the original capacitance of the capacitor in an initial state. For example, the initial state may be an unstretched state, where the lens does not experience tensile forces. In some cases the initial state may be such that some tensile forces are exerted across at least a portion of the lens, for example when the lens is on an eye. By knowing the original capacitance ($C_0$) and measuring the capacitance (C) this scaling factor (λ) can be determined and, for example, transmitted to an external reader device in order to determine the relative intraocular pressure of the eye. This is possible because the scaling factor (λ) is proportional to the mechanical strain on the contact lens 100D which is proportional to the intraocular pressure of the eye. In some cases, the scaling factor (λ) may be linearly related to the mechanical strain on the contact lens 100D, however in other cases the scaling factor (λ) may have a non-linear relationship with the mechanical strain on the contact lens.

Figure 39:
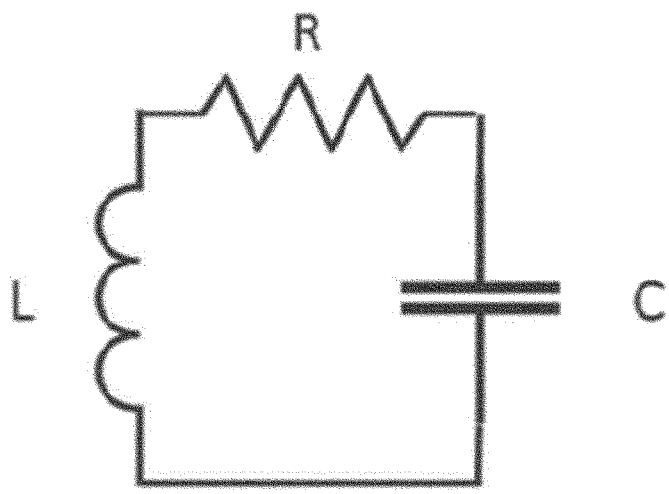
FIG. 39 illustrates an example circuit diagram of a variable capacitance sensor.

In cases where the variable capacitance sensor 120D includes an antenna structure 140D electrically connected to the two conductive layers 124D, 128D including the capacitor an electrical oscillator can be formed. The electrical oscillator is an LCR oscillator which can be conceptualized as an inductor, a capacitor, and a resistor connected in series. Here, the inductance (L) is constant and given by the structure of the antenna 140D, the capacitance (C) is described by Equation 1 and Equation 2, and the resistance (R) is determined by the conductivity of the conductive layers 124D, 128D. FIG. 39 illustrates an example circuit diagram of the LCR oscillator including variable capacitance sensor 120D and antenna structure 140D. The natural frequency (f) of this oscillator is given by the equation:

[Math. 3]
$$f = \frac{1}{2\pi\sqrt{LC}} \qquad \text{Equation 3}$$

However utilizing Equation 2 to describe the capacitance (C) allows for the natural frequency (f) of oscillator to be written as:

[Math. 4]
$$f = \frac{1}{2\pi\lambda^2\sqrt{LC_0}} \qquad \text{Equation 4}$$

Accordingly, the scaling factor (λ), and thus relative intraocular pressure of the eye, can be determined by measuring or detecting the natural frequency (f) of the electrical oscillator formed from the capacitor including the variable capacitance sensor 120D and antenna structure 140D.

Referring again to FIG. 38, it is well known that the natural frequency of such an electrical oscillator can be easily measured from a separate electronic device 150D, such as a vector network analyzer (VNA). The electronic device 150D can send a wireless signal 160D to the contact lens 100D, which upon receipt of the wireless signal 160D by the antenna structure 140D can send a response signal to the electronic device 150D, as described further herein. The signal received by the electronic device 150D may contain information such as the natural frequency (f) of the electrical oscillator in the contact lens 100D which can then be used to determine the relative intraocular pressure of the eye. Utilizing a separate electronic reader device 150D to determine the natural frequency (f) of the electrical oscillator advantageously allows for a wireless measurement of the relative intraocular pressure of the eye via the contact lens 100D without the need for a power source, such as a battery, or an integrated circuit such as an ASIC on the lens 100D. Thus, in some cases the lens 100D does not include a power source or an integrated circuit.

Figure 40:
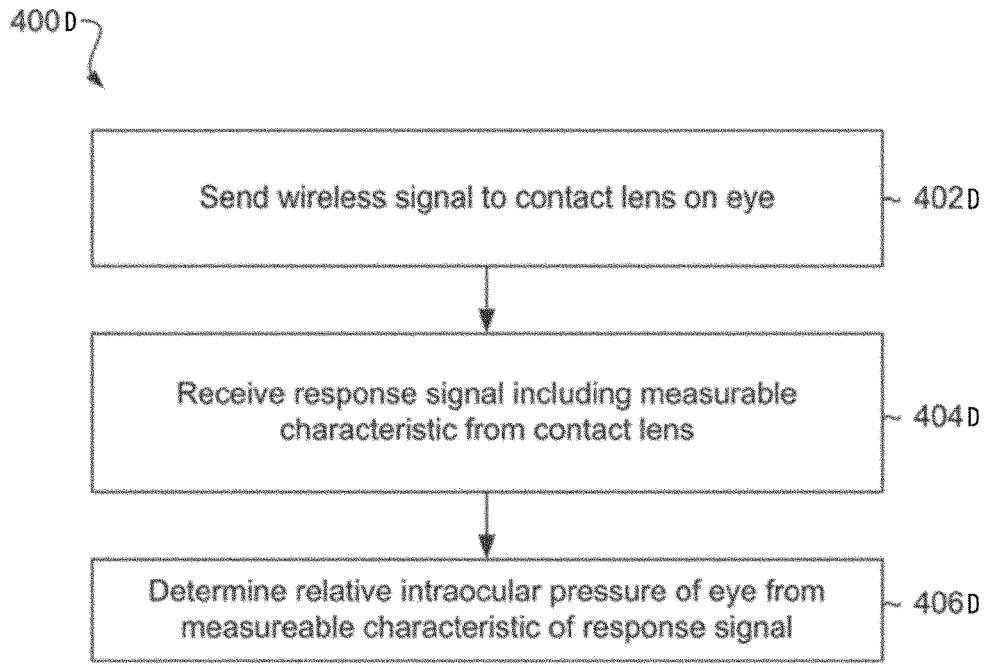
FIG. 40 is a block diagram of an example system for wirelessly determining the relative intraocular pressure of an eye.

FIG. 40 illustrates an example of a method 400D of wirelessly determining the relative intraocular pressure of an eye. In this example, the method 400D includes sending a wireless signal to the contact lens 402D, receiving a response signal from the contact lens 404D, and determining the relative intraocular pressure of the eye 406D.

At block 402D a wireless signal is sent from an electronic device, such as a vector network analyzer, to the contact lens on the eye. The contact lens and electronic device may be contact lens 100D and electronic device 150D as described herein with respect to FIGS. 37 and 38, and may include a variable capacitance sensor including an electrical oscillator as described herein. The wireless signal has a signal frequency. In some cases the electronic device may vary the signal frequency over a predetermined range, thus sending a plurality of wireless signals to the contact lens, each having a different signal frequency.

At block 404D, the electronic device receives a response signal from the contact lens. The response signal is sent or transmitted from the contact lens to the electronic device when the signal frequency of the wireless signal sent in block 402D matches or corresponds to the natural frequency of the electrical oscillator. Further, the response signal sent from the contact lens includes a measurable characteristic, such as the frequency of the response signal itself, corresponding to the natural frequency of the electrical oscillator. Thus, at block 404D the electronic device receives a response signal from the contact lens including information corresponding to the natural frequency of the electrical oscillator.

At block 406D the natural frequency of the electrical oscillator is used to determine the relative intraocular pressure of the eye by utilizing, for example, Equation 4 as described herein.

Embodiment 6

Figure 41:
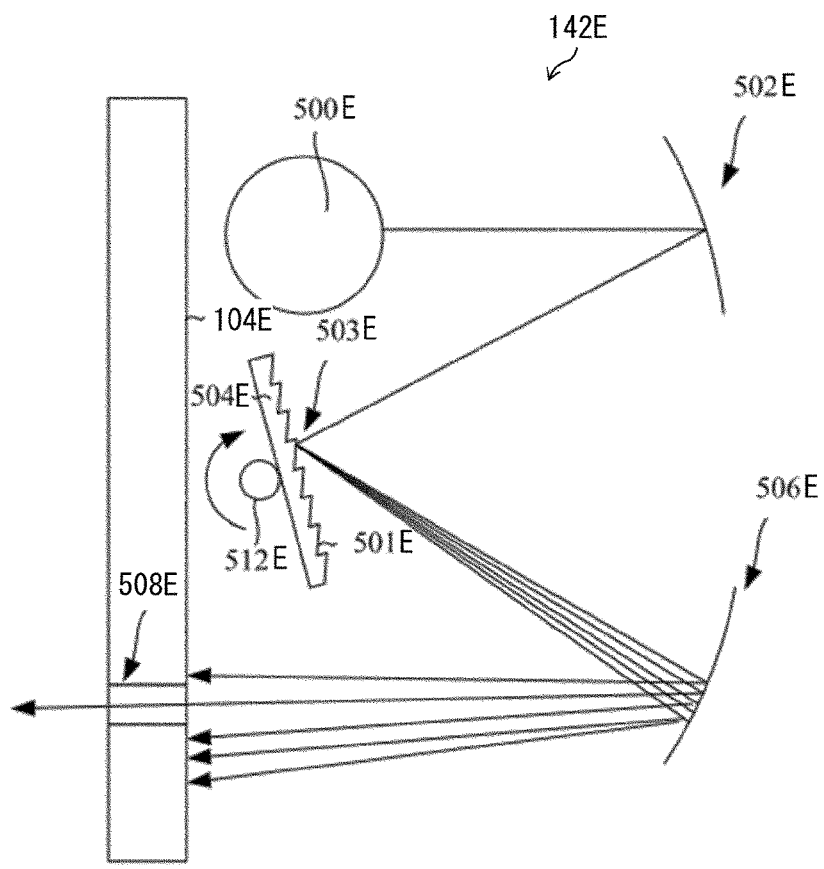
FIG. 41 illustrates a cross-sectional view of an example of a light transmitter.

A storage container 140E of this embodiment comprising an internal cavity 102E as the storage container 140 depicted in FIGS. 3 and 4. A light transmitter 142E (corresponding to the light source 142 depicted in FIG. 4) may be incorporated into a side wall of the cavity 102E. FIG. 41 depicts an example of a light transmitter 142E. In this example, the light transmitter 142E includes a light source 500E, a first mirror 502E, a diffraction grating 504E, a second mirror 506E, and a slit 508E in the wall 104E of the storage container 140E. In some cases, an optical window may be placed within the slit 508E. In some examples, these components of the light transmitter 142E are located within the body portion of the storage container 140E, the lid portion of the storage container 140E, an attachment to the storage container 140E, or combinations thereof.

The light source 500E may be any appropriate type of light source. In some examples, the light source is an incandescent light source, a fluorescent light source, a halogen light source, a light emitting diode light source, another type of light source, or combinations thereof. The light source may be encompassed within a blub, diode, or other source that can be turned on and off with a switch. In some cases, the light source can emit at least two different types of wavelengths. In some situations, the light source is an infrared light source, a visible light source, an ultraviolet light source, another type of light source, or combinations thereof.

The first mirror 502E may be used to direct light from the light source 500E to the diffraction grating 504E. In some examples, the first mirror 502E is curved so that different wavelengths of light come into contact with the mirror at slightly different positions. With the wavelengths coming off the mirror at different positions, the wavelengths also come off the first mirror 502E at slightly different angles, which assists in causing the wavelengths to separate.

The diffraction grating 504E may be an optical component that splits light into several beams of different wavelengths in different directions. The directions of these beams depend on the spacing of the grating and the wavelength of the light. The diffraction grating 504E may be a reflective grating or a transmissive grating. In the example of FIG. 41, the diffraction grating 504E is a reflective grating that reflects the wavelengths in a way that causes the wavelengths to disperse. In this example, the diffraction grating 504E has a plurality of ridges 501E on its reflective surface 503E.

The angle of each wavelength hits the reflective surface at a different location, and the angle of the diffraction grating separates the beams of different wavelengths farther apart. In other words, the diffraction grating 504E is a dispersive element that causes the wavelengths to spread out even more. In other examples with transmissive gratings, the diffraction grating 504E can be a prism that separates light into different wavelengths as the light passes through the thickness of the prism's material.

Figure 42:
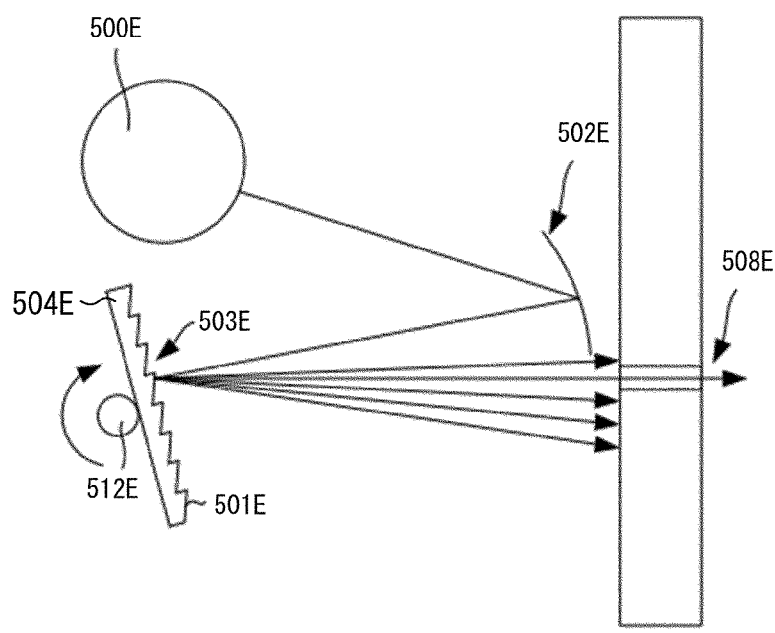
FIG. 42 illustrates a cross-sectional view of an example of a light transmitter.

In some examples, the diffraction grating 504E is connected to a tilt mechanism 512E. In those examples, where the diffraction grating 504E is connected to a tilt mechanism, the tilt mechanism 512E can cause the diffraction grating 504E to move to a different angle. This can cause the angle that the beams of different wavelengths come off of the diffraction grating 504E to change. In some cases, a second mirror 506E reflects the light beams off of the diffraction grating 504E towards the slit 508E. In the example of FIG. 42, the diffraction grating 504E directs the light directly to the slit 508E without being directed through the second mirror 506E.

The spacing of the light beams approaching the slit may be such that just a single beam of light can pass through the optical window at a time. Thus, just a single light beam is transmitted into a solution disposed within the cavity 102E at a time. To cause another light beam of a different wavelength to be transmitted through the optical window, the tilt mechanism 512E can cause the diffraction grating 504E to move so that a different beam of a different wavelength is transmitted through the slit 508E.

While these examples have depicted light transmitters with specific components in specific arrangements, the light transmitters may include more or less components than those depicted and in different arrangements. Any appropriate type of light transmitter may be used in accordance with the principles described in the present disclosure.

Figure 43:
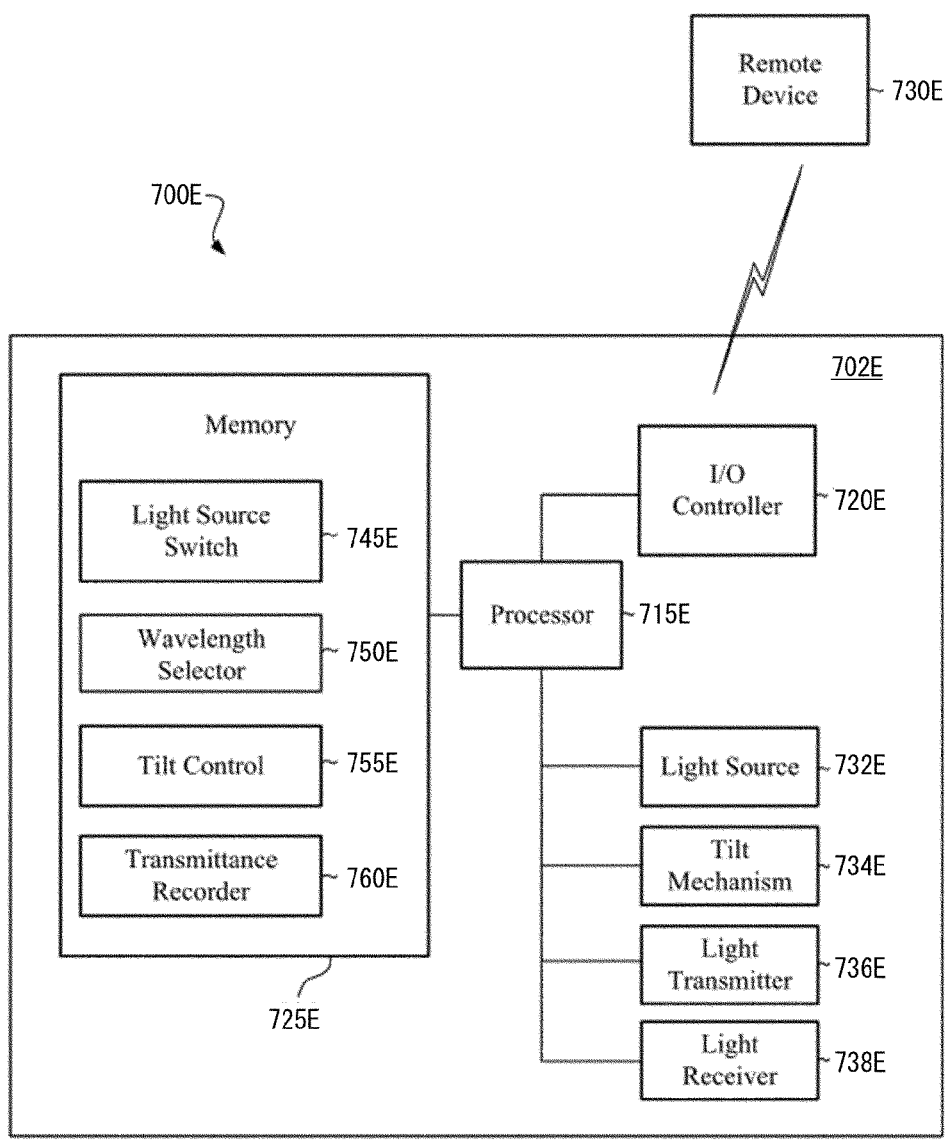
FIG. 43 illustrates a block diagram of an example of a health condition system.

FIG. 43 depicts a diagram of a health condition system 700E incorporated into a contact lens container 702E. The system 700E includes a processor 715E, an I/O controller 720E, and memory 725E. The I/O controller 720E may be in communication with a remote device 730E. The components of the system and the remote device 730E may communicate wirelessly, through hard wired connections, or combinations thereof. In some examples, the contact lens container 702E may include a transponder to communicate with the remote device 730E. Further, in some cases, the remote device 730E may include a base station in communication with the transponder. In some cases, the remote device 730E may be a data center. The memory 725E of the system may include a light source switch 745E, wavelength selector 750E, a tilt control 755E, and a transmittance recorder 760E. The processor 715E may also be in communication with a light source 732E, a tilt mechanism 734E, a light transmitter 736E, and a light receiver 738E.

The processor 715E may include an intelligent hardware device, (e.g., a general-purpose processor, a digital signal processor (DSP), a central processing unit (CPU), a microcontroller, an application-specific integrated circuit (ASIC), a field-programmable gate array (FPGA), a programmable logic device, a discrete gate or transistor logic component, a discrete hardware component, or any combination thereof). In some cases, the processor 715E may be configured to operate a memory array using a memory controller. In other cases, a memory controller may be integrated into the processor 715E. The processor 715E may be configured to execute computer-readable instructions stored in a memory to perform various functions (e.g., functions or tasks supporting the evaluation of prescribed optical devices).

The I/O controller 720E may represent or interact with a modem, a keyboard, a mouse, a touchscreen, or a similar device. In some cases, the I/O controller 720E may be implemented as part of the processor. In some cases, a user may interact with the system via the I/O controller 720E or via hardware components controlled by the I/O controller 720E. The I/O controller 720E may be in communication with any appropriate input and any appropriate output.

The memory 725E may include random access memory (RAM) and read only memory (ROM). The memory 725E may store computer-readable, computer-executable software including instructions that, when executed, cause the processor to perform various functions described herein. In some cases, the memory 725E may contain, among other things, a basic input/output system (BIOS) which may control basic hardware and/or software operation such as the interaction with peripheral components or devices.

The light source switch 745E represents programmed instructions that cause the processor 715E to switch the light source on or off. In some cases, the light source switch may block or unblock a light source that is continuously emitting light. The light source may automatically illuminate when a light portion is combined with the body portion of the contact lens container 702E. In other examples, the light source switch causes the light source to illuminate when instructed to do so. The instructions to illuminate may come from the user interface, a remote device, another type of device, or combinations thereof.

The wavelength selector 750E represents programmed instructions that cause the processor 715E to select a desired wavelength of light to be transmitted through the contact lens solution. In some cases, in response to the contact lens container being instructed to analyze the contact lens solution, the wavelength selector is programmed to automatically cause the processor to start from one end of the light spectrum to the other end. In this example, the wavelength selector may sequentially test each wavelength in a consistent manner. In other examples, the wavelength selector causes only certain types of wavelengths to be tested. In situations where the contact lens solution is being tested for only a particular type of characteristic or certain types of biomarkers, at least some of the wavelengths may be omitted from the analysis. In some cases, a certain wavelength may alter or adversely affect a particular biomarker making the biomarker difficult to identify later in the analysis. In these situations, certain wavelengths may be omitted from the analysis.

The tilt control 755E represents programmed instructions that cause the processor 715E to control the tilt mechanism that is connected to the diffraction grating. The angle at which the diffraction grating is positioned can determine which of the wavelengths is transmitted into the solution. In some cases, the wavelength selector communicates with the tilt control to cause the appropriate wavelength to be transmitted into the solution.

The transmittance recorder 760E represents programmed instructions that cause the processor 715E to record the transmittance of the beam transmitted into the solution. In some cases, multiple beams of different transmittances are separately transmitted into the solution, and the transmittance recorder may record a transmittance for each of the wavelengths. In some cases, the transmittance recorder is in communication with the receiver that receives the light beams. In some situations, the recorder collects the transmittance strength with time stamps and the wavelengths transmitted through the solution are also timestamped. In these situations, the wavelengths transmitted can be compared to the recorded transmittance strengths based on matching times.

Correlations between certain biomarkers and their respective concentrations may go unobserved on one-on-one analysis with each of the patients. However, with such a large sample size, correlations that have been previously unobserved may be detected, for example via data mining techniques used by the system. For example, an analysis may be run on all the biomarker characteristics of users with a specific health conditions. Such an analysis may reveal that a certain biomarkers that had not previously been linked to that health condition has a statistically significant normal concentration level, a statistically significant low concentration level, a statistically significant high concentration level, another statistically significant concentration level, a statistically insignificant type of concentration level, or combinations thereof that had not previously been observed. These correlations may help identify health conditions that may go otherwise unobserved in a patient. Even in those events where the user's health condition may be eventually diagnosed properly, comparing the obtained biomarker characteristics with the information stored in a database (for example the database 600 depicted in FIG. 6) may result in a quicker diagnosis.

Figure 44:
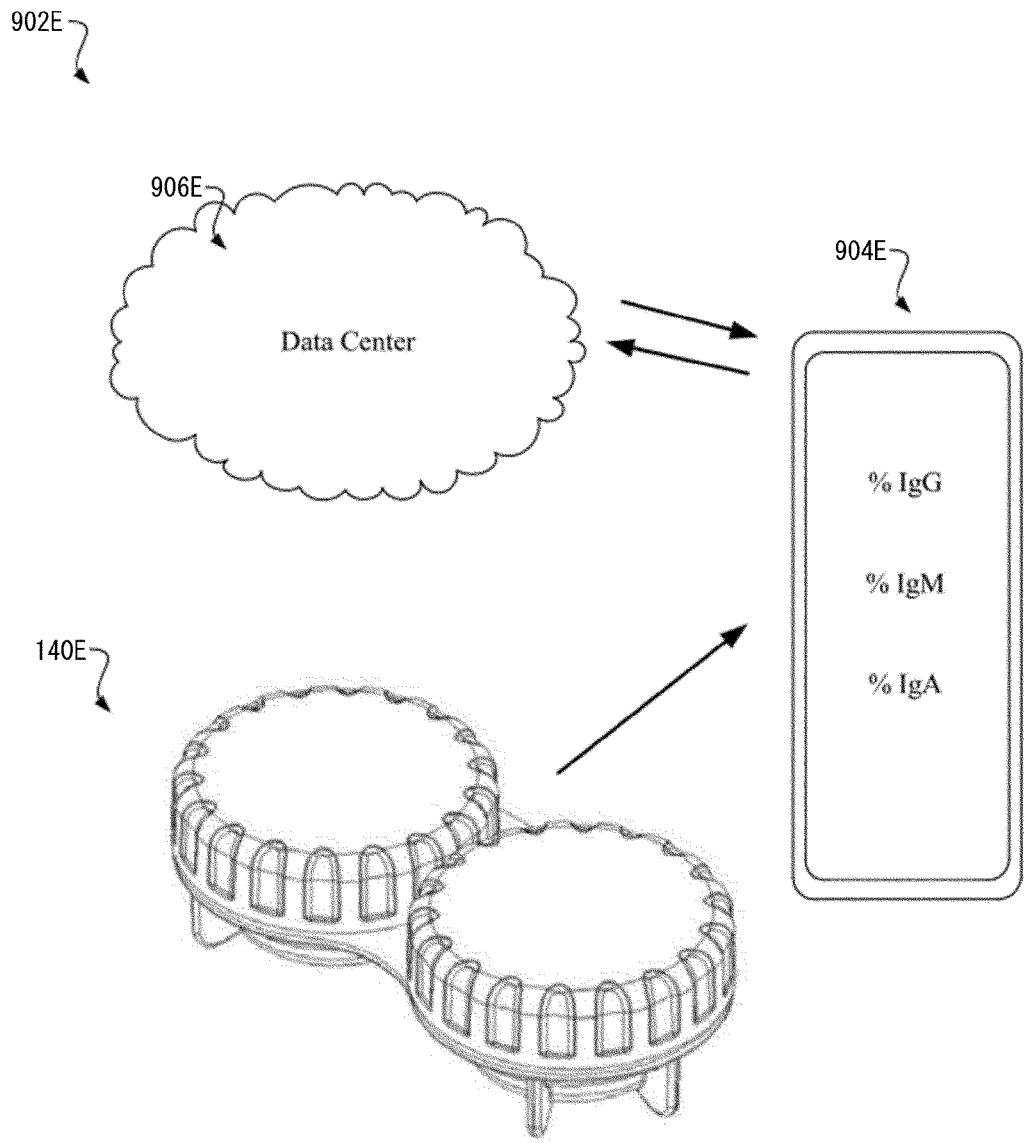
FIG. 44 illustrates a view of an example of a health condition system.

FIG. 44 depicts an example of a system 902E of determining the health condition of a user. In this example, a storage solution may be contained within a contact lens container 140E. The contact lens container 140E may be in wireless communication with a mobile device 904E. The mobile device 904E may relay the recorded levels to the database in the data center 906E, which may send the correlations back to the mobile device 904E. The mobile device 904E may present the results from the hand-held device and/or the correlations from the database in a user-interface of the mobile device.

At least some of the processing of the measurements obtained from the return signals from the storage solution may occur at the contact lens container 140E, the mobile device 904E, and/or the data center 906E. In some examples, the mobile device 904E includes a program that retrieves the correlations from the database and performs additional tasks. For example, the mobile device 904E may retrieve information about the health condition from another source other than the database in response to receiving the health condition from the database. Another additional task that the mobile device 904E may perform in response to receiving the health condition is to retrieve a health professional's contact information, consult a user's calendar to set up an appointment with the health professional, schedule an appointment with the health professional, perform another task, or combinations thereof.

Figure 45:
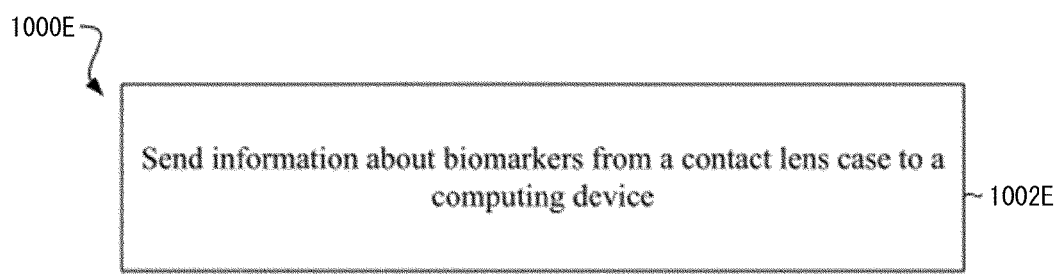
FIG. 45 illustrates a block diagram of a method of determining a health condition.

FIG. 45 illustrates an example of a method 1000E of determining a health condition. In this example, the method 1000E includes sending 1002E information about biomarkers from a contact lens container to a computing device.

At block 1002E, information about the biomarkers is sent from the contact lens container to a computing device. The information may be sent to any appropriate computing device. In some examples, the computing device is a laptop, a desktop, a mobile device, a smart phone, an electronic tablet, a digital device, a remote device, a networked device, another type of device, or combinations thereof.

In some cases, the biomarkers remain on the contact lens when the biomarkers are being analyzed. In other examples, the biomarkers are removed from the contact lens before the analysis. The characteristic may include a type of biomarker, a concentration of biomarker, a location of the biomarker on the contact lens, another type of characteristic, or combinations thereof. The characteristic may involve a single biomarker. In other examples, the characteristic includes the collective condition of multiple biomarkers.

Figure 46:
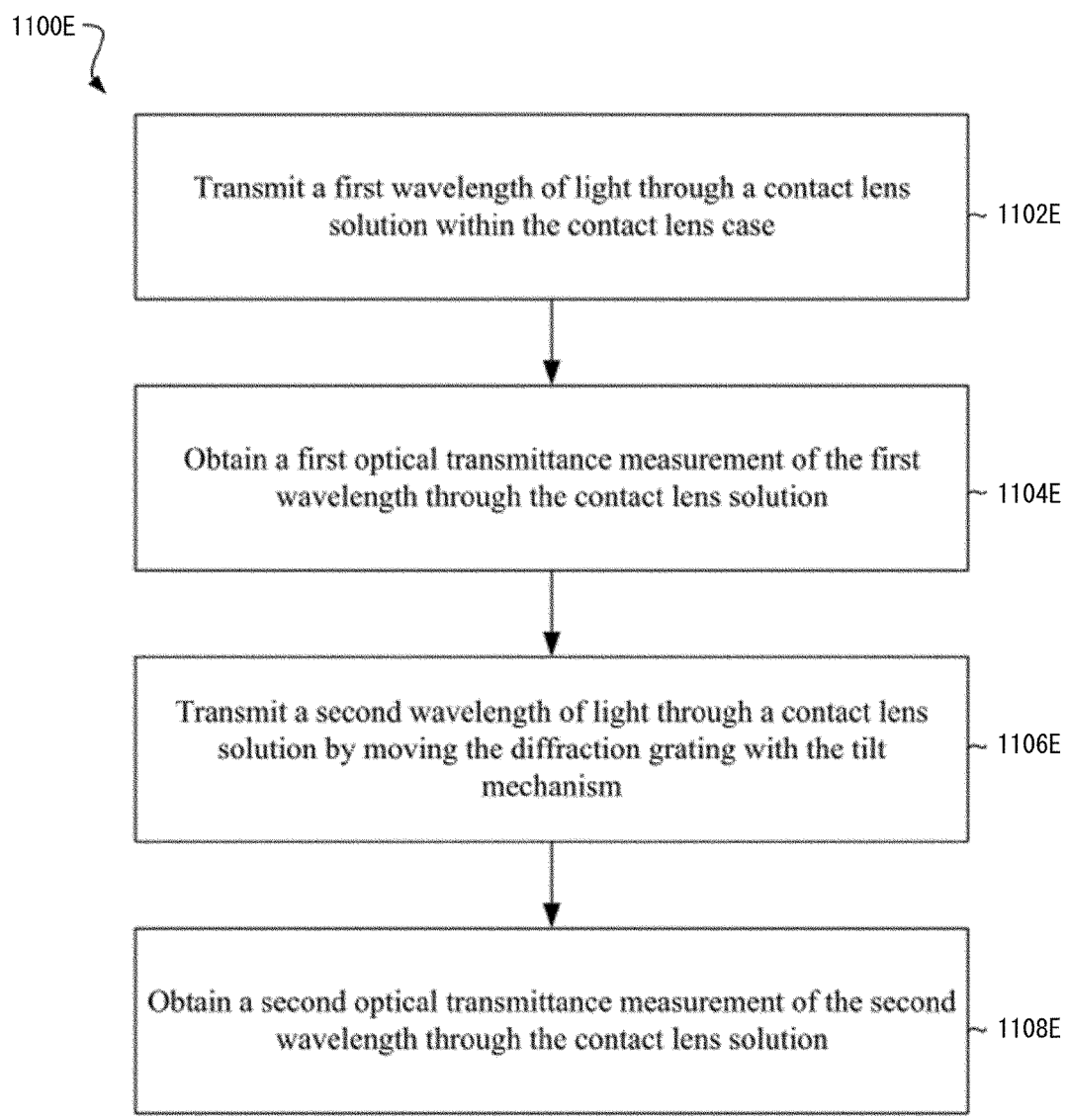
FIG. 46 illustrates a block diagram of a method of determining a health condition.

FIG. 46 illustrates an example of a method 1100E of obtaining a biomarker characteristic. In this example, the method 1100E includes transmitting 1102E a first wavelength of light through a contact lens solution within the contact lens container, obtaining 1104E a first optical transmittance measurement of the first wavelength through the contact lens solution, transmitting 1106E a second wavelength of light through a contact lens solution by moving the diffraction grating with the tilt mechanism, and obtaining 1108E a second optical transmittance measurement of the second wavelength through the contact lens solution.

In some cases, the contact lens solution includes hyaluronan, sulfobetaine, poloxamine, boric acid, sodium borate, ascorbic acid, edetate disodium, sodium chloride, hydroxyalkyl phosphate, poloxamer, sodium phosphate buffer, polyoxyethylene polyoxypropylene block copolymer with ethylene diamine, and polyaminopropyl biguanide, or combinations thereof. The contact lens may include a disinfectant, a surfactant, an anti-fungal agent, an anti-bacterial agent, another type of agent, or combinations thereof.

The removal of the biomarkers from the contact lens into the solution may occur over any appropriate time period. In some examples, the biomarkers are in the solution for at least one minute, at least five minutes, at least 20 minutes, at least 45 minutes, at least an hour, at least two hours, at least 5 hours, at least 7 hours, at least one day, at least two days, another appropriate time period, or combinations thereof.

In some examples, the contact lens is free of surface cavities that are constructed to be binding sites for biomarkers or to draw in tear fluid into the contact lens. In some examples, the contact lens is free of surface treatments that target the binding of specific biomarkers to the contact lens.

In some situations, the storage solution includes binding agents that are configured to facilitate the bonding between a surface of the contact lens and a biomarker from the tear fluid. In other cases, no binding agents are introduced to the contact lens solution. The contact lens may include a surface where the biomarkers are as likely to bind to any surface of the contact lens as any other surface of the contact lens. In some cases, the biomarkers may attach to the optical zone of the contact lens, a peripheral zone of the contact lens, an edge of the contact lens, a posterior side of the contact lens, an anterior side of the contact lens, another area of the contact lens, or combinations thereof.

The contact lens may be made through any appropriate manufacturing method. In some cases, the contact lenses are molded into their shape. In other examples, the contact lenses are machined to their precise shape. In yet other examples, the contact lens are cast molded or spin cast. Spin cast contact lenses can make a continuous surface on the posterior side of the contact lens that matches a profile constructed to assist the user with his or her vision. The front side of the contact lens during a spin casting procedure may include a profile that matches a contact lens mold. The contact lens mold may include a continuous, curved surface without interruptions. In some examples, the spin cast contacts lens provide for a continuous surface that is substantially free of interruptions, such as micro-cavities. In some cases, having a continuous, interruption free surface on both the anterior side and the posterior side may prevent the collection of tear fluid in the contact lens. Avoiding the collection of tear fluid may prevent the contact lens from having an additional amount of weight. Further, when the contact lens is introduced into the solution, a substantial amount of tear fluid may not mix with the contact lens solution, which may skew the volume of fluid in being analyzed and affect the concentration analyses. In some examples where tear fluid is not collected, just the biomarkers may be carried with the contact lens into the solution. Thus, the analysis does not have to be adjusted to accommodate an increase in fluid. However, in some examples, the amount of fluid being analyzed may not require a precise amount of fluid. In one example, the contact lens container may include a fill line and the measurements performed by the sensor may be adequate enough if the solution is close to being at the fill line, but not required to be precisely at the fill line. Further, by not modifying the contact lens to have an enhanced ability to collect specific biomarkers, the concentrations of the biomarkers that bind to the contact lens may be more reflective of the actual concentration of that biomarker in the tear fluid. An enhanced ability to collect a particular biomarker or a wide variety of biomarkers may cause a disproportionate amount of that biomarker to bind to the contact lens, which may skew the measurement levels made when analyzing the solution and potentially lead to an inaccurate characterization of the biomarker's actual concentration.

FIGS. 47-52 illustrate various contact lens containers, according to the present exemplary teachings. Each of the contact lens containers may include the elements disclosed in connection with FIG. 43, including a processor, memory, and I/O controller, and the like.

FIG. 47 depicts an example of a contact lens container 140E. In this example, the container 140E includes a body portion 1200E and a lid portion 1202E. The lid portion 1202E may interlock with the body portion 1200E. In the illustrated example, the lid portion 1202E may threadedly interlock with the body portion 1200E.

The body portion 1200E may have a substantially flat undersurface 1250E that provides stability to the container 140E when resting on a support surface, such as a counter top or sink surface. In other examples, the body portion 1200E includes a plurality of legs that stabilize the body portion 1200E in an upright orientation. In the upright position, the contact lens container 140E is oriented so that the storage solution pools in the bottom of the cavity and away from the threaded portions or other connection mechanisms that secure the lid portion 1202E to the body portion 1200E. The body portion 1200E may also include an inner wall (FIG. 48, 1252E) that is connected to a floor (FIG. 48, 1254E). The inner wall 1252E and the floor 1254E collectively define the cavity. The cavity may be configured to receive a volume of contact lens storage solution. A contact lens may be inserted into the cavity into the storage solution for a desired period of time, such as overnight, until the user decides to reinsert the contact lens back into the user's eye.

The body portion 1200E may include a first cavity 1204E and a second cavity 1206E. Since a user generally wears a separate contact lens in each of his eyes, the contact lens container 140E may include the first cavity 1204E for the first contact lens and the second cavity 1206E for the second contact lens. A sensor may be incorporated into each of the cavities or just one of the cavities. In some cases, the biomarker profile of one of the user's eyes may be similar or the same to the biomarker profile of the other eye. In these examples, testing the biomarkers of one eye may be sufficient to understand the user's tear's chemistry. However, in other examples, testing each of the eye's tear fluid may help identify profiles that may not be realized when testing just a single eye.

Any appropriate type of storage solution may be used in connection with the principles disclosed herein. In some examples, the storage solution includes a disinfectant that kills bacteria, viruses, fungus, germs, enzymes, undesirable organisms, or combinations thereof that are on the contact lens. In some examples, the storage solution also prevents a protein build-up, a lipid build-up, a debris build-up, or other type of build-up on the contact lens. Further, the storage solution may include ingredients that improve wettability and comfort of silicone hydrogel contact lenses or other types of contact lens. In some cases, the storage solution includes a saline solution, a hydrogen peroxide solution, another type of solution, or combinations thereof.

The contact lens container 140E may be formed through any appropriate mechanism. In some cases, the contact lens container 140 is injection molded using synthetic resins, such as polypropylene (PP), polyethylene (PE), polystyrene (PS), polycarbonate (PC), polyethylene terephthalate (PET), acrylonitrile butadiene styrene copolymer (ABS), propylene ethylenic copolymer, or combinations thereof. In other examples, the contact lens container 140E may be casted, machined, or otherwise formed. In some cases, the lid portion 1202E is made of the same materials as the body portion 1200E.

In some cases, the body portion 1200E includes a first thread portion (FIG. 48, 1256E), and the lid portion 1202E includes a second thread portion (FIG. 48, 1258E). In some cases, the first thread portion 1256E is an outer thread portion, and the second thread portion 1258E is an inner thread portion. However, in other examples, the first thread portion 1256E is an inner thread portion, and the second thread portion 1258E is an outer thread portion. The first thread portion 1256E and the second thread portion 1258E can be threadedly connected to one another. With the lid portion 1202E secured to the body portion 1200E through the threaded portions, the lid portion 1202E closes off the cavity.

While these examples have been described with reference to the contact lens container 140E having the lid portion 1202E and the body portion 1200E connected through complementary threaded portions, the lid portion 1202E and the body portion 1200E can be connected through any appropriate mechanism. For example, the lid portion 1202E and the body portion 1200E can be secured together through a snap connection, a compression fit connection, a hinged connection, another type of connection, or combinations thereof. In some examples, the connection is water tight to prevent the storage solution from leaking out of the cavity when the contact lens container 140E is oriented on its side or is oriented upside-down.

Figure 49:
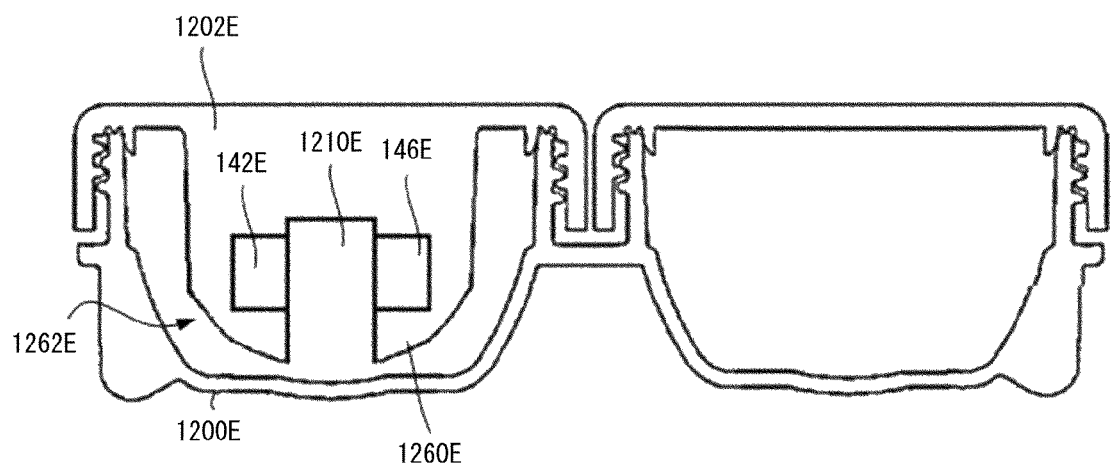
FIG. 49 illustrates an example of a contact lens storage container.

FIGS. 48 and 49 depict examples of a sensor incorporated into a lid portion 1202E. In these examples, the lid portion 1202E includes a protrusion 1208E that protrudes into a volume of the first cavity 1204E. The protrusion 1208E may have a cross-sectional thickness that is less than the cross-sectional thickness of the cavity thereby allowing fluid to move within the space between the surface of the cavity's walls and the surface of the protrusions 1208E. The protrusions may also be sized to pin contact lens to the bottom of the cavity or at least cause the contact lens to be located between the bottom of the cavity and a distal end of the protrusion 1208E.

A protrusion 1208E may be connected to the lid portion 1202E. The protrusion 1208E may extend farther away from the lid portion 1202E than the second threaded portion. The protrusion 1208E may include a distal end 1260E, and the distal end 1260E may include a curved surface 1262E.

In some cases, a center portion of the contact lens comes into contact with a central portion of the floor 1254E of the cavity. In those examples where a gap between the floor 1254E and the distal end 1260E of the protrusion 1208E are smaller than the sagittal depth of the contact lens, the protrusion 1208E and the floor 1254E may collective impose a compressive load on the contact lens that assists in keeping the contact lens up against the curved surface 1262E. However, due to the curvature of the distal end 1260E, the gap may progressively increase from the central portion of the floor 1254E towards the edge of the curved surface 1262E. In such circumstances, the contact lens may otherwise be prone to dislodging from the curved surface 1262E if the contact lens were positioned off center on the curved surface 1262E.

The protrusion 1208E may cause the contact lens to be located in a space within the cavity's volume that is away from a light beam that may be transmitted by the sensor. In other words, the protrusion 1208E may assist in locating the contact lens in a region of the cavity, so that the contact lens is less likely to interfere with the measurements taken in the contact lens solution.

A channel 1210E may be defined in the protrusion 1208E that is sized to allow a portion of the contact lens solution to enter within a volume defined by the channel 1210E. The light transmitter 142E and the light receiver 146E may be located proximate to the channel 1210E so that they may test the contact lens solution that is located in the channel 1210E. In the example of FIG. 48, the channel 1210E is defined in the side wall of the protrusion 1208E, and in FIG. 49, the channel 1210E is formed in the distal end 1260E of the protrusion 1208E. In the example of FIG. 49, to avoid trapping air within the channel 1210E as the protrusion 1208E comes into the contact lens solution, a vent hole (not shown) may connect the channel to the surface of the protrusion's wall.

Figure 50:
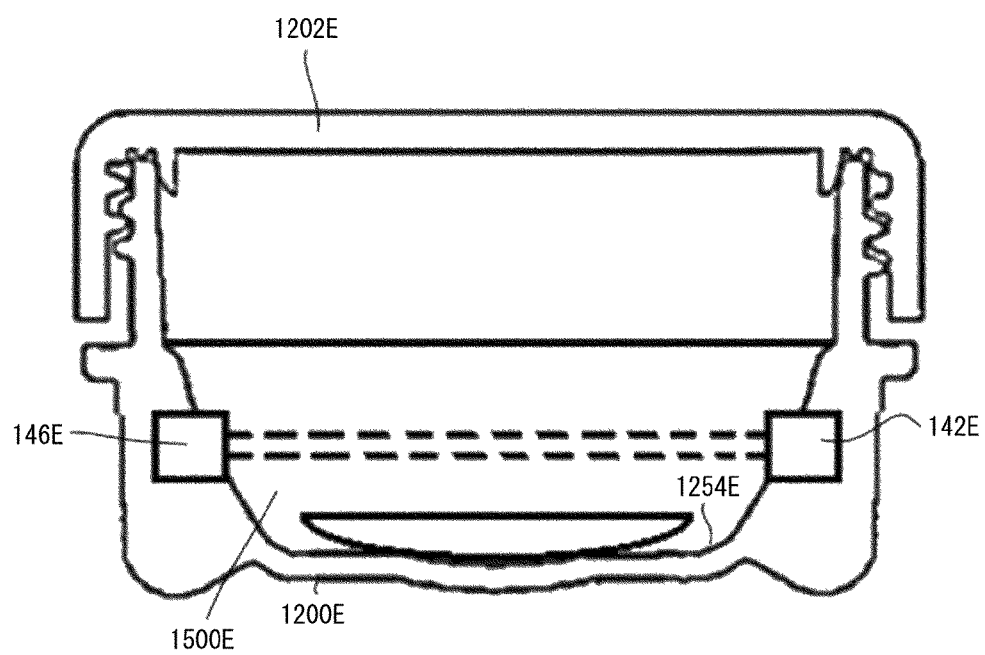
FIG. 50 illustrates an example of a contact lens storage container.

FIG. 50 depicts an example of a cavity 1500E within the body portion 1200E that has a light receiver and a light transmitter 142E located at a distance from the floor 1254E of the cavity that is far enough away so that when the contact lens settles at the bottom of the cavity, the contact lens is located below a space where the light beam is transmitted.

Figure 51:
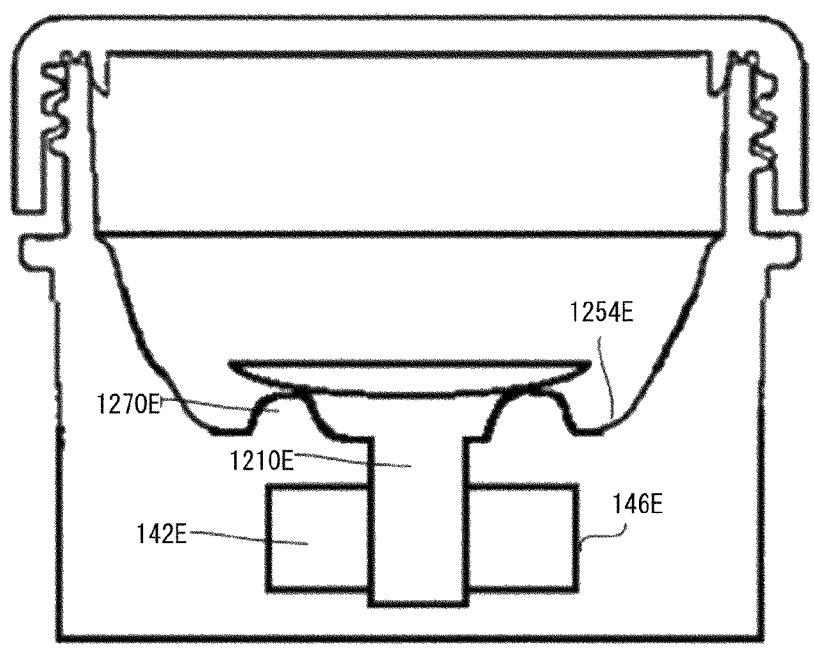
FIG. 51 illustrates an example of a contact lens storage container.

FIG. 51 depicts an example of the channel 1210E defined in the floor 1254E and the associated light transmitter 142E and receiver 146E are adjacent to the channel 1210E where the solution can be analyzed. In the illustrated examples, risers 1270E protrude from off of the floor 1254E to space the contact lens off of the floor 1254E. The risers 1270E are spaced so that the storage solution can pass around the risers 1270E. Thus, the risers 1270E prevent the contact lens from blocking the solution from entering into the channel 1210E.

Figure 52:
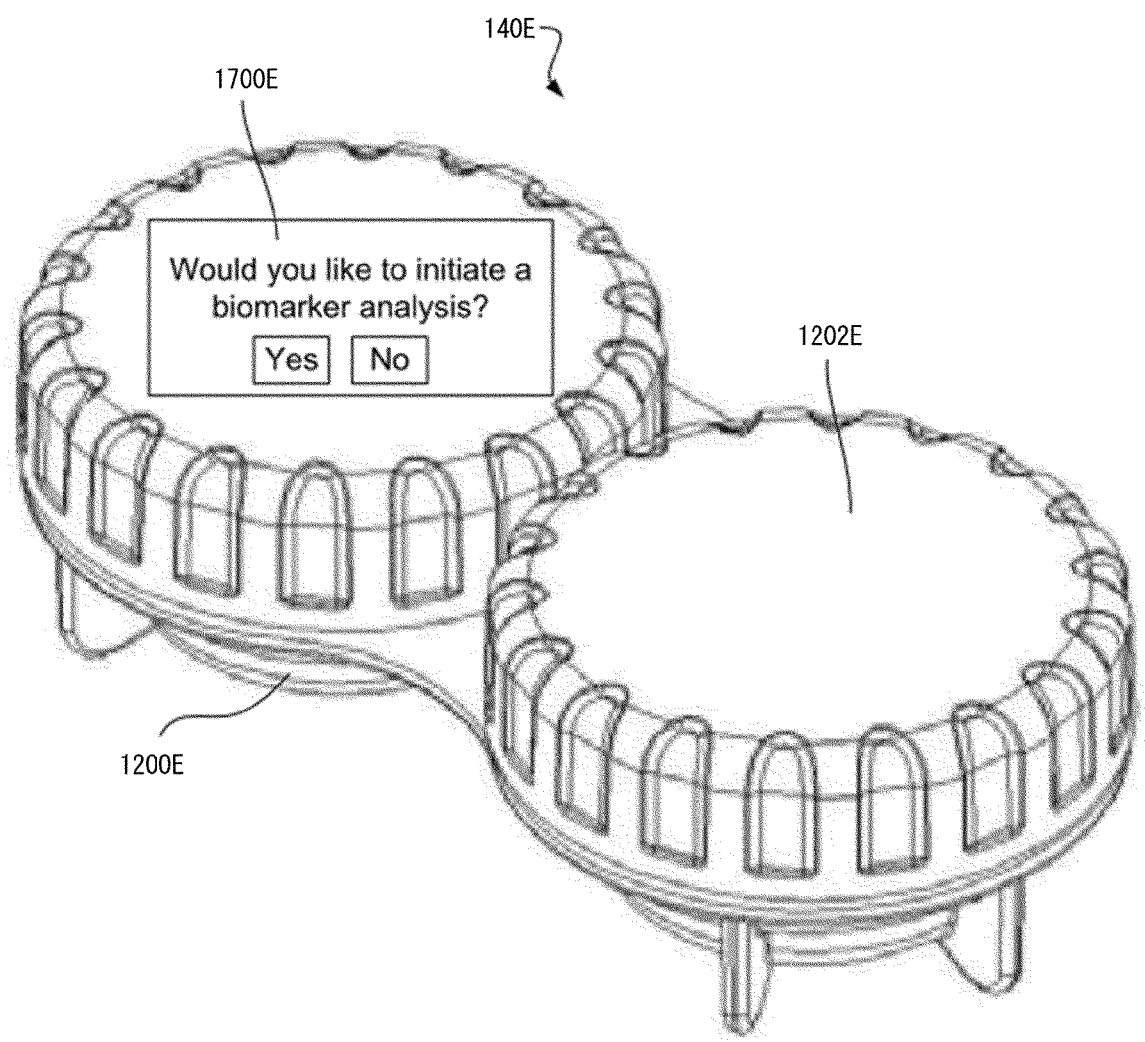
FIG. 52 illustrates an example of a contact lens storage container.

FIG. 52 depicts an example of a contact lens container 140E with a user interface 1700E. The user interface 1700E may be used to present messages to the user or present options to the user. The user may also use the user interface 1700E to give instructions to the contact lens container 140E. In other examples, the user interface is incorporated into a device that is in communication with the contact lens container 140E. For example, the contact lens container 140E may be in wireless communication with a mobile device, and the user interface of the mobile device may operate as an interface between the container and the user. In other examples, the user interface may be hardwired to the container 140E. A non-exhaustive list of devices that may be in communication with the container and provide a user interface include, but are not limited to, a mobile device, a smart phone, an electronic tablet, a laptop, a desktop, a computing device, a networked device, another type of device, or combinations thereof.

While the example of FIG. 52 depicts the user interface 1700E incorporated into the lid portion 1202E of the container 140E, the user interface 1700E may be incorporated into any appropriate portion of the container 140E. For example, the user interface 1700E may be incorporated into the body portion 1200E, the side of the container, the undersurface of the container, another portion of the container, or combinations thereof.

Examples of messages that may be presented to the user include the results of the analysis, an option to initiate the analysis, a request to change batteries, a request to replace the storage solution, a schedule of when the analysis is to be performed, an option to test for specific health conditions, a request to tighten the lid portion, a request to replace a light source or another component of the container, a request to insert the contact lens, a request for permission to send the results of a test to remote device, another type of message, or combinations thereof.

Examples of instructions that the user may communicate to the container through the user interface includes initiating a test, restricting the testing to specific types of conditions, limiting the range of wavelengths, setting a time to cause a test to be run, sending the test results to a remote device, to discontinue a test, to not perform a test, another type of instructions, or combinations thereof.

Embodiment 7

Figure 53:
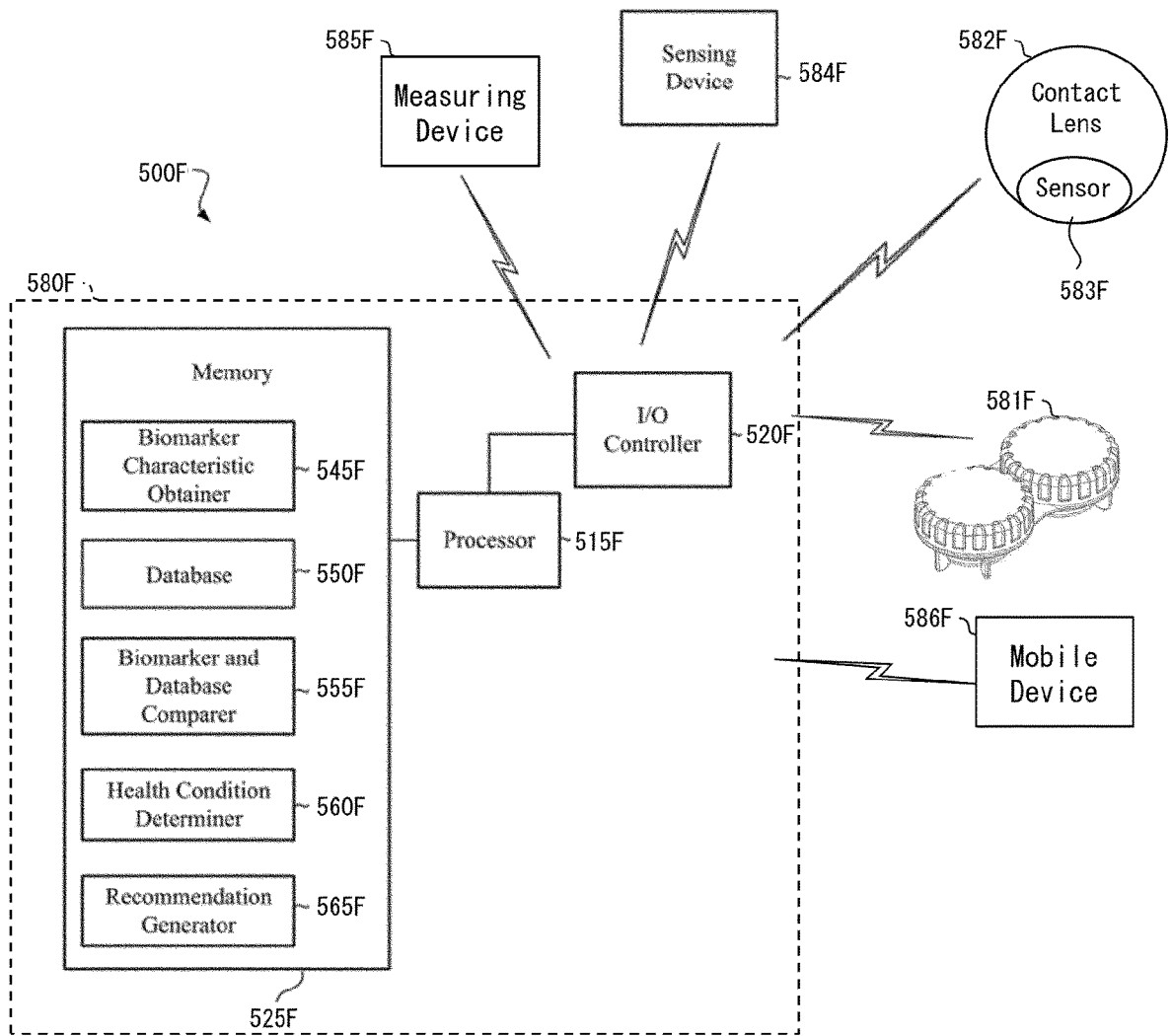
FIG. 53 depicts a diagram of a determination system.

FIG. 53 depicts a diagram of a determination system 500F. The system 500F includes a computing device 580F, a storage container 581F, contact lens 582F, a sensing device 584F, a measuring device 585F, and a mobile device 586F. The computing device 580F comprises a processor 515F, an I/O controller 520F, and a memory 525F. The contact lens 582F includes a sensor 583F. The storage container 581F may comprise a sensor as the storage container 140E of the embodiment 6. The storage container 581F may not comprise any sensor. The contact lens 582F is used by a target person for the determination system 500F. The sensor 583F is not particularly limited provided that it detects information related to an eye of the target person. For example, the sensor 583F may be a sensor for detecting a biomarker described in the embodiment 1. The sensor 583F may be a glucose sensor for measuring glucose levels as described in the embodiment 3. The sensor 583F may be a sensor for measuring the absolute intraocular pressure of the eye as described in the embodiment 4. The sensor 583F may be a sensor for measuring the relative intraocular pressure of the eye as described in the embodiment 5. In some examples, a sensor of the sensing device 584F is incorporated into a hand-held device, an independent machine configured to analyze the solution, another type of sensor, or combinations thereof. The measuring device 585F carries out measurement related to an eye of the target person. The measuring device 585F may be a visual acuity testing device, a fundus examination device, an intraocular pressure examination device, or the like. The mobile device 586F is used by the target person.

The computing device 580F (i) obtains information related to an eye of a target person from a plurality of data sources and (ii) makes a determination of a predetermined matter related to the target person based on at least part of the information. The plurality of data sources include two or more of the sensor 583F included in a contact lens 582F of the target person, a sensor included in the storage container 581F, a measurement device 585F which carries out measurement related to the eye of the target person, tear fluid of the target person, a storage solution of a contact lens (contact lens 582F or other contact lens), and a diagnostic process of the target person. In a case where the data source includes the diagnostic process, the computing device 580F may make the determination of the predetermined matter based on information obtained through the diagnostic process. The information obtained through the diagnostic process may be an information indicating an interview result of the diagnostic process by a doctor, for example. According to the system 500F including the computing device 580F, it is possible to make various determinations based on the plurality of data sources. Note that the computing device 580F may obtain the information from the plurality of data sources directly or indirectly via another device. In a case of obtaining the information indirectly, the computing device 580F may obtain, as the information, information which has been obtained from any of the plurality of data sources and processed by the another device.

The information used for the determination may contain a biomarker derived from at least one of the contact lens, the tear fluid, and the storage solution. The biomarker may be obtained by the sensor 583F, the measuring device 585F, or the sensing device 584F. The computing device 580F may make the determination of the predetermined matter based on the biomarker detected by the sensor 583F, the biomarker detected by the sensor included in the storage container 581F, or both of the biomarkers.

The computing device 580F may make the determination of the predetermined matter based on (i) the biomarker detected by the sensor included in the storage container 581F which contains the contact lens worn by the target person for a predetermined period or more and (ii) the biomarker detected in time series by the sensor 583F while the contact lens 582F was worn by the target person. According to this configuration, it is possible to make a determination in consideration of both (i) a change in state of the eye during the use of the contact lens 582F and (ii) build-ups on the contact lens. For example, the computing device 580F may make a determination of an extent of dryness of the eye is based on the biomarker detected in time series by the sensor 583F, and may make a determination of a presence or absence of an allergic reaction based on the biomarker detected by the sensor included in the storage container 581F. And then the computing device 580F may make a determination of a contact lens which is recommendable to the target person in accordance with the extent of dryness of the eye and the presence or absence of an allergic reaction thus determined. Further, the computing device 580F may make a determination of a health condition of the target person, in consideration of both (i) a change in state of the eye during the use of the contact lens and (ii) build-ups on the contact lens. Of course, the computing device 580F can make determination based of the information obtained from three or more data sources.

The computing device 580F may make a determination of the predetermined matter based on (i) the information obtained from the plurality of data sources and (ii) the information obtained by the mobile device 586F. According to this configuration, the computing device 580F can make a determination also in consideration of the information obtained by the mobile device 586F. The information is not particularly limited provided that it can be used for the determination. The information may be information which is inputted to the mobile device 586F by the target person and is indicative of the condition of the target person, an image of the eye of the target person captured with the mobile device 586F, or the positional information of the mobile device 586F, for example. Use of the positional information allows, for example, identifying a region in which the target person is active and making a determination of a recommendable contact lens in accordance with the amount of pollen in the air in the region.

The predetermined matter may be a health condition of the target person, as described in the embodiment 1. The health condition may be an ophthalmic health condition. The health condition may be a condition which is not directly relating to the eye (glucose level described in the embodiment 3, for example). In these cases, the determination may be conducted by the health condition determiner 560F.

The predetermined matter may be what type of contact lens is recommendable to the target person, as described in the embodiment 2. In this case, the determination may be conducted by a recommendation generator 565F. Note that the predetermined matter may be a matter which can be determined based on the information obtained from the data sources described in the embodiment 7 and the above-described embodiments, and are not limited to those examples. For example, a plurality of target persons can be classified in accordance with information obtained with respect to the plurality of target persons (determination can be made as to which one of predetermined categories each target person belongs). For example, the plurality of target persons can be categorized into a group of target persons who are prone to have a certain illness and a group of target persons who are not.

A determination method conducted by the computing device 580F includes the steps of: obtaining information related to an eye of the target person from a plurality of data sources described above, and determining the predetermined matter related to the target person based on at least part of the information. The present invention encompasses in its scope a program which causes a computer to execute the steps.

The invention claimed is:

1. A determination system comprising
a computing device adapted to
(i) obtain information relating to an eye of a target person from a plurality of data sources, and
(ii) make a determination of a predetermined matter related to the target person based on at least part of the information,
wherein the plurality of data sources including two or more of:
a sensor included in a contact lens of the target person,
a sensor included in a storage container of the contact lens,
a measurement device which carries out measurement related to the eye of the target person,
tear fluid of the target person,
a storage solution of the contact lens, and
a diagnostic process of the target person, and
wherein the predetermined matter is what type of contact lens is recommendable to the target person; and
wherein the computing device determines an extent of dryness of the eye of the target person based on a biomarker detected in time series by the sensor included in the contact lens, and determines a presence or absence of an allergic reaction of the target person based on a biomarker detected by the sensor included in the storage container, and determines a contact lens which is recommendable to the target person in accordance with the extent of dryness of the eye thus determined and the presence or absence of the allergic reaction thus determined.

2. The determination system according to claim 1, wherein the determination system comprising the plurality of data sources.

3. The determination system according to claim 1, wherein the information from the plurality of data sources used for the determination comprises information relating to a biomarker derived from at least one of the contact lens, the tear fluid, and the storage solution.

4. The determination system according to claim 1, wherein the computing device makes the determination of the predetermined matter based on information from the measurement device and the information obtained through the diagnostic process.

5. The determination system according to claim 1, comprising a contact lens including a sensor as at least one of the plurality of data sources, wherein the computing device makes the determination of the predetermined matter based on a biomarker detected by the sensor included in the contact lens.

6. The determination system according to claim 5 comprising a storage container including a sensor as at least one of the plurality of data sources, wherein the computing device makes the determination of the predetermined matter further based on the biomarker detected by the sensor included in the storage container.

7. The determination system according to claim 6, wherein
the computing device makes the determination of the predetermined matter based on
(i) the biomarker detected by the sensor included in the storage container which contains the contact lens worn by the target person, and
(ii) the biomarker detected in time series by the sensor included in the contact lens while the contact lens was worn by the target person.

8. The determination system according to claim 1, wherein the computing device makes the determination of the predetermined matter based on
(i) the information obtained from the plurality of data sources, and
(ii) information obtained by a mobile device of the target person.

9. The determination system according to claim 1, wherein the information used for the determination of the predetermined matter comprises one or more characteristics obtained from a single data source of the plurality of data sources, wherein the one or more characteristics are selected from the group comprising the concentration and/or type of at least one biomarker, location of the biomarker on a contact lens, chemometric data relating to at least one biomarker, ratio kinetics, peak, plateau, time constant and/or decay.

10. The determination system according to claim 1, wherein the information obtained from one or more of the plurality of data sources relates to one or more from the group comprising a protein and/or an antibody and/or an electrolyte level and/or an iron level and/or a lipid level.

11. A computing device comprising a processor and a memory, wherein
the processor
(i) obtains information related to an eye of a target person from a plurality of data sources, and
(ii) makes a determination of a predetermined matter related to the target person based on at least part of the information,
wherein the plurality of data sources including two or more of:
a sensor included in a contact lens of the target person,
a sensor included in a storage container of the contact lens,
a measurement device which carries out measurement related to the eye of the target person,
tear fluid of the target person,
a storage solution of the contact lens, and
a diagnostic process of the target person, and
wherein the predetermined matter is what type of contact lens is recommendable to the target person; and
wherein the processor determines an extent of dryness of the eye of the target person based on a biomarker detected in time series by the sensor included in the contact lens, and determines presence or absence of an allergic reaction of the target person based on a biomarker detected by the sensor included in the storage container, and determines a contact lens which is recommendable to the target person in accordance with the extent of dryness of the eye thus determined and the presence or absence of the allergic reaction thus determined.

12. A determination method conducted by a computing device, comprising the steps of:
obtaining information related to an eye of a target person from a plurality of data sources; and
making a determination of a predetermined matter related to the target person based on at least part of the information,
wherein the plurality of data sources including two or more of
a sensor included in a contact lens of the target person,
a sensor included in a storage container of the contact lens,
a measurement device which carries out measurement related to the eye of the target person,
tear fluid of the target person,
a storage solution of the contact lens, and
a diagnostic process of the target person, and
wherein the predetermined matter is what type of contact lens is recommendable to the target person,
in the step of making a determination of a predetermined matter, the computing device determines an extent of dryness of the eye of the target person based on a biomarker detected in time series by the sensor included in the contact lens, and determines presence or absence of an allergic reaction of the target person based on a biomarker detected by the sensor included in the storage container, and determines a contact lens which is recommendable to the target person in accordance with the extent of dryness of the eye thus determined and the presence or absence of the allergic reaction thus determined.

13. The determination method according to claim 12, wherein the information obtained for making the determination of the predetermined matter comprises one or more characteristics obtained from a single data source of the plurality of data sources.

14. A non-transitory computer readable storage medium storing a program comprising instructions which, when the program is executed by a computer, causes the computer to execute the steps of the determination method of claim 12.

* * * * *